(12) United States Patent
Kim et al.

(10) Patent No.: US 10,577,355 B2
(45) Date of Patent: Mar. 3, 2020

(54) HETERO RING COMPOUND AND ORGANIC LUMINESCENT ELEMENT COMPRISING SAME

(71) Applicant: LG CHEM, LTD., Seoul (KR)

(72) Inventors: Jin Joo Kim, Daejeon (KR); Sung Kil Hong, Daejeon (KR); Yongbum Cha, Daejeon (KR)

(73) Assignee: LG CHEM, LTD., Seoul (KR)

(*) Notice: Subject to any disclaimer, the term of this patent is extended or adjusted under 35 U.S.C. 154(b) by 178 days.

(21) Appl. No.: 15/553,060

(22) PCT Filed: Sep. 1, 2015

(86) PCT No.: PCT/KR2015/009207
§ 371 (c)(1),
(2) Date: Aug. 23, 2017

(87) PCT Pub. No.: WO2016/137068
PCT Pub. Date: Sep. 1, 2016

(65) Prior Publication Data
US 2018/0244659 A1    Aug. 30, 2018

(30) Foreign Application Priority Data

Feb. 24, 2015 (KR) .................. 10-2015-0025791

(51) Int. Cl.
*H01L 51/00* (2006.01)
*C07D 405/10* (2006.01)
(Continued)

(52) U.S. Cl.
CPC ......... *C07D 405/10* (2013.01); *C07D 209/82* (2013.01); *C07D 307/91* (2013.01); *C07D 333/76* (2013.01); *C07D 403/10* (2013.01); *C07D 409/10* (2013.01); *C09K 11/06* (2013.01); *H01L 51/006* (2013.01); *H01L 51/0054* (2013.01); *H01L 51/0067* (2013.01); *H01L 51/0071* (2013.01); *H01L 51/0072* (2013.01); *H01L 51/0073* (2013.01); *H01L 51/0074* (2013.01); *H01L 51/50* (2013.01); *H01L 51/5024* (2013.01); *H01L 51/5056* (2013.01);
(Continued)

(58) Field of Classification Search
None
See application file for complete search history.

(56) References Cited

U.S. PATENT DOCUMENTS

2004/0251816 A1   12/2004   Leo et al.
2011/0272685 A1   11/2011   Parham et al.
(Continued)

FOREIGN PATENT DOCUMENTS

EP   2581365 A1   4/2013
EP   3042944 A1   7/2016
(Continued)

OTHER PUBLICATIONS

Lee, K. H. et al., "Indenofluorene-Based Blue Fluorescent Compounds and Their Application in Highly Efficient Organic Light-Emitting Diodes", Eur. J. Org. Chem., 2012, 14, 2748-2755.
(Continued)

*Primary Examiner* — Robert S Loewe
(74) *Attorney, Agent, or Firm* — Dentons US LLP

(57) ABSTRACT

The present specification provides a heterocyclic compound and an organic light emitting device including the same.

5 Claims, 3 Drawing Sheets

(51) Int. Cl.
   *C07D 209/82* (2006.01)
   *H01L 51/50* (2006.01)
   *C07D 307/91* (2006.01)
   *C07D 333/76* (2006.01)
   *C07D 403/10* (2006.01)
   *C07D 409/10* (2006.01)
   *C09K 11/06* (2006.01)

(52) U.S. Cl.
   CPC ...... *H01L 51/5072* (2013.01); *H01L 51/5092* (2013.01); *H01L 51/5096* (2013.01); *C09K 2211/1029* (2013.01); *C09K 2211/1044* (2013.01); *C09K 2211/1059* (2013.01); *C09K 2211/1088* (2013.01); *C09K 2211/1092* (2013.01); *H01L 51/0085* (2013.01); *H01L 51/5016* (2013.01)

(56) References Cited

U.S. PATENT DOCUMENTS

2014/0166988 A1   6/2014   Yen et al.
2015/0214492 A1   7/2015   Yen et al.
2017/0018722 A1   1/2017   Jatsch et al.

FOREIGN PATENT DOCUMENTS

| KR | 10-2011-0122130 A | 11/2011 |
| KR | 10-2014-0081879 A | 7/2014 |
| WO | 2003-012890 A | 2/2003 |
| WO | 2013109045 A1 | 7/2013 |

OTHER PUBLICATIONS

Search Report of European Patent Office in Appl'n No. 15883456.4, dated Jun. 21, 2018.

[Figure 1]
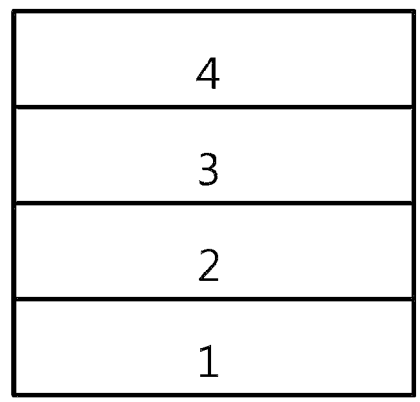
[Figure 2]
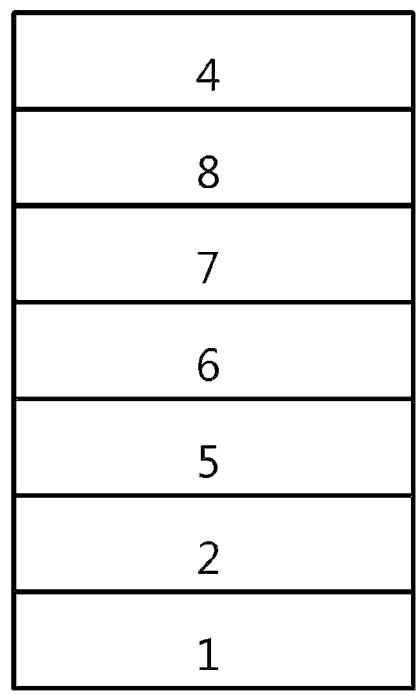

[Figure 3]
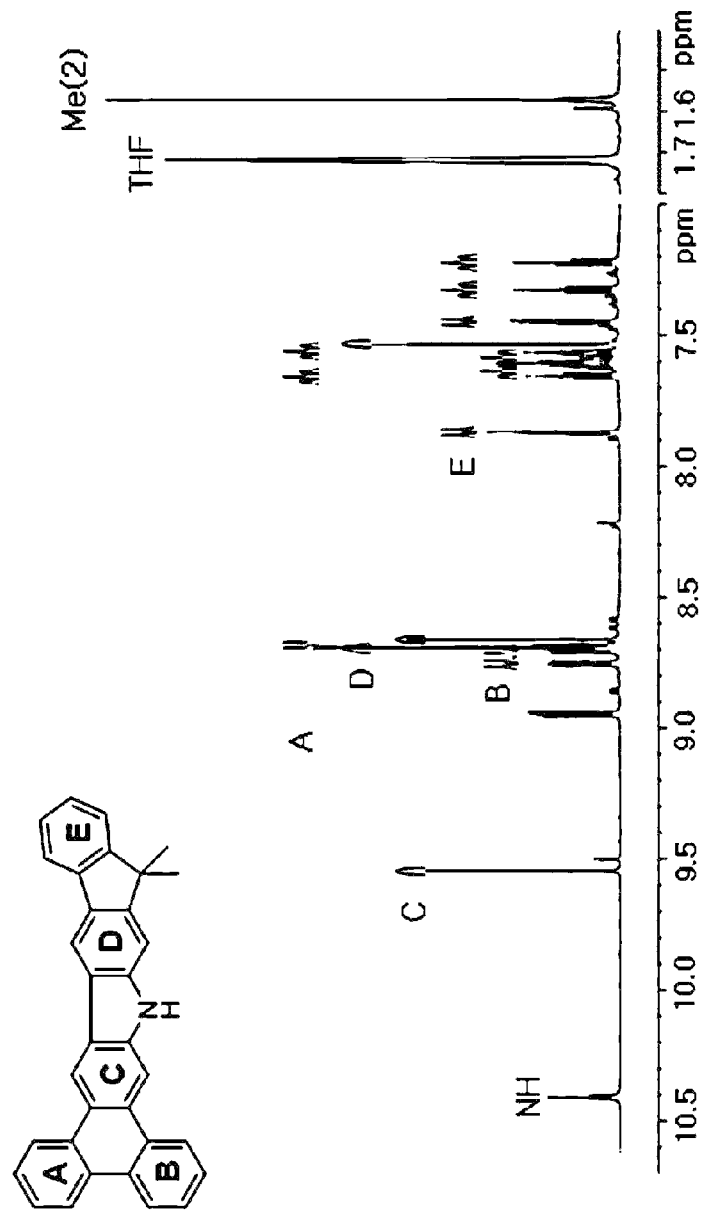

[Figure 4]
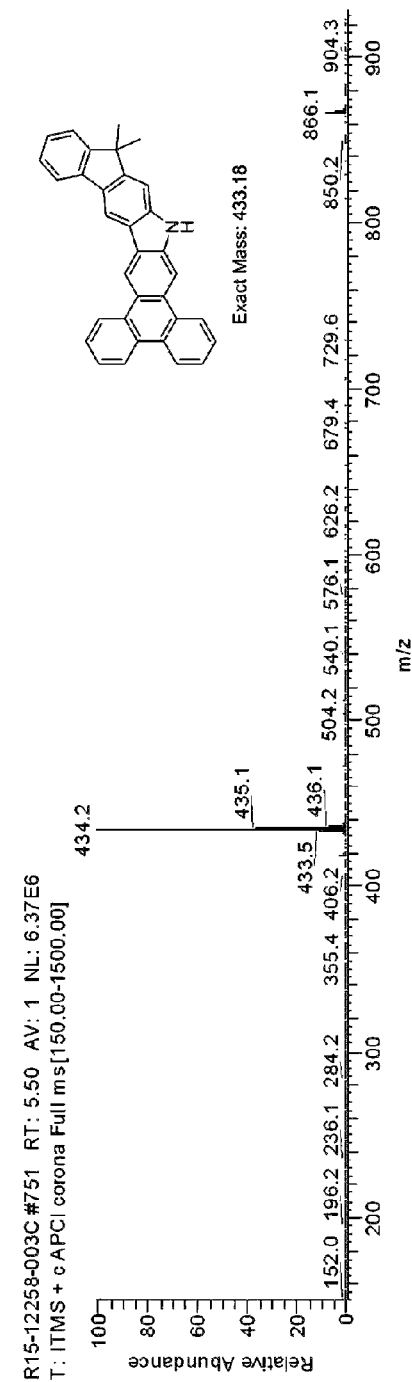

HETERO RING COMPOUND AND ORGANIC LUMINESCENT ELEMENT COMPRISING SAME

TECHNICAL FIELD

This application is a National Stage Entry of International Application No. PCT/KR2015/009207 filed on Sep. 1, 2015, and claims the benefit of Korean Application No. 10-2015-0025791 filed on Feb. 24, 2015, all of which are hereby incorporated by reference in their entirety for all purposes as if fully set forth herein.

The present specification relates to a heterocyclic compound and an organic light emitting device including the same.

BACKGROUND ART

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

DISCLOSURE

Technical Problem

The present specification describes a heterocyclic compound and an organic light emitting device including the same.

Technical Solution

One embodiment of the present specification provides a compound represented by the following Chemical Formula 1:

[Chemical Formula 1]

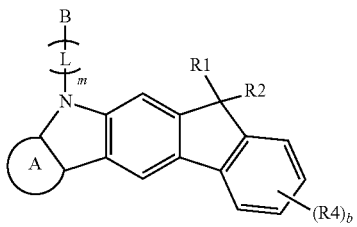

In Chemical Formula 1,

B is hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, L is a direct bond; or a substituted or unsubstituted arylene, R1, R2 and R4 are the same as or different from each other, and each independently hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or bond to adjacent groups to form a substituted or unsubstituted ring, A is triphenylene, b is an integer of 0 to 4, m is an integer of 0 to 10, and when b and m are each two or greater, structures in the parentheses are the same as or different from each other.

Another embodiment of the present specification provides an organic light emitting device including a first electrode; a second electrode provided opposite to the first electrode; and one or more organic material layers provided between the first electrode and the second electrode, wherein one or more layers of the organic material layers include the compound of Chemical Formula 1.

Advantageous Effects

Compounds described in the present specification can be used as a material of an organic material layer of an organic light emitting device. Compounds according to at least one embodiment are capable of efficiency enhancement, a low driving voltage and/or lifespan property enhancement in an organic light emitting device. Particularly, compounds described in the present specification can be used as a material of hole injection, hole transfer, hole injection and hole transfer, light emission, electron transfer, or electron injection. In addition, compounds described in the present specification can be preferably used as a material of a light emitting layer, and electron transfer or electron injection. Particularly, according to one embodiment of the present specification, compounds described in the present specification can be used as a red host or n-type host material, and in this case, the compounds are capable of efficiency enhancement, a low driving voltage and/or lifespan property enhancement. Furthermore, according to one embodiment of the present specification, compounds described in the present specification can be used as a red or green host material of an electron blocking layer, a hole transfer layer and a light emitting layer depending on the types of substituents bonding to N.

DESCRIPTION OF DRAWINGS

FIG. 1 is a diagram showing an example of an organic light emitting device formed with a substrate (1), an anode (2), a light emitting layer (3) and a cathode (4).

FIG. 2 is a diagram showing an example of an organic light emitting device formed with a substrate (1), an anode (2), a hole injection layer (5), a hole transfer layer (6), a light emitting layer (7), an electron transfer layer (8) and a cathode (4).

FIG. 3 is a diagram showing an NMR material as a material identifying the synthesis of a core structure according to one embodiment of the present specification.

FIG. 4 is a diagram showing an LC/MS material as a material identifying the synthesis of a core structure according to one embodiment of the present specification.

MODE FOR DISCLOSURE

Hereinafter, the present specification will be described in more detail.

One embodiment of the present specification provides a compound represented by Chemical Formula 1.

Examples of the substituents are described below, however, the substituents are not limited thereto.

The term "substituted or unsubstituted" means being substituted with one or more substituents selected from the group consisting of deuterium; a halogen group; a nitrile group; a nitro group; a hydroxyl group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; and a heterocyclic group, or having no substituents, or being substituted with a substituent linking two or more substituents among the substituents illustrated above, or having no substituents. For example, "a substituent linking two or more substituents" may include a biphenyl group. In other words, a biphenyl group may be an aryl group, or interpreted as a substituent linking two phenyl groups.

According to one embodiment of the present specification, the term "substituted or unsubstituted" means being substituted with one or more substituents selected preferably from the group consisting of deuterium; a halogen group; a nitrile group; a nitro group; a silyl group substituted with an alkyl group; an alkyl group; an arylphosphine group; an arylamine group; a heteroarylamine group; an arylheteroarylamine group; an aryl group; and a heterocyclic group, or having no substituents.

According to one embodiment of the present specification, the term "substituted or unsubstituted" means being substituted with one or more substituents selected preferably from the group consisting of deuterium; a halogen group; a nitrile group; a nitro group; a silyl group substituted with an alkyl group; an alkyl group; an arylphosphine group; an arylamine group; a heteroarylamine group; an arylheteroarylamine group; an aryl group having 3 to 50 carbon atoms; and a heterocyclic group including P, O, S or N, or having no substituents.

According to one embodiment of the present specification, the term "substituted or unsubstituted" means being substituted with one or more substituents selected preferably from the group consisting of deuterium; a halogen group; a nitrile group; a nitro group; a silyl group substituted with an alkyl group; an alkyl group; an arylphosphine group; an arylamine group; a heteroarylamine group; an arylheteroarylamine group; a phenyl group; a biphenyl group; a naphthyl group; a phenanthryl group; a triphenylene group; a fluorenyl group substituted with an alkyl group; a dibenzofuranyl group; a dibenzothiophene group; a pyridyl group; a pyrimidyl group; a triazine group; and a quinazoline group, or having no substituents.

In the present specification, an "adjacent" group may mean a substituent substituting an atom directly linking to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as "adjacent" groups.

In the present specification, the number of carbon atoms of the carbonyl group is not particularly limited, but is preferably 1 to 40. Specifically, compounds having structures such as below may be included, but the compound is not limited thereto.

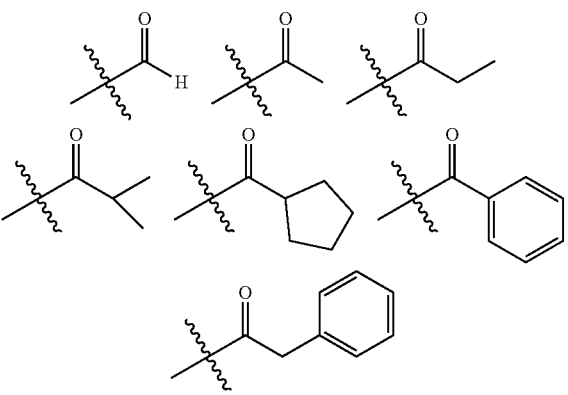

In the present specification, in the ester group, the oxygen of the ester group may be substituted with a linear, branched or cyclic alkyl group having 1 to 25 carbon atoms or an aryl group having 6 to 25 carbon atoms. Specifically, compounds having the following structural formulae may be included, but the compound is not limited thereto.

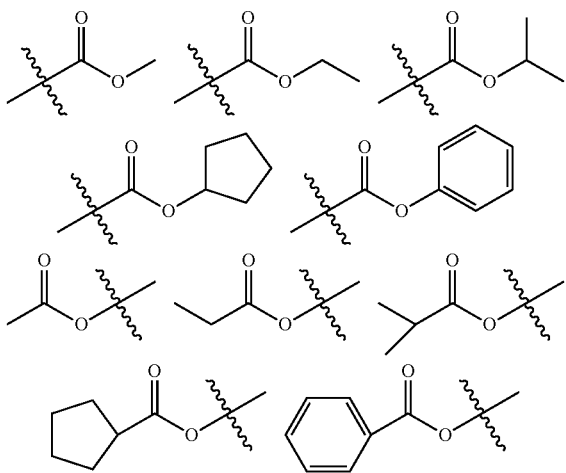

In the present specification, the number of carbon atoms of the imide group is not particularly limited, but is preferably 1 to 25. Specifically, compounds having structures such as below may be included, but the compound is not limited thereto.

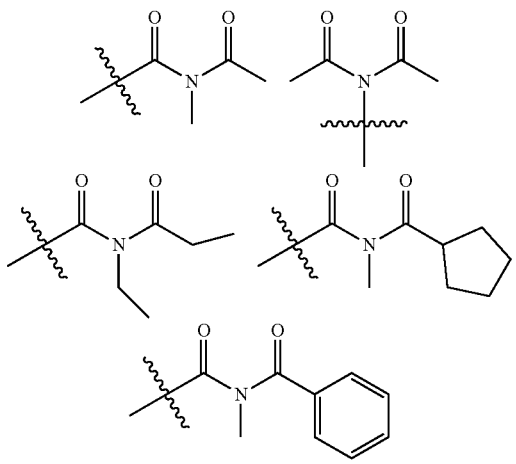

In the present specification, the silyl group may be expressed as the chemical formula of —SiRR'R", and R, R' and R" may each be hydrogen; a substituted or unsubstituted alkyl group; or a substituted or unsubstituted aryl group. Specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group may be expressed as the chemical formula of —BRR'R", and R, R' and R" may each be hydrogen; a substituted or unsubstituted alkyl group; or a substituted or unsubstituted aryl group. Specific examples of the boron group include a trimethylboron group, a triethylboron group, a t-butyldimethylboron group, a triphenylboron group, a phenylboron group and the like, but are not limited thereto.

In the present specification, examples of the halogen group include fluorine, chlorine, bromine or iodine.

In the present specification, the alkyl group may be linear or branched, and the number of carbon atoms is not particularly limited, but is preferably 1 to 40. According to one embodiment, the alkyl group has 1 to 20 carbon atoms. According to another embodiment, the alkyl group has 1 to 10 carbon atoms. According to another embodiment, the alkyl group has 1 to 6 carbon atoms. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentyl-methyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl, 5-methylhexyl and the like, but are not limited thereto.

In the present specification, the alkenyl group may be linear or branched, and although not particularly limited thereto, the number of carbon atoms is preferably 2 to 40. According to one embodiment, the alkenyl group has 2 to 20 carbon atoms. According to another embodiment, the alkenyl group has 2 to 10 carbon atoms. According to another embodiment, the alkenyl group has 2 to 6 carbon atoms. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, the cycloalkyl group is not particularly limited, but preferably has 3 to 60 carbon atoms, and according to one embodiment, the cycloalkyl group has 3 to carbon atoms. According to another embodiment, the cycloalkyl group has 3 to 20 carbon atoms. According to another embodiment, the cycloalkyl group has 3 to 6 carbon atoms. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group, or a multicyclic aryl group. The arylamine group including two or more aryl groups may include a monocyclic aryl group, a multicyclic aryl group, or both a monocyclic aryl group and a multicyclic aryl group.

Specific examples of the arylamine group include phenylamine, naphthylamine, biphenylamine, anthracenylamine, 3-methyl-phenylamine, 4-methyl-naphthylamine, 2-methyl-biphenylamine, 9-methyl-anthracenylamine, a diphenyl amine group, a phenylnaphthylamine group, a ditolylamine group, a phenyltolylamine group, carbozole, a triphenylamine group and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroaryl group in the heteroarylamine group may be a monocyclic heterocyclic group or a multicyclic heterocyclic group. The heteroarylamine group including two or more heterocyclic groups may include a monocyclic heterocyclic group, a multicyclic heterocyclic group, or both a monocyclic heterocyclic group and a multicyclic heterocyclic group.

In the present specification, the arylheteroarylamine group means an amine group substituted with an aryl group and a heterocyclic group.

In the present specification, examples of the arylphosphine group include a substituted or unsubstituted monoarylphosphine group, a substituted or unsubstituted diarylphosphine group, or a substituted or unsubstituted triarylphosphine group. The aryl group in the arylphosphine group may be a monocyclic aryl group or a multicyclic aryl group. The arylphosphine group including two or more aryl groups may include a monocyclic aryl group, a multicyclic aryl group, or both a monocyclic aryl group and a multicyclic aryl group.

In the present specification, the aryl group is not particularly limited, but preferably has 6 to 60 carbon atoms, and may be a monocyclic aryl group or a multicyclic aryl group. According to one embodiment, the aryl group has 6 to 30 carbon atoms. According to one embodiment, the aryl group has 6 to 20 carbon atoms. Examples of the aryl groups a monocyclic aryl group may include a phenyl group, a biphenyl group, a terphenyl group and the like, but are not limited thereto. Examples of the multicyclic aryl group may include a naphthyl group, an anthracenyl group, a phenanthryl group, a pyrenyl group, a perylenyl group, a crycenyl group, a fluorenyl group and the like, but are not limited thereto.

In the present specification, the fluorenyl group may be substituted, and two substituents may bond to each other to form a spiro structure.

When the fluorenyl group is substituted,

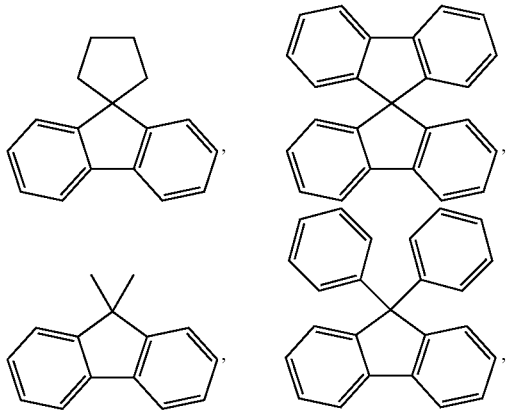

and the like may be included. However, the structure is not limited thereto.

In the present specification, the heterocyclic group is a heterocyclic group including one or more of N, O, P, S, Si and Se as a heteroatom, and although not particularly limited thereto, the number of carbon atoms is preferably 2 to 60. According to one embodiment, the heterocyclic group preferably has 2 to 40 carbon atoms. According to one embodiment, the heterocyclic group preferably has 2 to 20 carbon atoms. Examples of the heterocyclic group include a thiophene group, a furan group, a pyrrole group, an imidazole group, a triazole group, an oxazole group, an oxadiazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group and the like, but are not limited thereto.

In the present specification, descriptions on the heterocyclic group made above may be used for the heteroaryl group except that the heteroaryl group is aromatic.

In the present specification, descriptions on the aryl group made above may be used for the aryl group in the aryloxy group, the arylthioxy group, the arylsulfoxy group, the arylphosphine group, the aralkyl group, the aralkylamine group, the aralkenyl group, the alkylaryl group, the arylamine group and the arylheteroarylamine group.

In the present specification, descriptions on the alkyl group made above may be used for the alkyl group in the alkylthioxy group, the alkylsulfoxy group, the aralkyl group, the aralkylamine group, the alkylaryl group and the alkylamine group.

In the present specification, descriptions on the heterocyclic group made above may be used for the heteroaryl group in the heteroaryl group, the heteroarylamine group and the arylheteroarylamine group.

In the present specification, descriptions on the alkenyl group made above may be used for the alkenyl group in the aralkenyl group.

In the present specification, the descriptions on the aryl group made above may be used for the arylene except that the arylene is a divalent group.

In the present specification, the descriptions on the heterocyclic group made above may be used for the heteroarylene except that the heteroarylene is divalent.

In the present specification, the meaning of bonding to adjacent groups to form a ring means bonding to adjacent groups to form a substituted or unsubstituted aliphatic hydrocarbon ring; a substituted or unsubstituted aromatic hydrocarbon ring; a substituted or unsubstituted aliphatic heteroring; a substituted or unsubstituted aromatic heteroring; or a fused ring thereof.

In the present specification, the aliphatic hydrocarbon ring means a ring that is not aromatic, and a ring formed with only carbon and hydrogen atoms.

In the present specification, examples of the aromatic hydrocarbon ring include a phenyl group, a naphthyl group, an anthracenyl group and the like, but are not limited thereto.

In the present specification, the aliphatic heteroring means an aliphatic ring including one or more of heteroatoms.

In the present specification, the aromatic heteroring means an aromatic ring including one or more of heteroatoms.

In the present specification, the aliphatic hydrocarbon ring, the aromatic hydrocarbon ring, the aliphatic heteroring and the aromatic heteroring may be monocyclic or multicyclic.

According to one embodiment of the present specification, A may be any one selected from among the following structures.

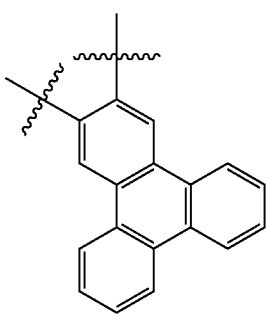

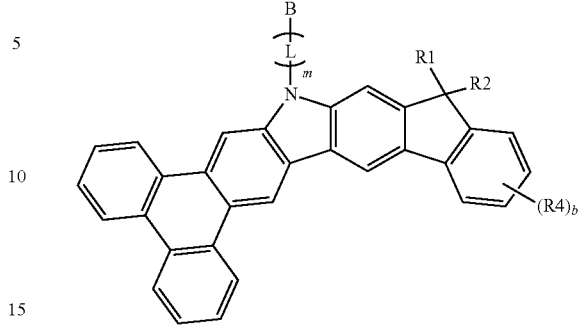

[Chemical Formula 3]

In Chemical Formulae 2 and 3, definitions of R1, R2, R4, B, L, m and b are the same as in Chemical Formula 1.

According to one embodiment of the present specification, L is a direct bond; or arylene unsubstituted or substituted with one or more substituents selected from the group consisting of deuterium, a halogen group, a nitrile group, a nitro group, a silyl group substituted with an alkyl group, an alkyl group, an arylphosphine group, an aryl group and a heterocyclic group.

According to one embodiment of the present specification, L is a direct bond; or a substituted or unsubstituted monocyclic to tricyclic arylene.

According to one embodiment of the present specification, L is a direct bond; or arylene having 6 to 30 carbon atoms.

According to one embodiment of the present specification, L is a direct bond, or may be any one selected from among the following structures.

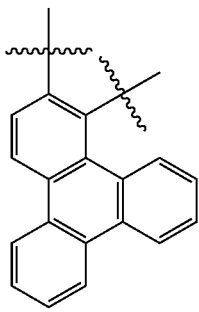

In the above-mentioned structures,

represents a site to which A is linked.

According to one embodiment of the present specification, Chemical Formula 1 may be represented by the following Chemical Formula 2 or 3.

[Chemical Formula 2]

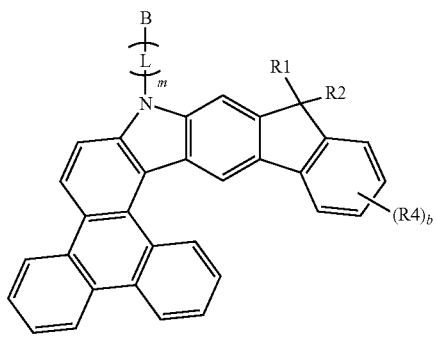

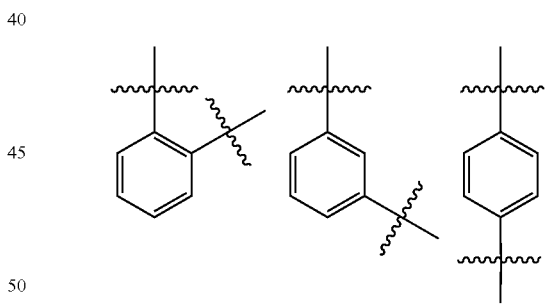

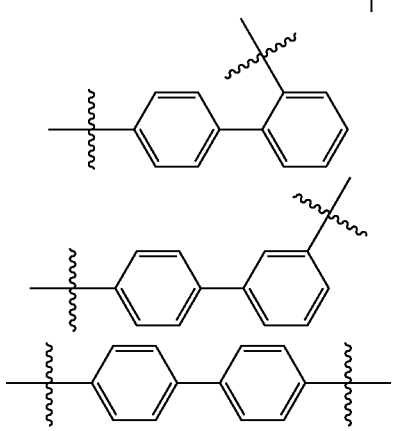

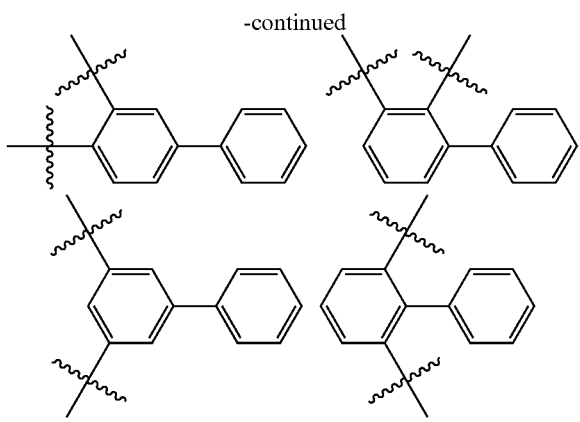

The structures may be unsubstituted or substituted with one or more substituents selected from the group consisting of deuterium; a halogen group; a nitrile group; a nitro group; a hydroxyl group; a carbonyl group; an ester group; an imide group; an amine group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylheteroarylamine group; an arylphosphine group; and a heterocyclic group.

According to one embodiment of the present specification, L is a direct bond; substituted or unsubstituted phenylene; or substituted or unsubstituted biphenylylene.

According to one embodiment of the present specification, L is a direct bond; phenylene unsubstituted or substituted with one or more substituents selected from the group consisting of deuterium, a halogen group, a nitrile group, a nitro group, a silyl group substituted with an alkyl group, an alkyl group, an arylphosphine group, an aryl group and a heterocyclic group; or biphenylylene unsubstituted or substituted with one or more substituents selected from the group consisting of deuterium, a halogen group, a nitrile group, a nitro group, a silyl group substituted with an alkyl group, an alkyl group, an arylphosphine group, an aryl group and a heterocyclic group.

According to one embodiment of the present specification, L is a direct bond; phenylene; or biphenylylene.

According to one embodiment of the present specification, B is hydrogen; deuterium; a halogen group; a nitrile group; a nitro group; a hydroxyl group; a substituted or unsubstituted alkyl group; a substituted or unsubstituted alkenyl group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group.

According to one embodiment of the present specification, B is a substituted or unsubstituted arylamine group; a substituted or unsubstituted arylphosphine group; a substituted or unsubstituted aryl group; or a substituted or unsubstituted heterocyclic group.

According to one embodiment of the present specification, B is an arylamine group unsubstituted or substituted with one or more substituents selected from the group consisting of deuterium, a halogen group, a nitrile group, a nitro group, a silyl group substituted with an alkyl group, an alkyl group, an arylphosphine group, an aryl group and a heterocyclic group; an arylphosphine group unsubstituted or substituted with one or more substituents selected from the group consisting of deuterium, a halogen group, a nitrile group, a nitro group, a silyl group substituted with an alkyl group, an alkyl group, an arylphosphine group, an aryl group and a heterocyclic group; an aryl group unsubstituted or substituted with one or more substituents selected from the group consisting of deuterium, a halogen group, a nitrile group, a nitro group, a silyl group substituted with an alkyl group, an alkyl group, an arylphosphine group, an aryl group and a heterocyclic group; or a heterocyclic group unsubstituted or substituted with one or more substituents selected from the group consisting of deuterium, a halogen group, a nitrile group, a nitro group, a silyl group substituted with an alkyl group, an alkyl group, an arylphosphine group, an aryl group unsubstituted or substituted with an alkyl group, and a heterocyclic group.

According to one embodiment of the present specification, B is a substituted or unsubstituted arylamine group; a substituted or unsubstituted arylphosphine group; a substituted or unsubstituted aryl group; or a substituted or unsubstituted heterocyclic group including one or more of N, S, O and P.

According to one embodiment of the present specification, B is a substituted or unsubstituted arylamine group; a substituted or unsubstituted arylphosphine group; a substituted or unsubstituted monocyclic to tricyclic aryl group; or a substituted or unsubstituted monocyclic to hexacyclic heterocyclic group including one or more of N, S, O and P.

According to one embodiment of the present specification, B is an arylamine group unsubstituted or substituted with an alkyl group; an arylphosphine group; a substituted or unsubstituted a phenyl group; a substituted or unsubstituted biphenyl group; a substituted or unsubstituted naphthyl group; a substituted or unsubstituted phenanthryl group; a substituted or unsubstituted fluorenyl group; a substituted or unsubstituted triphenylene group; a substituted or unsubstituted benzimidazole group; a substituted or unsubstituted benzoxazole group; a substituted or unsubstituted benzothiazole group; a substituted or unsubstituted triazine group; a substituted or unsubstituted pyridyl group; a substituted or unsubstituted pyrimidyl group; a substituted or unsubstituted quinazoline group; a substituted or unsubstituted quinolinyl group; a substituted or unsubstituted quinoxaline group; a substituted or unsubstituted dibenzofuranyl group; a substituted or unsubstituted dibenzothiophene group; a substituted or unsubstituted carbazole group; a substituted or unsubstituted benzocarbazole group;

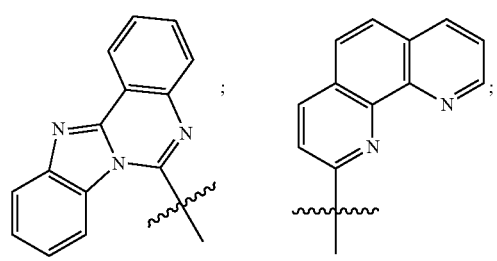

-continued

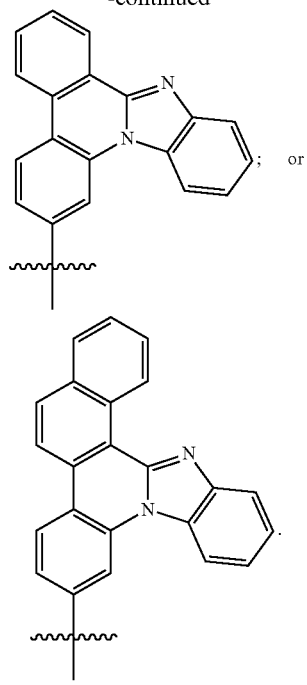

According to one embodiment of the present specification, B is an arylamine group unsubstituted or substituted with an alkyl group; an arylphosphine group; an aryl group unsubstituted or substituted with one or more substituents selected from the group consisting of deuterium, a halogen group, a nitrile group, a silyl group substituted with an alkyl group, an arylamine group, an alkyl group, an aryl group and a heterocyclic group; or a heterocyclic group unsubstituted or substituted with an aryl group unsubstituted or substituted with an alkyl group.

According to one embodiment of the present specification, B is an arylamine group unsubstituted or substituted with an alkyl group; an arylphosphine group; an aryl group unsubstituted or substituted with one or more substituents selected from the group consisting of deuterium, a halogen group, a nitrile group, a silyl group substituted with an alkyl group, an arylamine group, an alkyl group, an aryl group and a heterocyclic group; or a heterocyclic group unsubstituted or substituted with an aryl group.

According to one embodiment of the present specification, B is an arylamine group unsubstituted or substituted with an alkyl group; an arylphosphine group; a phenyl group unsubstituted or substituted with one or more substituents selected from the group consisting of deuterium, a halogen group, a nitrile group, a silyl group substituted with an alkyl group, an arylamine group, an alkyl group, an aryl group and a heterocyclic group; a biphenyl group; a naphthyl group; a phenanthryl group; a fluorenyl group substituted with an alkyl group; a triphenylene group; a benzimidazole group unsubstituted or substituted with an aryl group; a benzoxazole group; a benzothiazole group; a triazine group unsubstituted or substituted with an aryl group; a pyridyl group unsubstituted or substituted with an aryl group; a pyrimidyl group unsubstituted or substituted with an aryl group; a quinazoline group unsubstituted or substituted with an aryl group; a quinolinyl group unsubstituted or substituted with an aryl group; a quinoxaline group unsubstituted or substituted with an aryl group; a dibenzofuranyl group; a dibenzothiophene group; a carbazole group unsubstituted or substituted with an aryl group; a benzocarbazole group unsubstituted or substituted with an aryl group;

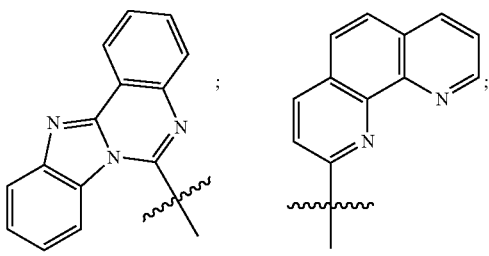

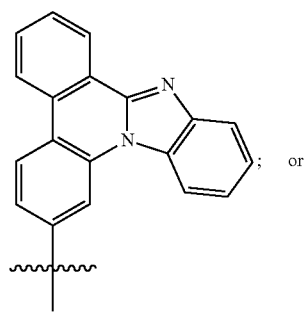

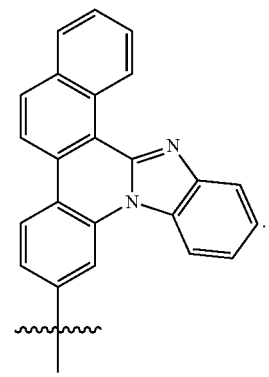

According to one embodiment of the present specification, B is an arylamine group unsubstituted or substituted with an alkyl group; an arylphosphine group; a phenyl group unsubstituted or substituted with one or more substituents selected from the group consisting of deuterium, a halogen group, a nitrile group, a silyl group substituted with an alkyl group, an arylamine group, an alkyl group, an aryl group and a heterocyclic group; a biphenyl group; a naphthyl group; a phenanthryl group; a fluorenyl group substituted with an alkyl group; a triphenylene group; a benzimidazole group unsubstituted or substituted with an aryl group; a benzoxazole group; a benzothiazole group; a triazine group unsubstituted or substituted with an aryl group; a pyridyl group unsubstituted or substituted with an aryl group; a pyrimidyl group unsubstituted or substituted with an aryl group; a quinazoline group unsubstituted or substituted with an aryl group unsubstituted or substituted with an alkyl group; a quinolinyl group unsubstituted or substituted with an aryl group; a quinoxaline group unsubstituted or substituted with an aryl group; a dibenzofuranyl group; a dibenzothiophene group; a carbazole group unsubstituted or substituted with an aryl group unsubstituted or substituted with an alkyl group; a benzocarbazole group unsubstituted or substituted with an aryl group;

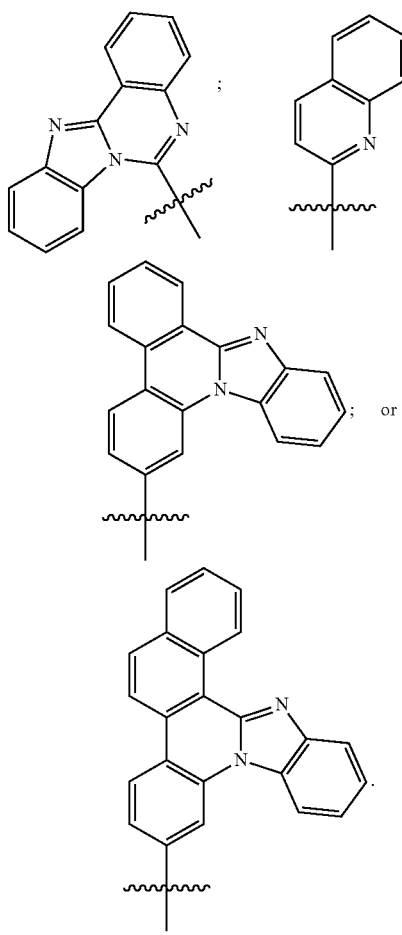

According to one embodiment of the present specification, R1 and R2 are the same as or different from each other, and each independently a substituted or unsubstituted alkyl group.

According to one embodiment of the present specification, R1 and R2 are the same as or different from each other, and each independently a substituted or unsubstituted alkyl group having 1 to 10 carbon atoms.

According to one embodiment of the present specification, R1 and R2 are the same as or different from each other, and each independently an alkyl group unsubstituted or substituted with one or more substituents selected from the group consisting of deuterium, a halogen group, a nitrile group, a nitro group, a silyl group substituted with an alkyl group, an alkyl group, an arylphosphine group, an aryl group and a heterocyclic group.

According to one embodiment of the present specification, R1 and R2 are the same as or different from each other, and each independently an alkyl group.

According to one embodiment of the present specification, R1 and R2 are the same as or different from each other, and each independently an alkyl group having 1 to 10 carbon atoms.

According to one embodiment of the present specification, R1 and R2 are alkyl groups.

According to one embodiment of the present specification, R1 and R2 are alkyl groups having 1 to 10 carbon atoms.

According to one embodiment of the present specification, R1 and R2 are alkyl groups having 1 to 5 carbon atoms.

According to one embodiment of the present specification, R1 and R2 are methyl groups.

According to one embodiment of the present specification, R4 is deuterium, a halogen group, a nitrile group, a nitro group, a hydroxyl group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylheteroarylamine group, an arylphosphine group or a heterocyclic group.

According to one embodiment of the present specification, R4 is hydrogen, deuterium, a halogen group, a nitrile group, an alkoxy group, an alkyl group, an aryl group, a heteroarylamine group, an arylamine group, an arylheteroarylamine group, an arylphosphine group or a heterocyclic group.

According to one embodiment of the present specification, R4 is hydrogen; or deuterium.

According to one embodiment of the present specification, R4 is hydrogen.

According to one embodiment of the present specification, m is an integer of 0 to 5.

According to one embodiment of the present specification, m is an integer of 0 to 3.

According to one embodiment of the present specification, m is an integer of 0 to 2.

According to one embodiment of the present specification, m is 0 or 1.

According to one embodiment of the present specification, m is 1.

According to one embodiment of the present specification, m is 0.

According to one embodiment of the present invention, the compound of Chemical Formula 1 may be any one selected from among the following compounds.

1-1

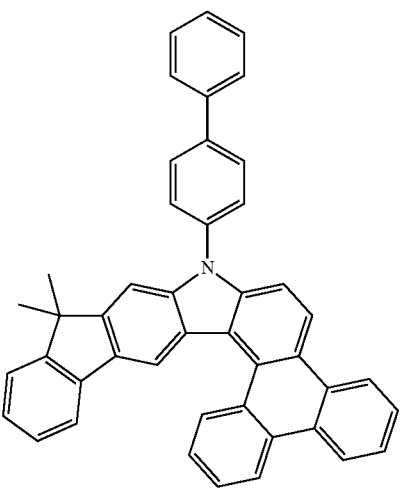

1-2
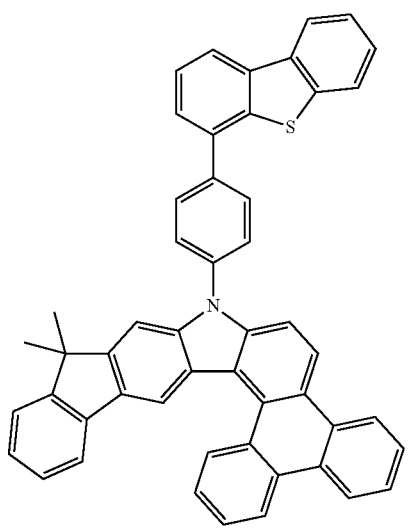
1-3
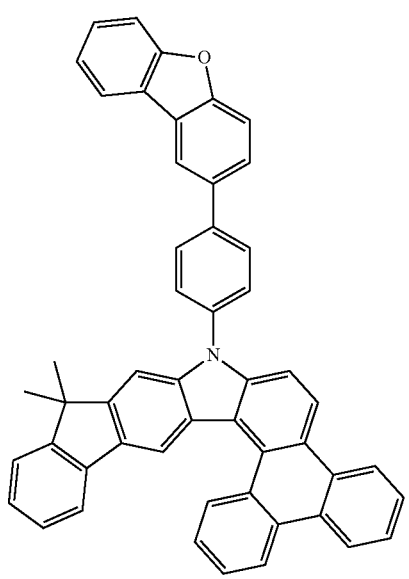
1-4
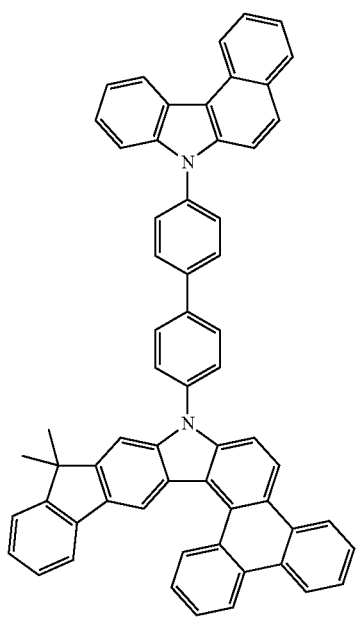
1-5
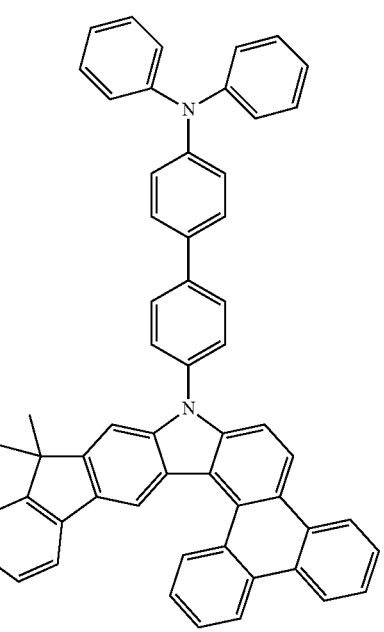

1-6
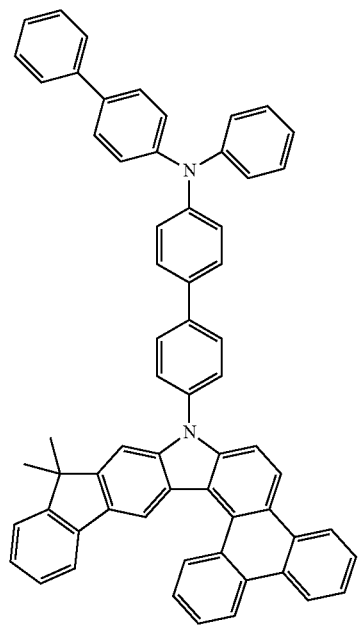
1-7
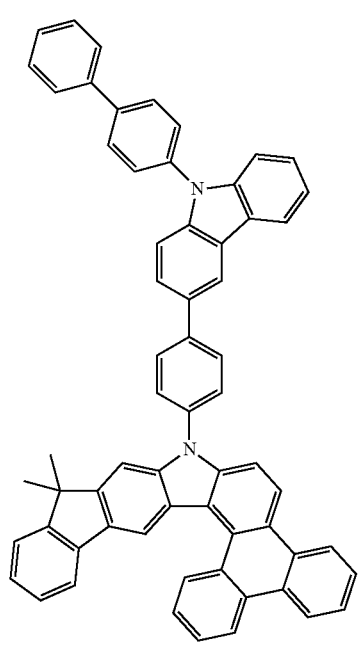
1-8
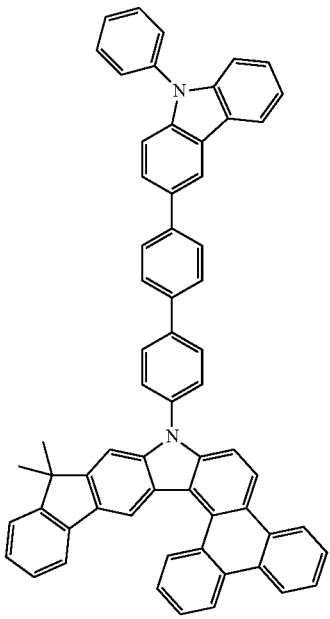
1-9
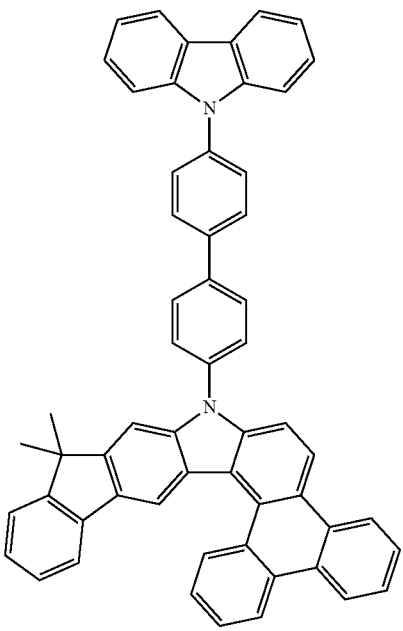

-continued
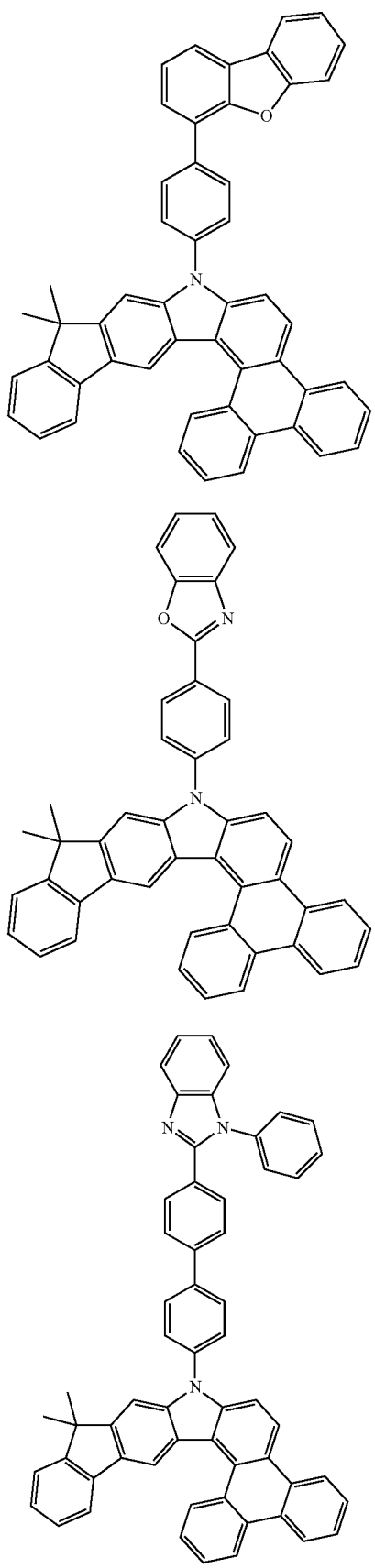
1-10
1-11
1-12
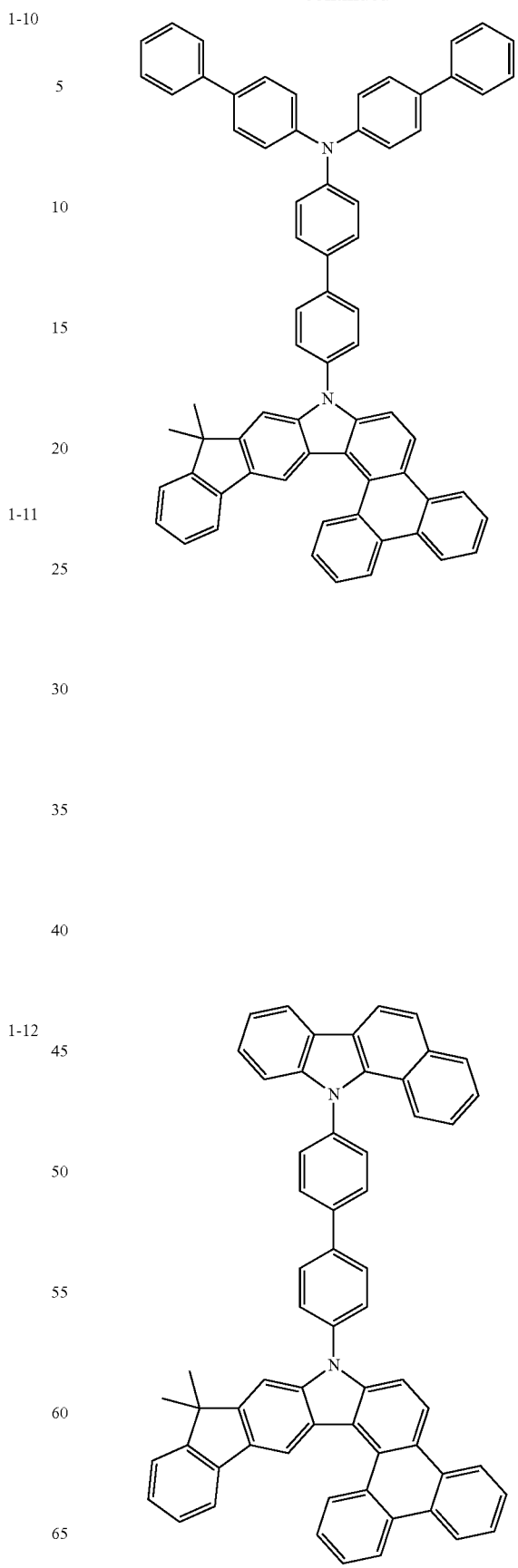
1-13
1-14

-continued
1-15
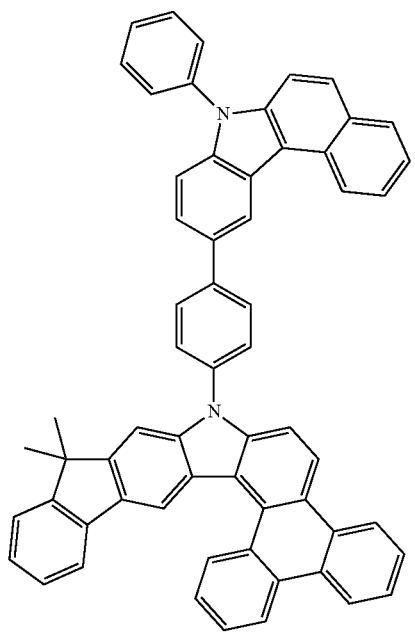
1-16
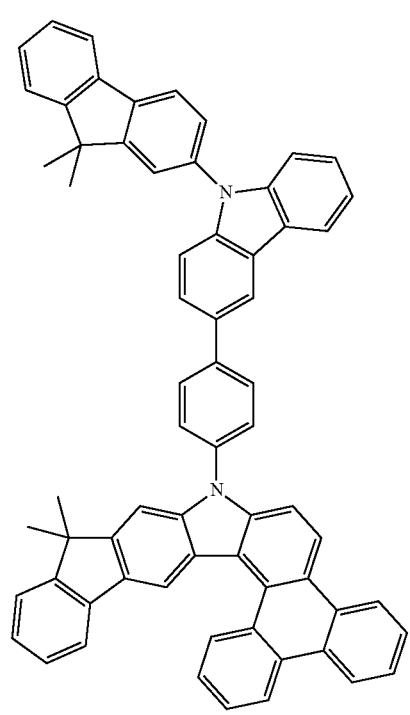
-continued
1-17
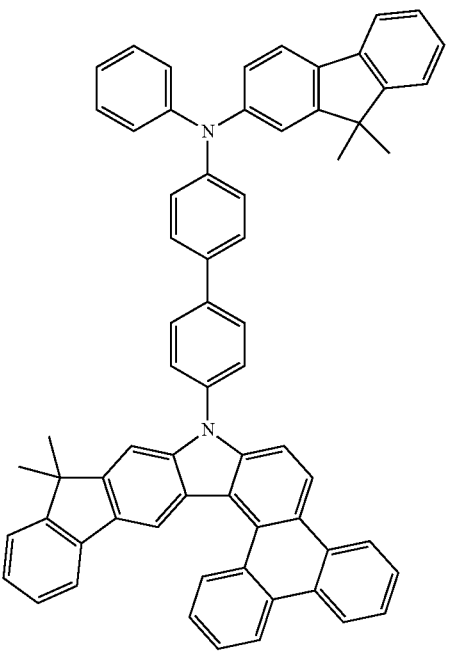
1-18
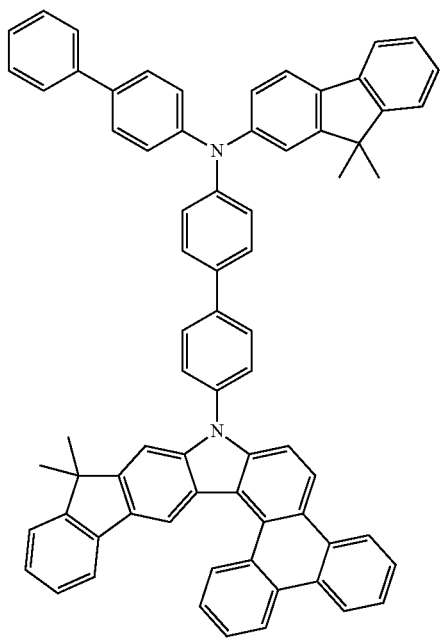

1-19
1-20
1-21
1-22
1-23
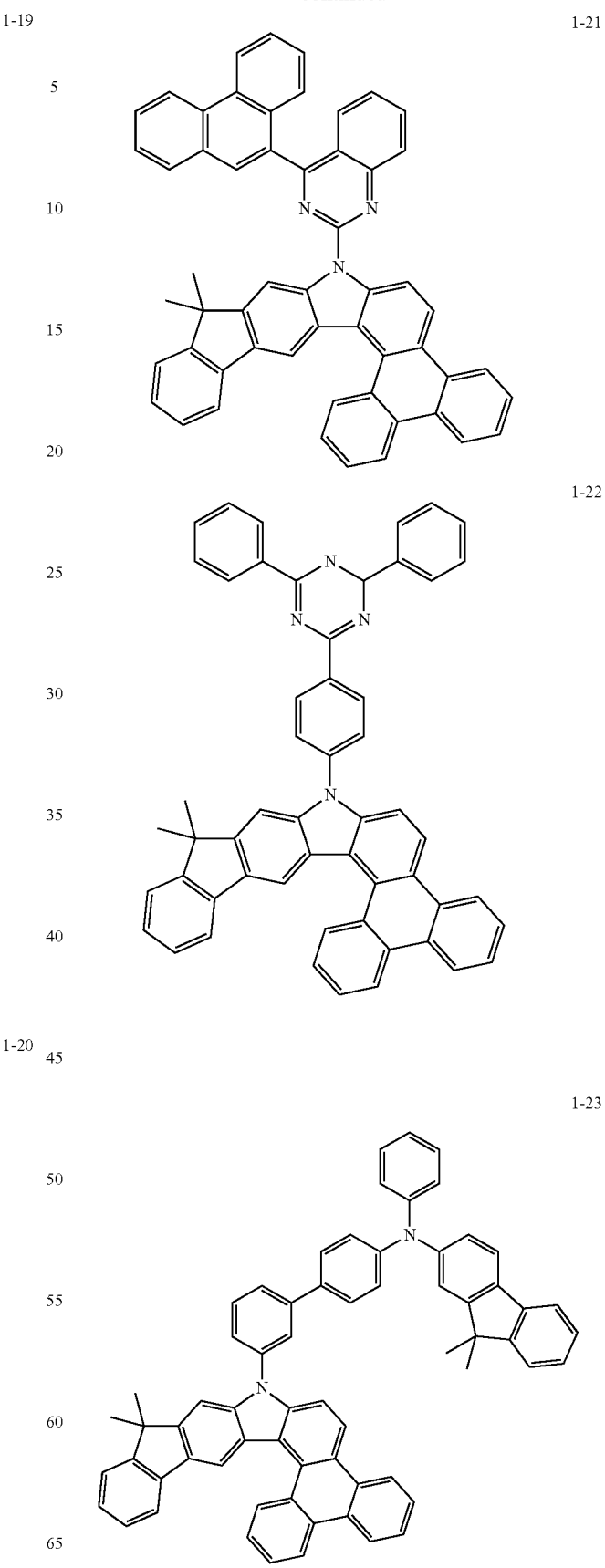

-continued
1-24
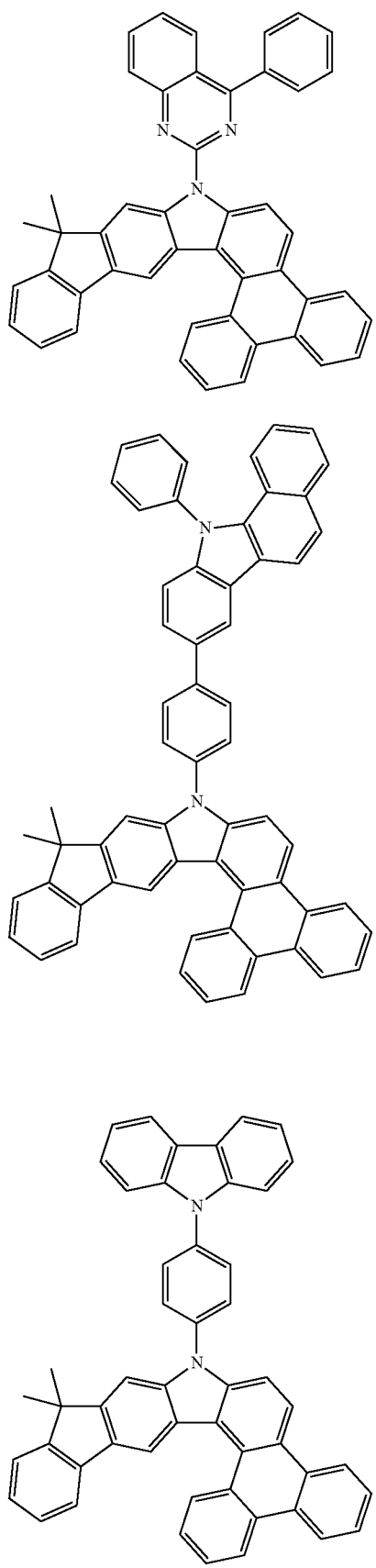
1-25
1-26
1-27
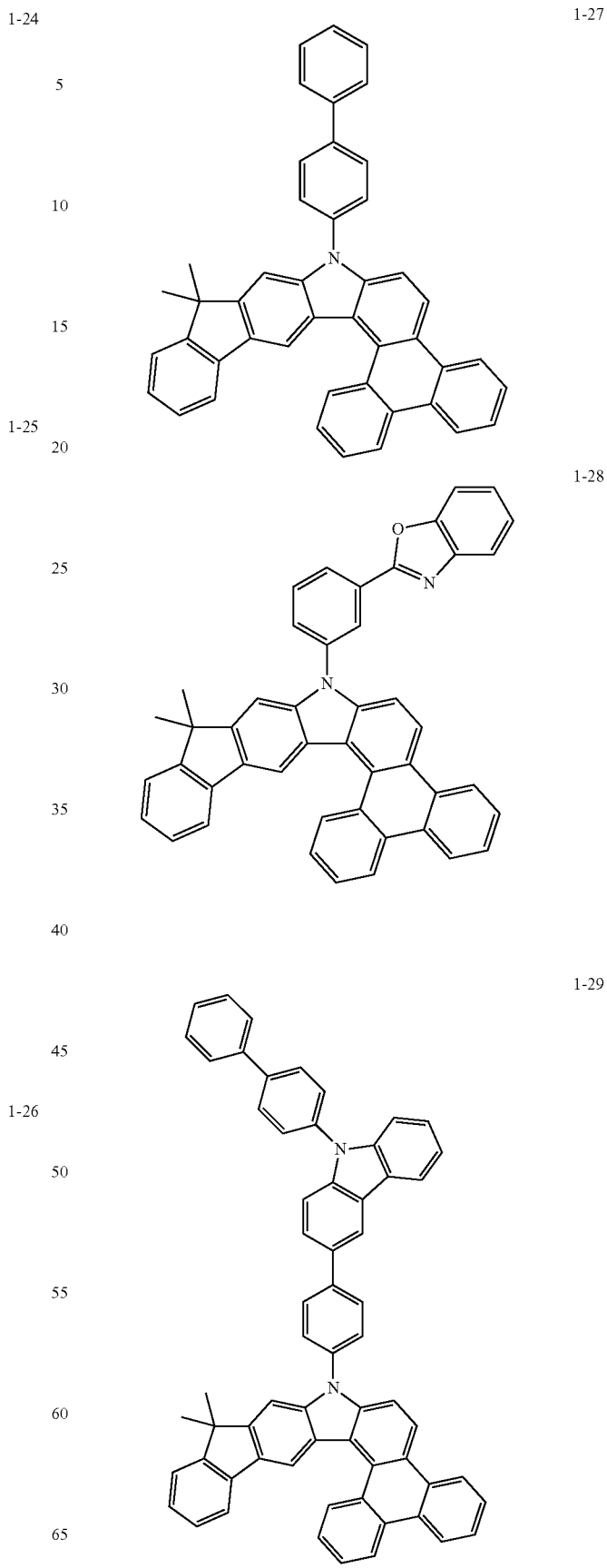
1-28
1-29

-continued
1-30
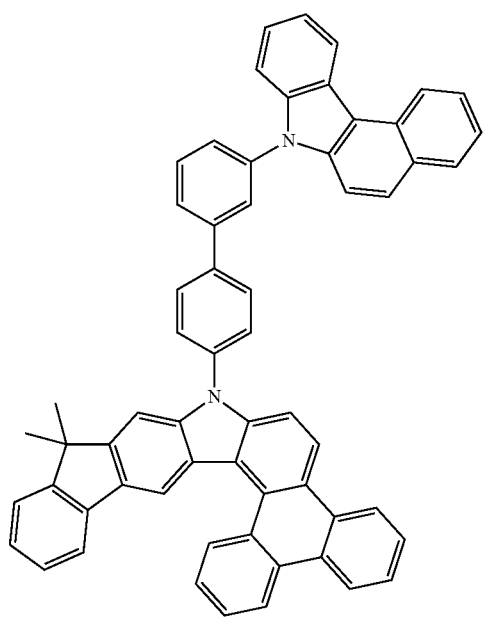
1-31
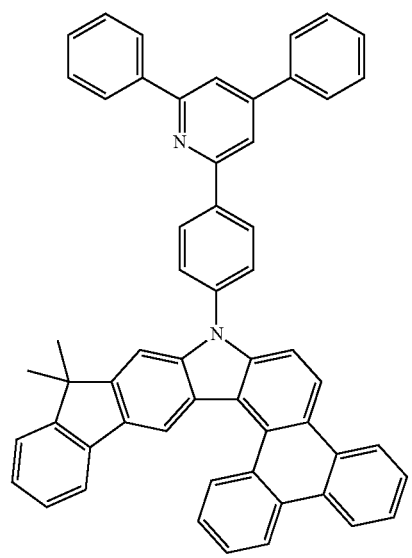
1-32
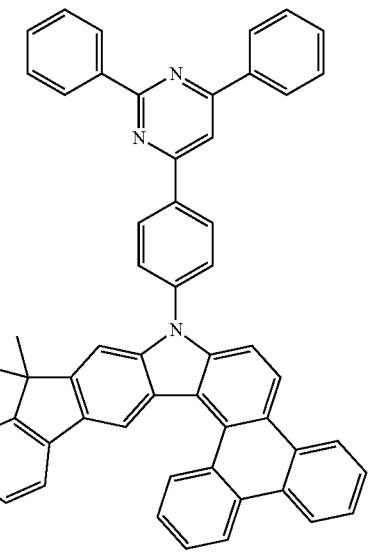
1-33
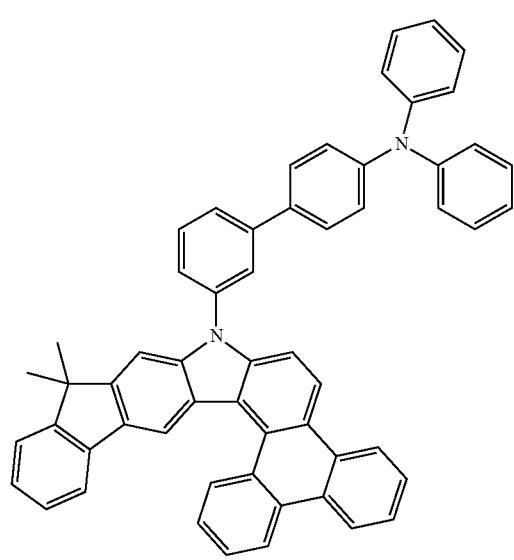
1-34
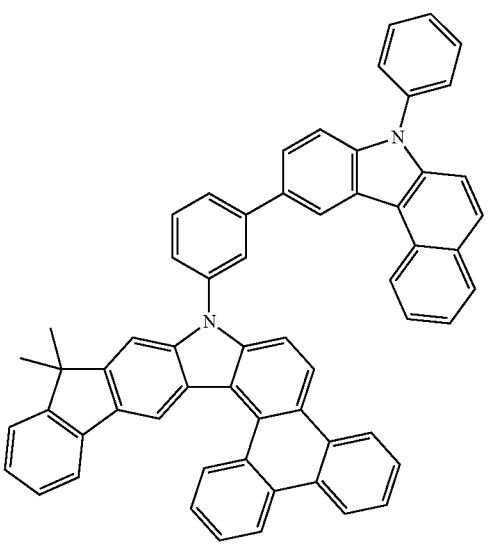

-continued
1-35
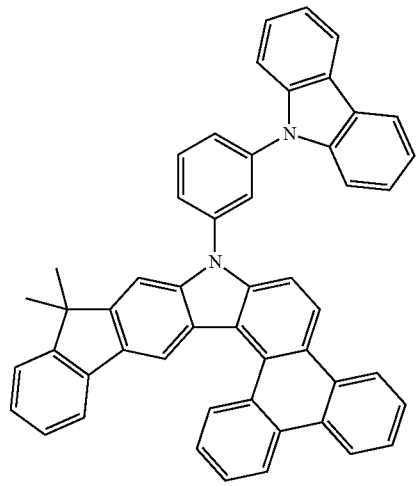
1-36
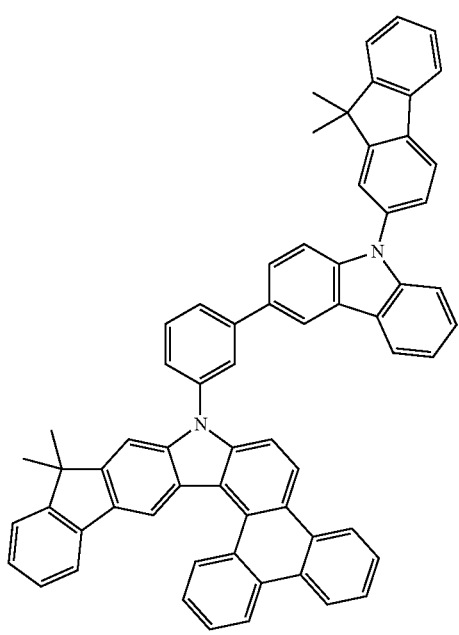
1-37
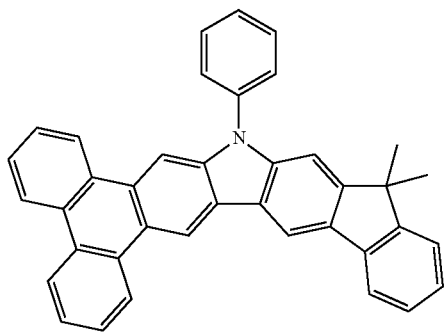
-continued
1-38
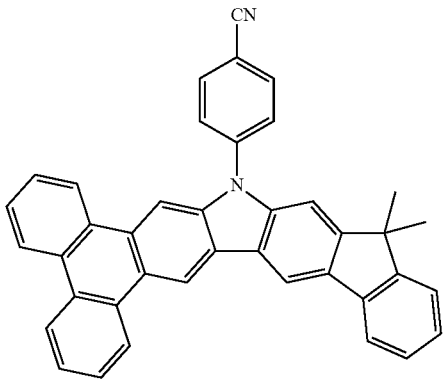
1-39
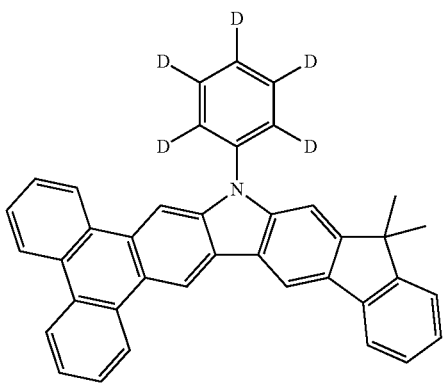
1-40
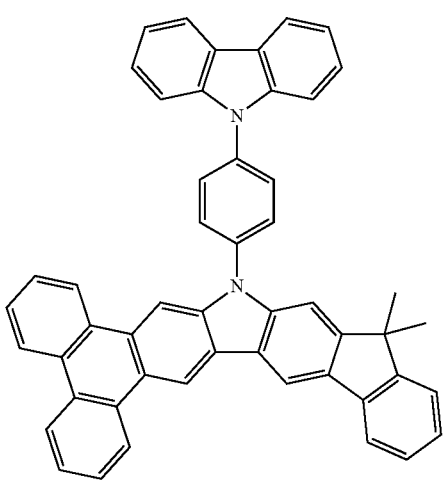

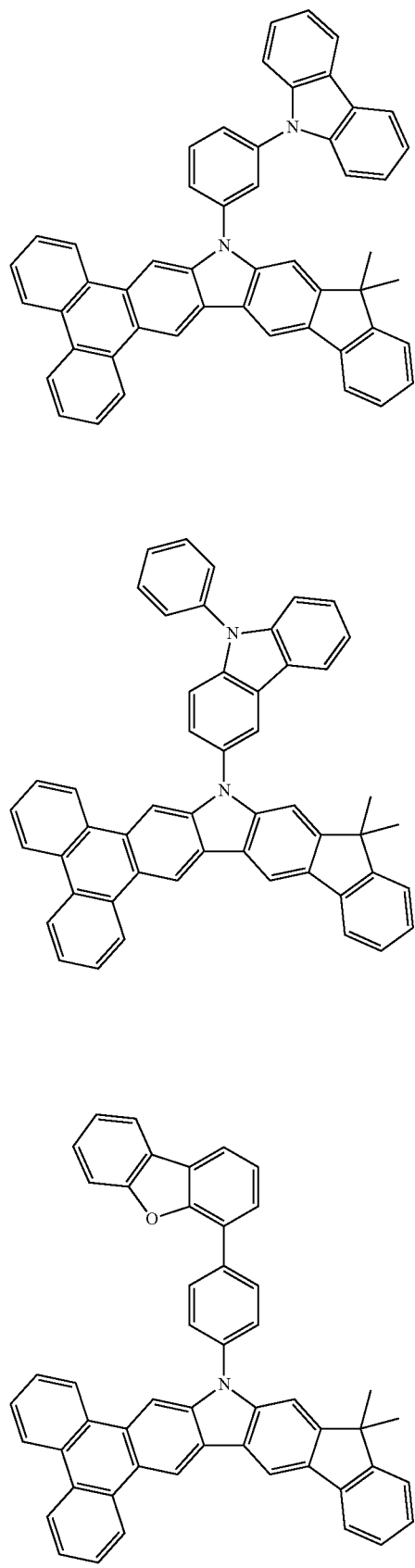
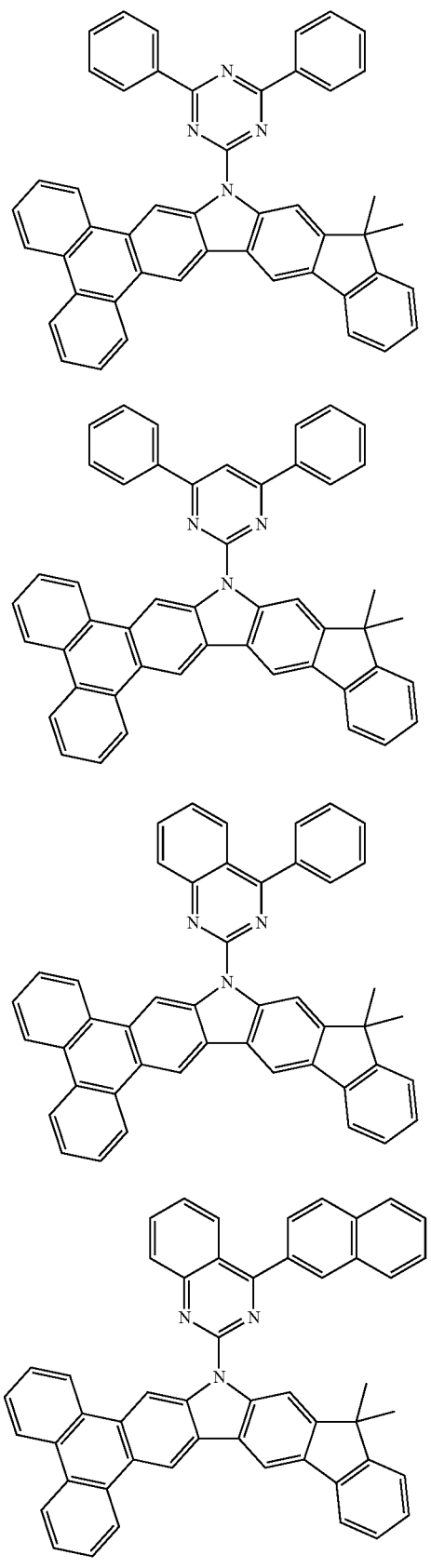

-continued
1-48
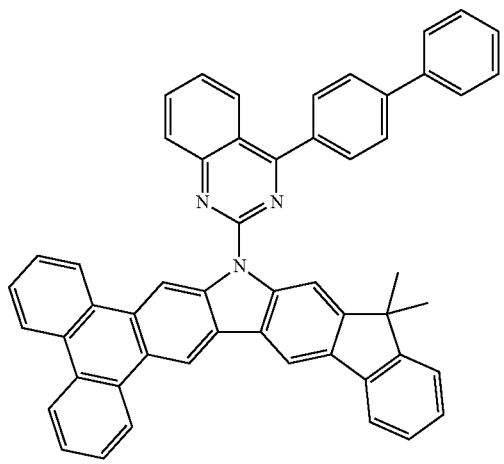
1-49
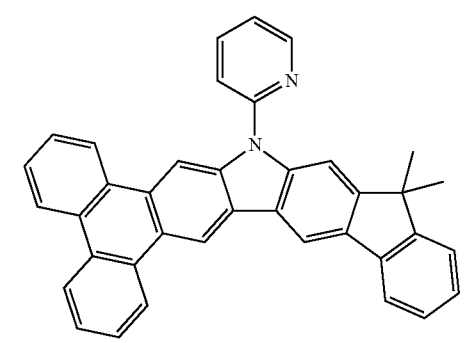
1-50
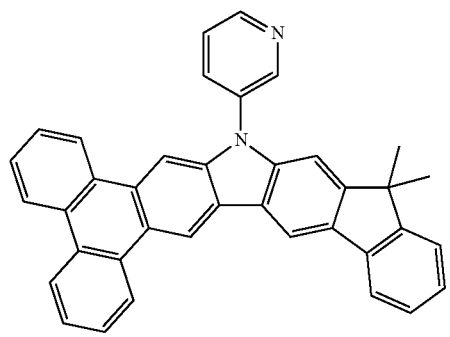
1-51
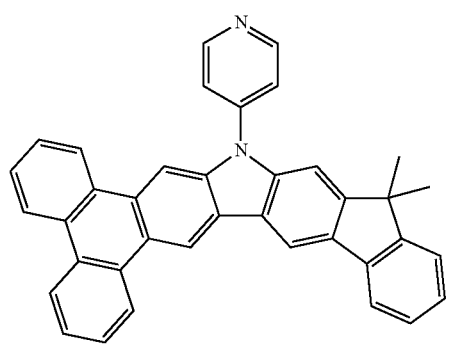
-continued
1-52
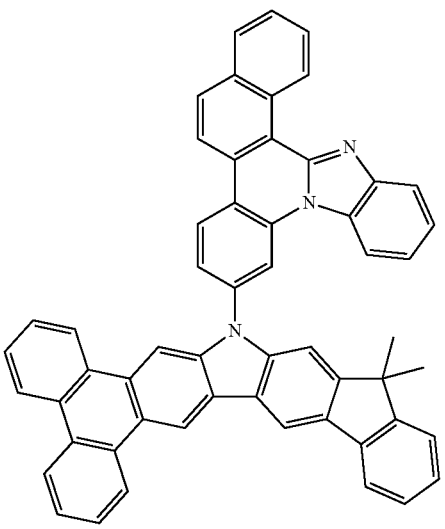
1-53
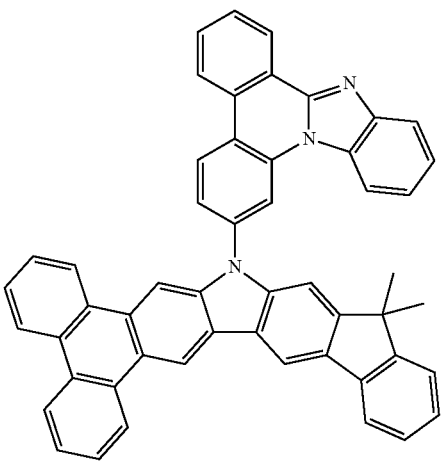
1-54
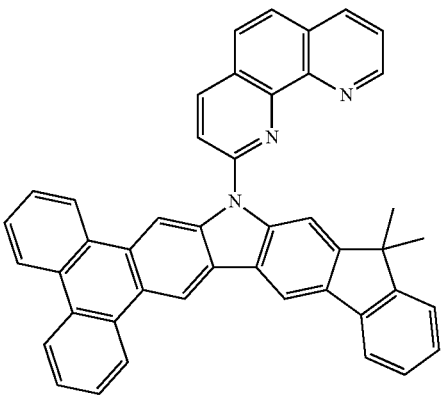

1-55
1-56
1-57
1-58
1-59
1-60
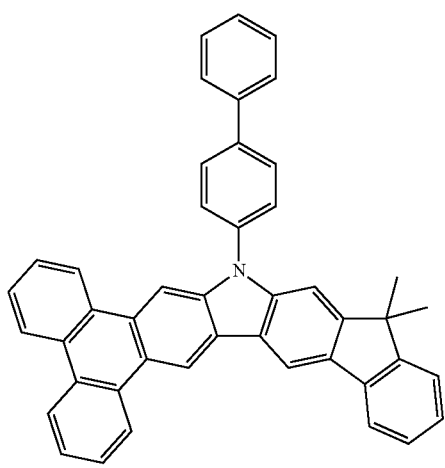
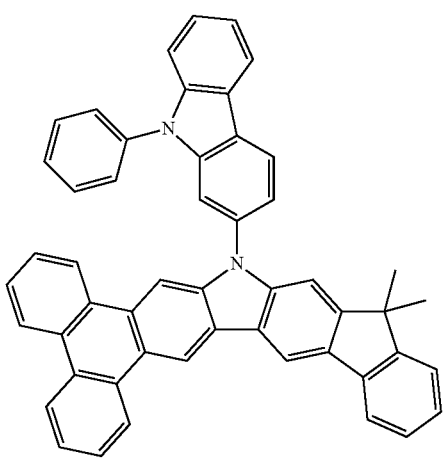

-continued
1-61
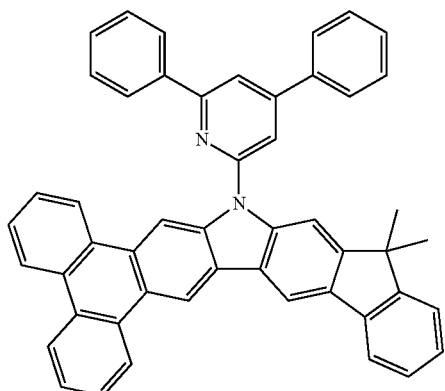
1-62
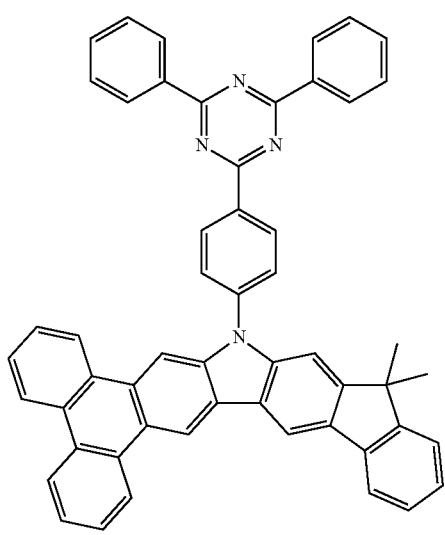
1-63
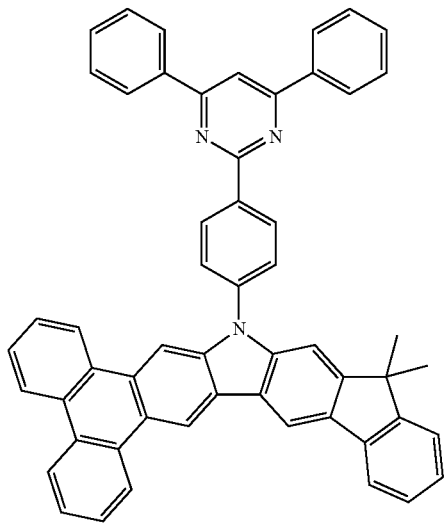
-continued
1-64
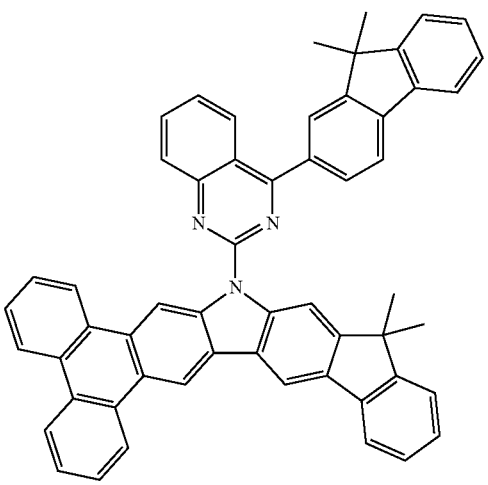
1-65
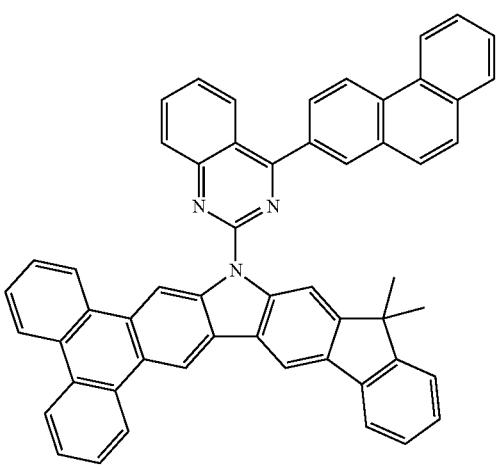
1-66
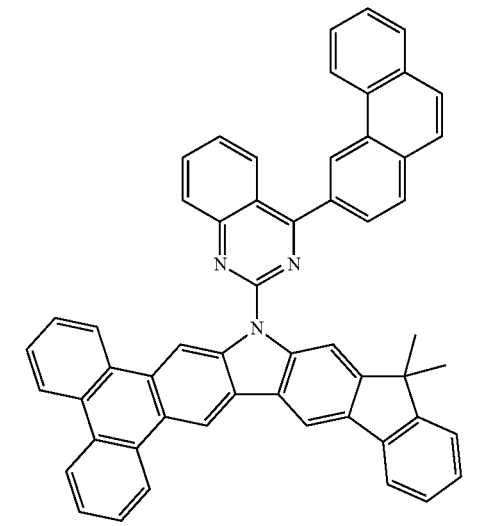

1-67
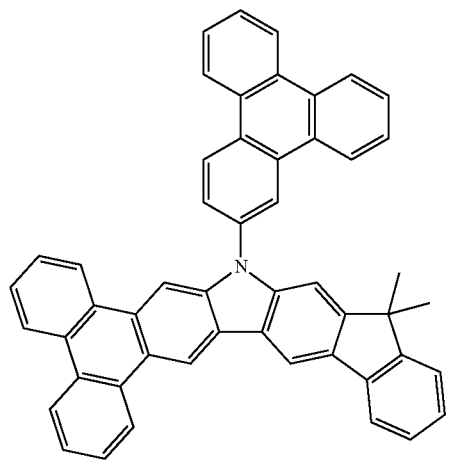
1-68
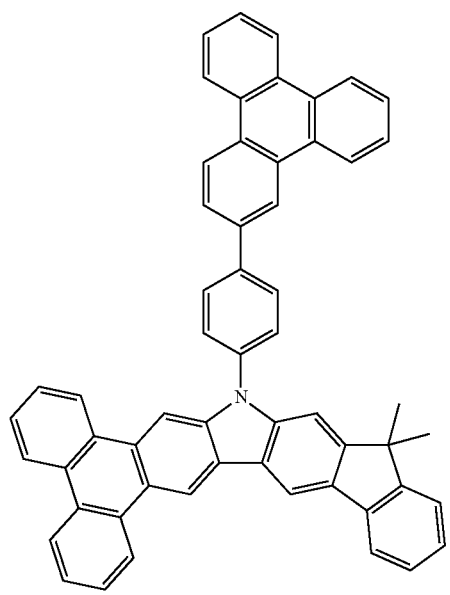
1-69
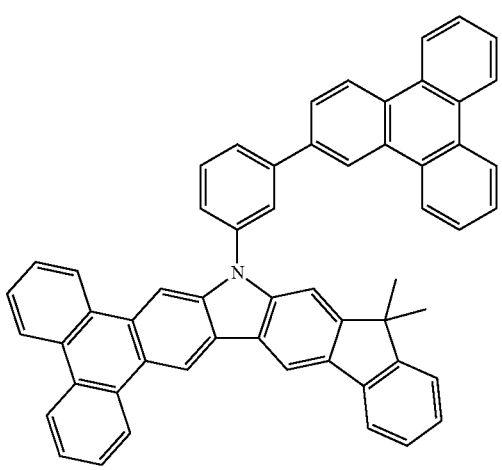
1-70
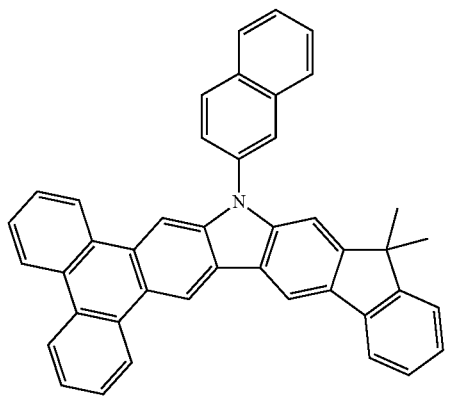
1-71
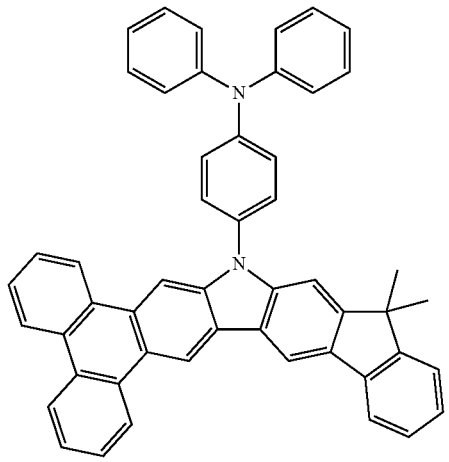
1-72
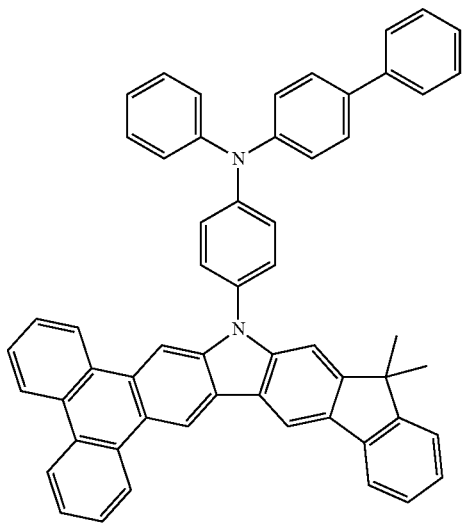

1-73
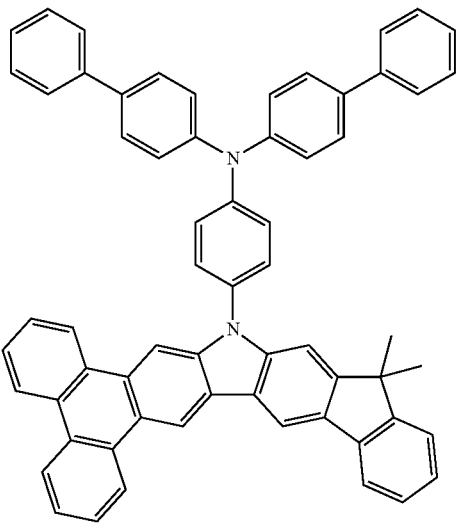
1-74
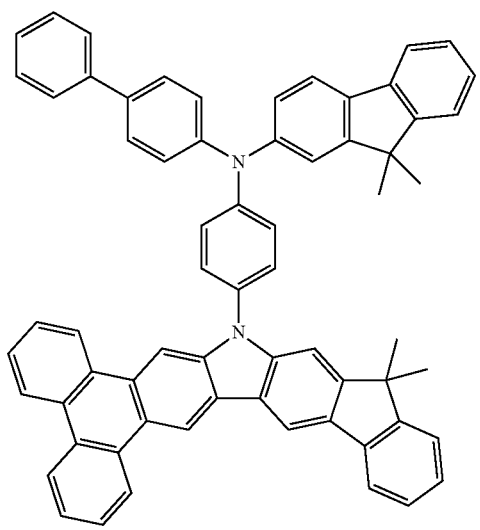
1-75
1-76
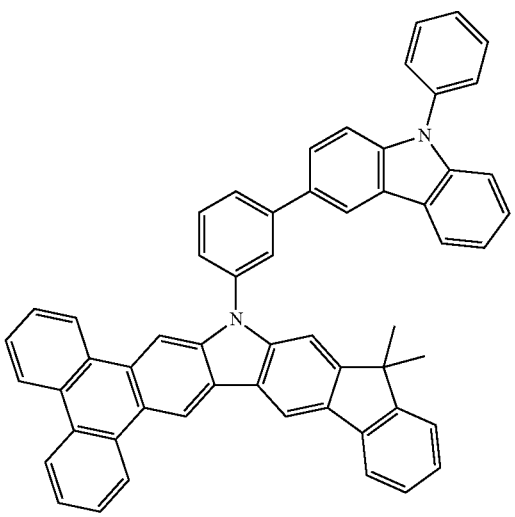
1-77
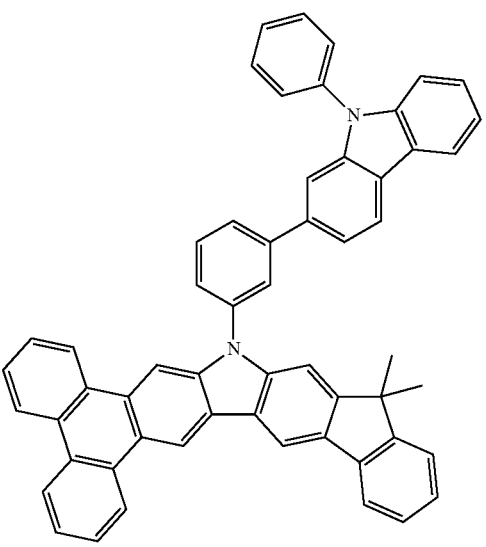
1-78
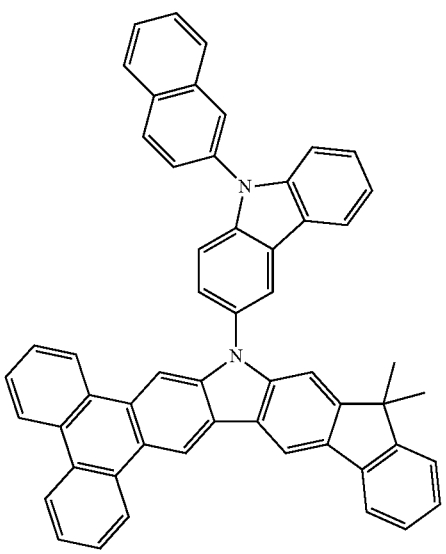

1-79
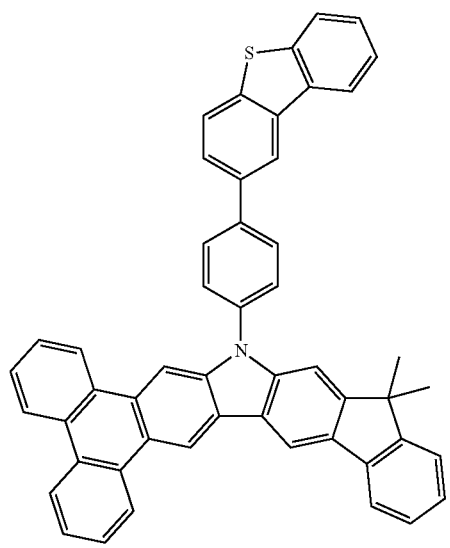
1-80
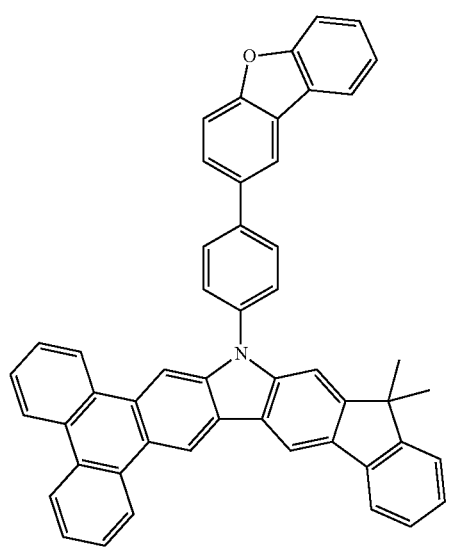
1-81
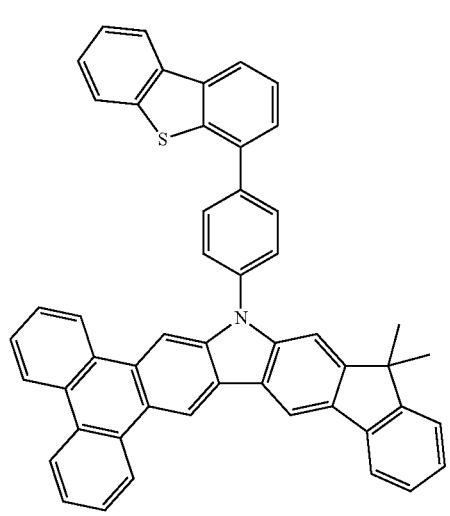
1-82
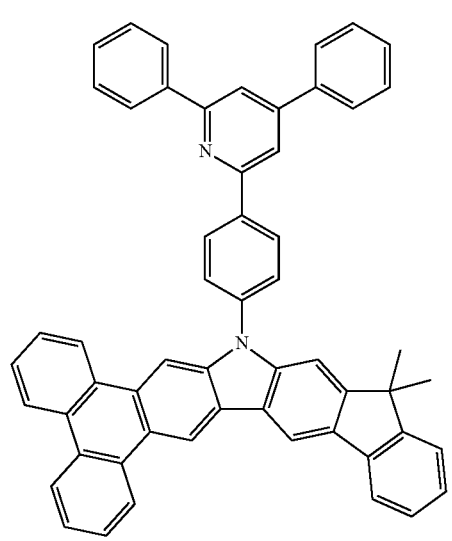
1-83
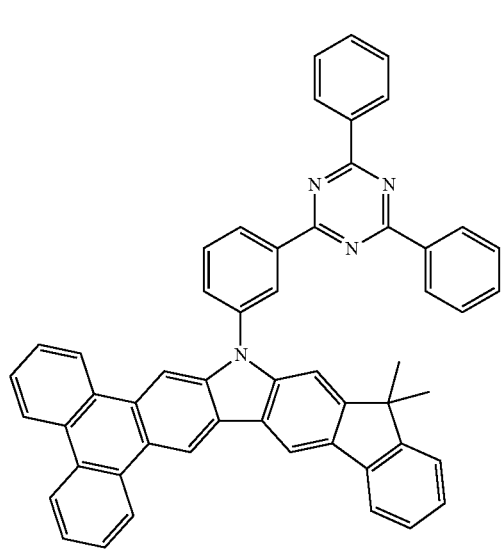
1-84
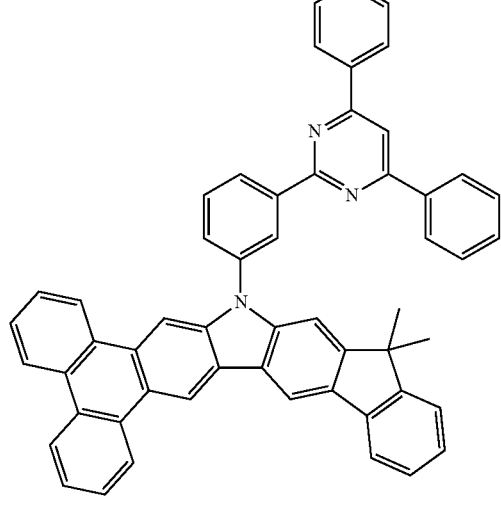

1-85
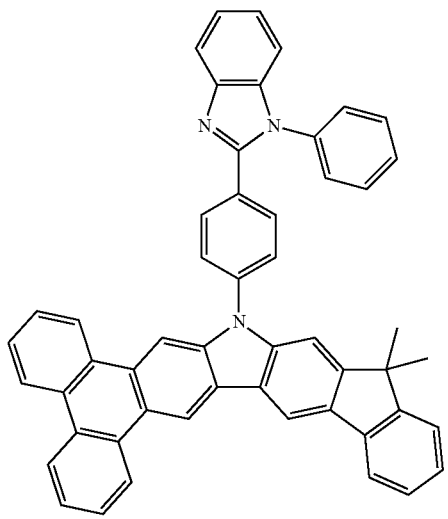
1-86
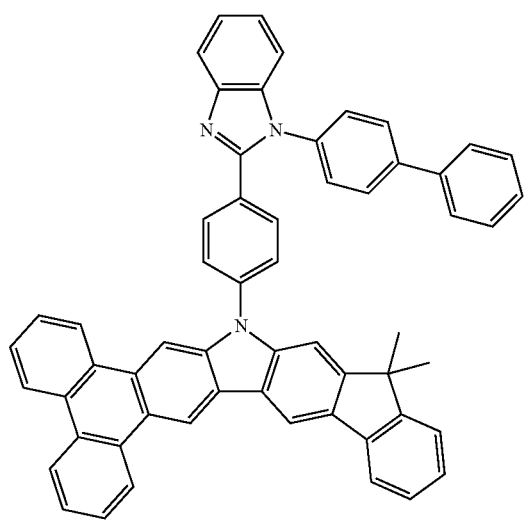
1-87
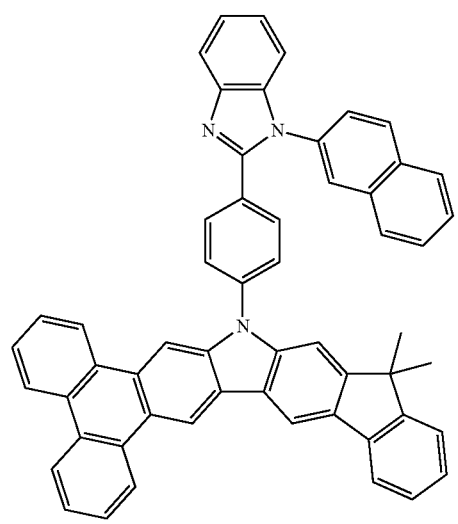
1-88
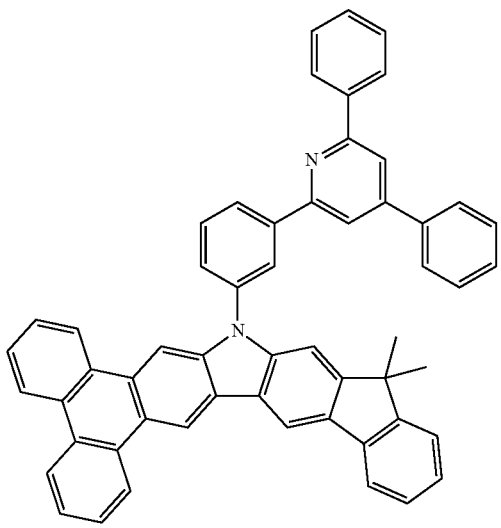
1-89
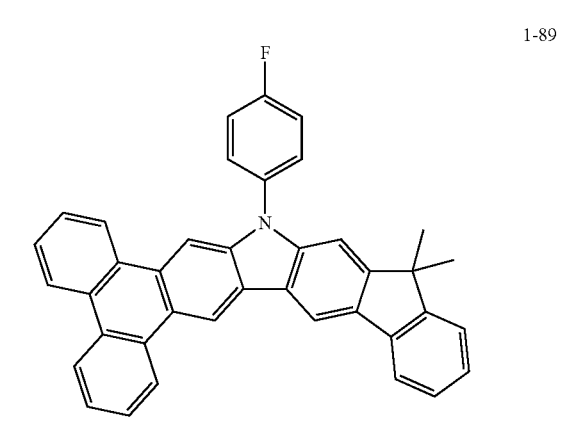
1-90
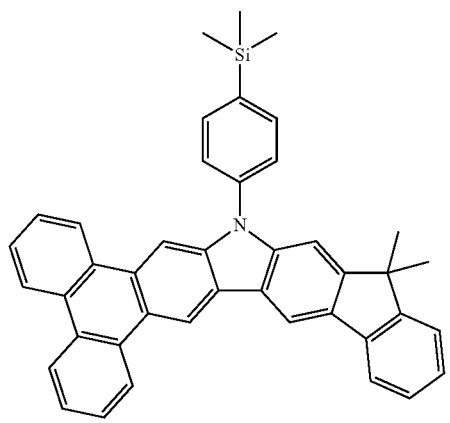

US 10,577,355 B2
1-91
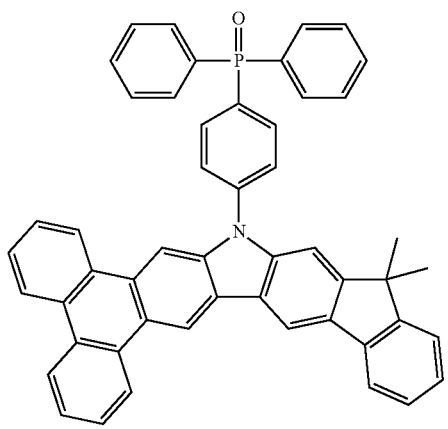
1-92
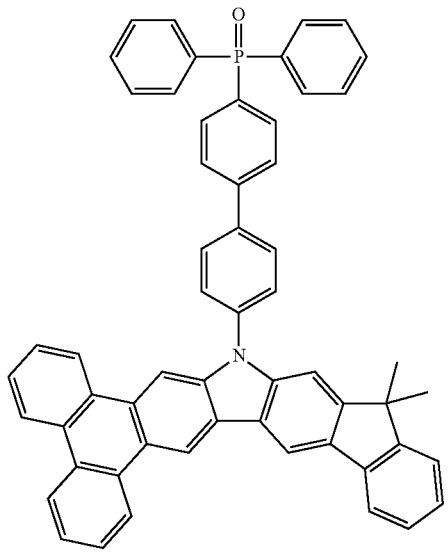
1-93
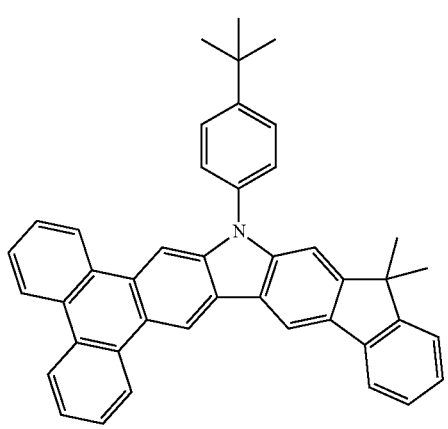
1-94
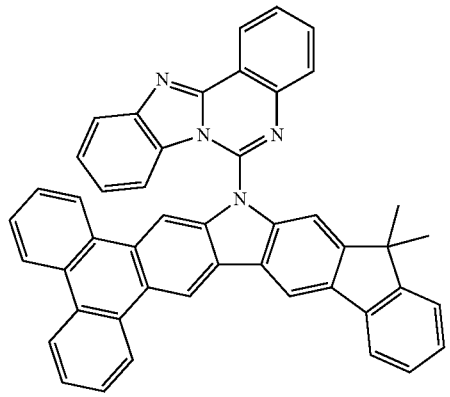
1-95
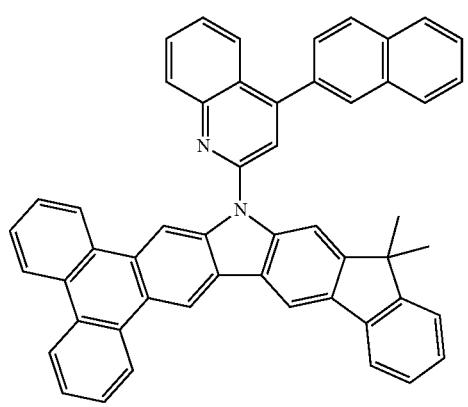
1-96
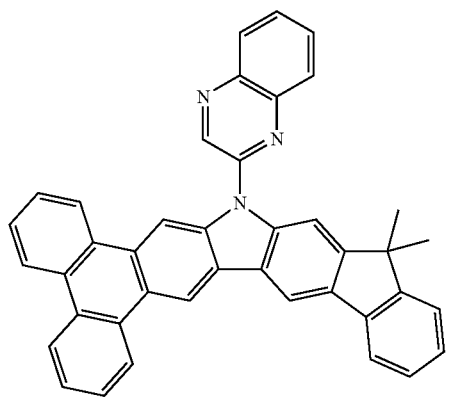

1-97

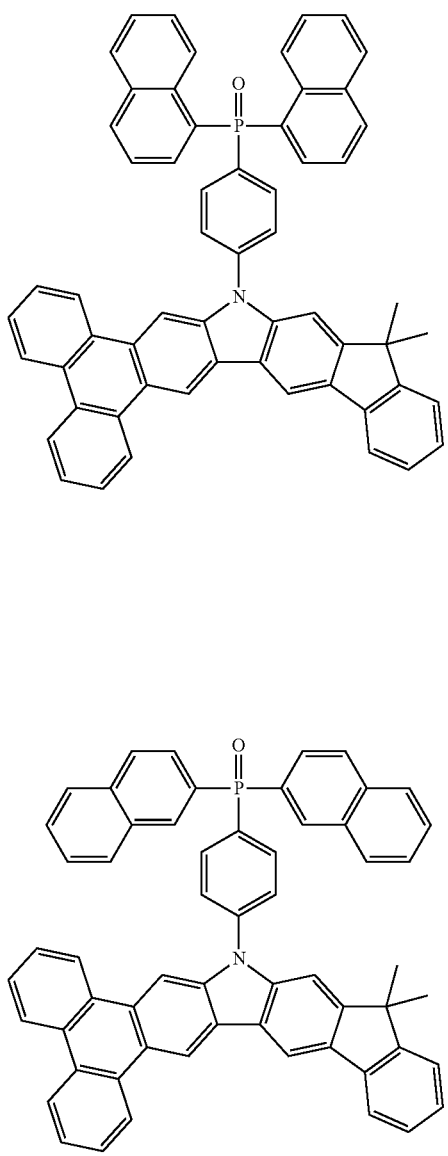

1-98

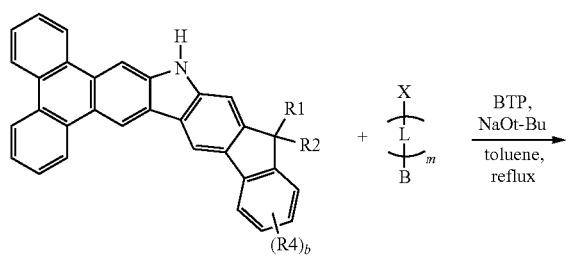

The compound represented by Chemical Formula 1 may be prepared based on preparation examples described below. According to one embodiment, the compound represented by Chemical Formula 1 may be prepared in the same manner as in the following Reaction Formula 1 or 2.

[Reaction Formula 1]

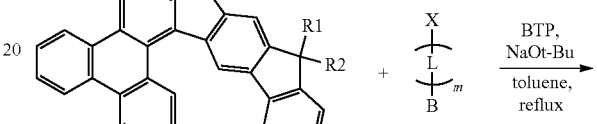

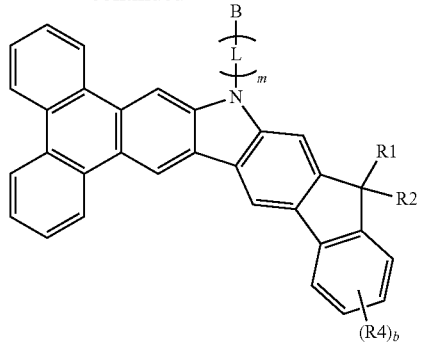

[Reaction Formula 2]

In Reaction Formulae 1 and 2, definitions of L, B, m, R1, R2, R4, and b are the same as in Chemical Formula 1, and X is a halogen group.

According to one embodiment of the present specification, the material represented by Chemical Formula 1 may be prepared through the steps described below as seen in Reaction Formula 1. Specifically, after the compound Core A and the compound of $X\text{-}(L)_m\text{-}B$ are dissolved in toluene under nitrogen atmosphere, a base and a palladium catalyst are added thereto and the result was stirred under reflux. When processing a Buchwald-Hartwig amination reaction as above, the reaction is complete after 5 hours to 10 hours, and the compound of Chemical Formula 1 may be prepared after column purification.

In addition, the present specification provides an organic light emitting device including the compound represented by Chemical Formula 1.

One embodiment of the present specification provides an organic light emitting device including a first electrode; a second electrode provided opposite to the first electrode; and one or more organic material layers provided between the first electrode and the second electrode, wherein one or more layers of the organic material layers include the compound of Chemical Formula 1.

The organic material layer of the organic light emitting device of the present specification may be formed in a monolayer structure, but may also be formed in a multilayer structure in which two or more organic material layers are laminated. For example, the organic light emitting device of the present invention may have a structure including a hole injection layer, a hole transfer layer, a light emitting layer, an electron transfer layer, an electron injection layer and the like as the organic material layer. However, the structure of the organic light emitting device is not limited thereto, and may include less numbers of organic material layers.

In one embodiment of the present specification, the organic material layer includes a hole injection layer; a hole transfer layer; or a layer carrying out hole injection and transfer at the same time, and at least one of the hole injection layer; the hole transfer layer; or the layer carrying out hole injection and transfer at the same time includes the compound of Chemical Formula 1.

In addition, in one embodiment of the present specification, the organic material layer includes a hole injection layer; a hole transfer layer; an electron blocking layer; or a layer carrying out hole injection and hole transfer at the same time, and at least one of the hole injection layer; the hole transfer layer; the electron blocking layer; or the layer carrying out hole injection and hole transfer at the same time includes the compound of Chemical Formula 1.

In another embodiment, the organic material layer includes a light emitting layer, and the light emitting layer includes the compound of Chemical Formula 1.

In one embodiment of the present specification, the organic material layer includes an electron transfer layer or an electron injection layer, and the electron transfer layer or the electron injection layer includes the compound of Chemical Formula 1.

In one embodiment of the present specification, the electron transfer layer, the electron injection layer or a layer carrying out electron transfer and electron injection at the same time includes the compound of Chemical Formula 1.

In another embodiment, the organic material layer includes a light emitting layer and an electron transfer layer, and the electron transfer layer includes the compound of Chemical Formula 1.

In another embodiment, the organic light emitting device may be an organic light emitting device having a structure in which an anode, one or more organic material layers and a cathode are laminated in consecutive order on a substrate (normal type).

In another embodiment, the organic light emitting device may be an organic light emitting device having a structure in which a cathode, one or more organic material layers and an anode are laminated in consecutive order on a substrate (inverted type).

For example, the structures of the organic light emitting device according to one embodiment of the present specification are illustrated in FIGS. 1 and 2.

FIG. 1 is a diagram showing an example of the organic light emitting device formed with a substrate (1), an anode (2), a light emitting layer (3) and a cathode (4). In such a structure, the compound may be included in the light emitting layer.

FIG. 2 is a diagram showing an example of the organic light emitting device formed with a substrate (1), an anode (2), a hole injection layer (5), a hole transfer layer (6), a light emitting layer (7), an electron transfer layer (8) and a cathode (4). In such a structure, the compound may be included in one or more layers of the hole injection layer, the hole transfer layer, the light emitting layer and the electron transfer layer.

The organic light emitting device of the present specification may be manufactured using materials and methods known in the art, except that one or more layers of organic material layers include the compound of the present specification, that is, the compound of Chemical Formula 1.

When the organic light emitting device includes a plurality of organic material layers, the organic material layers may be formed with the same material or with different materials.

One embodiment of the present specification provides an organic light emitting device including a first electrode; a second electrode provided opposite to the first electrode; a light emitting layer provided between the first electrode and the second electrode; and two or more organic material layers provided between the light emitting layer and the first electrode, or between the light emitting layer and the second electrode, wherein at least one of the two or more organic material layers includes the heterocyclic compound. In one embodiment, two or more from the group consisting of an electron transfer layer, an electron injection layer, a layer carrying out electron transfer and electron injection at the same time, and a hole blocking layer may be selected as the two or more organic material layers.

In one embodiment of the present specification, the organic material layer includes two or more electron transfer layers, and at least one of the two or more electron transfer layers includes the heterocyclic compound. Specifically, in one embodiment of the present specification, the heterocyclic compound may be either included in one of the two or more electron transfer layers, or included in each of the two or more electron transfer layers.

In addition, in one embodiment of the present specification, when the heterocyclic compound is included in each of the two or more electron transfer layers, materials other than the heterocyclic compound may be the same as or different from each other.

The organic light emitting device of the present specification may be manufactured using materials and methods known in the art, except that one or more layers of the organic material layers include the compound of Chemical Formula 1, that is, the compound represented by Chemical Formula 1.

For example, the organic light emitting device of the present specification may be manufactured by consecutively laminating a first electrode, an organic material layer and a second electrode on a substrate. Herein, the organic light emitting device may be manufactured by forming an anode on the substrate by depositing a metal, a metal oxide having conductivity, or alloys thereof using a physical vapor deposition (PVD) method such as a sputtering method or an e-beam evaporation method, forming the organic material layer including a hole injection layer, a hole transfer layer, a light emitting layer and an electron transfer layer thereon, and then depositing a material capable of being used as a cathode thereon. In addition to this method, the organic light emitting device may also be manufactured by consecutively depositing a cathode material, an organic material layer and an anode material on a substrate.

In addition, when manufacturing the organic light emitting device, the compound of Chemical Formula 1 may be formed as the organic material layer using a solution coating method as well as a vacuum deposition method. Herein, the solution coating method means spin coating, dip coating, doctor blading, ink jet printing, screen printing, a spray method, roll coating and the like, but is not limited thereto.

In addition to this method, the organic light emitting device may also be manufactured by consecutively depositing a cathode material, an organic material layer and an anode material on a substrate (International Patent Application Laid-Open Publication No. 2003/012890). However, the manufacturing method is not limited thereto.

In one embodiment of the present specification, the first electrode is an anode, and the second electrode is a cathode.

In another embodiment, the first electrode is a cathode, and the second electrode is an anode.

As the anode material, a material having large work function is normally preferable so that hole injection to the organic material layer is smooth. Specific examples of the anode material capable of being used in the present invention include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as $ZnO:Al$ or $SnO_2:Sb$; conductive polymers such as poly(3-methylthiophene), poly[3,4-(ethylen-1,2-dioxy)thiophene] (PEDOT), polypyrrole and polyaniline, and the like, but are not limited thereto.

As the cathode material, a material having small work function is normally preferable so that electron injection to the organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an anode material and the HOMO of surrounding organic material layers. Specific examples of the hole injection material include a metal porphyrin, oligothiophene, an arylamine-based organic material, a hexanitrile hexazatriphenylene-based organic material, a quinacridone-based organic material, a perylene-based organic material, anthraquinone, and a polyaniline- and a polythiophene-based conductive polymer, and the like, but are not limited thereto.

The hole transfer layer is a layer that receives holes from a hole injection layer and transfers the holes to a light emitting layer, and as the hole transfer material, a material capable of receiving holes from an anode or a hole injection layer, moving the holes to a light emitting layer, and having high mobility for the holes, is suitable. Specific examples thereof include an arylamine-based organic material, a conductive polymer, a block copolymer having conjugated parts and non-conjugated parts together, and the like, but are not limited thereto.

The light emitting material is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include a 8-hydroxy-quinoline aluminum complex ($Alq_3$); a carbazole-based compound; a dimerized styryl compound; BAlq; a 10-hydroxybenzo quinoline-metal compound; a benzoxazole-, a benzthiazole- and a benzimidazole-based compound; a poly(p-phenylenevinylene) (PPV)-based polymer; a spiro compound; polyfluorene, rubrene, and the like, but are not limited thereto.

The light emitting layer may include a host material and a dopant material. The host material includes a fused aromatic ring derivative, a heteroring-containing compound or the like. Specifically, the fused aromatic ring derivative includes an anthracene derivative, a pyrene derivative, a naphthalene derivative, a pentacene derivative, a phenanthrene compound, a fluoranthene compound and the like, and the heteroring-containing compound includes a carbazole derivative, a dibenzofuran derivative, a ladder-type furan compound, a pyrimidine derivative and the like, but the material is not limited thereto.

The dopant material includes an aromatic amine derivative, a styrylamine compound, a boron complex, a fluoranthene compound, a metal complex and the like. Specifically, the aromatic amine derivative is a fused aromatic ring derivative having a substituted or unsubstituted arylamino group and includes arylamino group-including pyrene, anthracene, crycene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamino group are substituted or unsubstituted. Specifically, styrylamine, styryldiamine, styryltriamine, styryltetramine or the like is included, but the styrylamine compound is not limited thereto. In addition, the metal complex includes an iridium complex, a platinum complex or the like, but is not limited thereto.

The electron transfer layer is a layer that receives electrons from an electron injection layer and transfers the electrons to a light emitting layer, and as the electron transfer material, a material capable of favorably receiving electrons from a cathode, moving the electrons to a light emitting layer, and having high mobility for the electrons, is suitable. Specific examples thereof include an Al complex of 8-hydroxyquinoline; a complex including $Alq_3$; an organic radical compound; a hydroxyflavon-metal complex and the like, but are not limited thereto. The electron transfer layer may be used together with any desired cathode material as used according to existing technologies. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, a metal complex compound, a nitrogen-containing 5-membered ring derivative, and the like, but are not limited thereto.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8- hydroxyquinolinato)aluminum, tris(8-hydroxyquinolinato) gallium, bis(10-hydroxybenzo[h]quinolinato)berylium, bis (10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato) (1-naphtholato)aluminum, bis(2-methyl-8-quinolinato) (2-naphtholato)gallium and the like, but is not limited thereto.

The organic light emitting device according to the present specification may be a top-emission type, a bottom-emission type or a dual-emission type depending on the materials used.

In one embodiment of the present specification, the compound of Chemical Formula 1 may be included in an organic solar cell or an organic transistor in addition to an organic light emitting device.

The preparation of the compound represented by Chemical Formula 1 and the organic light emitting device including the compound will be described in detail in the following examples. However, the following examples are for illustrative purposes only, and the scope of the present specification is not limited thereto.

PREPARATION EXAMPLE

Synthesis of Core B

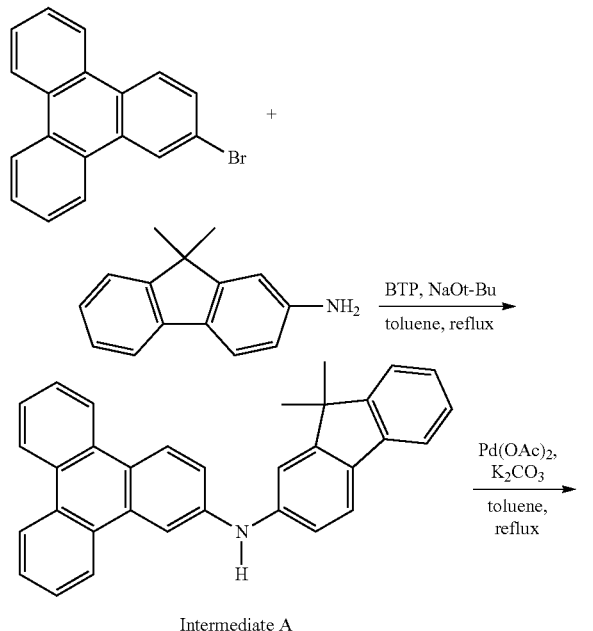

Core B

Under nitrogen atmosphere, after completely dissolving 2-bromotriphenylene (30 g, 98 mmol) and 2-amino-9,9-dimethylfluorene (20.5 g, 98 mmol) in 200 ml of toluene, NaOt-Bu (11.3 g, 117.6 mmol) was added thereto, and the result was stirred while raising a temperature until reflux. When the result started to reflux, bis(tri-tert-butylphosphine) palladium(0) (0.5 g, 0.98 mmol) was slowly added dropwise thereto. The reaction was complete after 3 hours and the result was cooled to room temperature, concentrated under reduced pressure, and then column purified to prepare 31.9 g of Intermediate A.

MS[M+H]+=436

Intermediate A (31.9 g, 73.3 mmol) and potassium carbonate (10.1 g, 73.3 mmol) were placed in 146 ml of pivalic acid. The result was heated to 120° C., palladium acetate (0.99 g, 4.4 mmol) was added thereto, and then the result was stirred under oxygen atmosphere. The reaction was complete after 48 hours and the result was cooled to room temperature, concentrated under reduced pressure, and then column purified to prepare 9.5 g of Core B.

MS[M+H]+=434

Synthesis of Compound 1

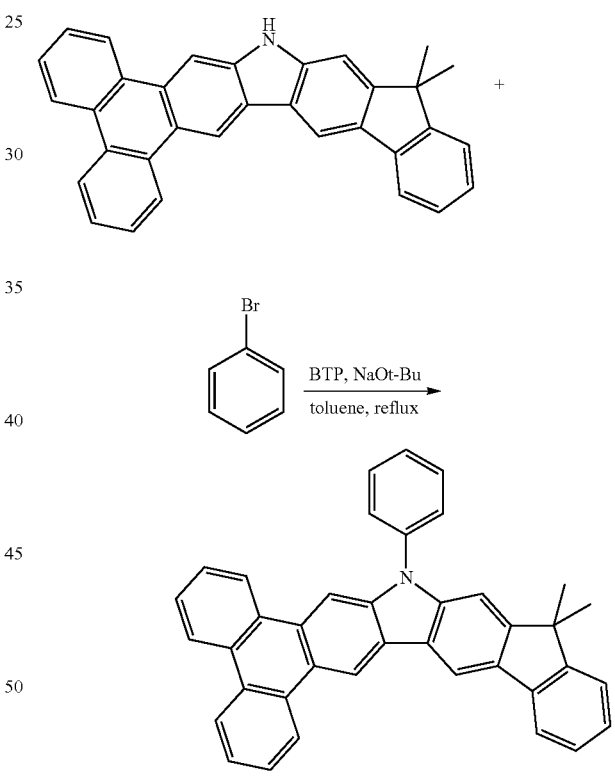

Compound 1

After adding Core B (5 g, 11.5 mmol), bromobenzene (1.8 g, 11.5 mmol) and NaOt-Bu (1.3 g, 13.8 mmol) in 30 ml of toluene, the temperature was raised while stirring the result. After the temperature was raised and the result started to reflux, bis(tri-tert-butylphosphine)palladium (0.11 g, 0.23 mmol) was slowly added dropwise thereto. The reaction was complete after 5 hours and the result was cooled to room temperature, concentrated under reduced pressure, and then column purified to prepare 5.27 g of Compound 1.

MS[M+H]+=510

Synthesis of Compound 2

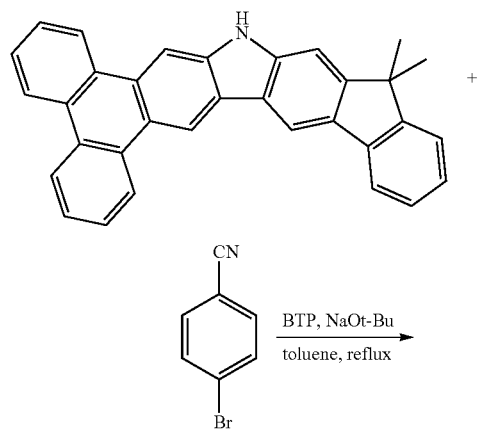

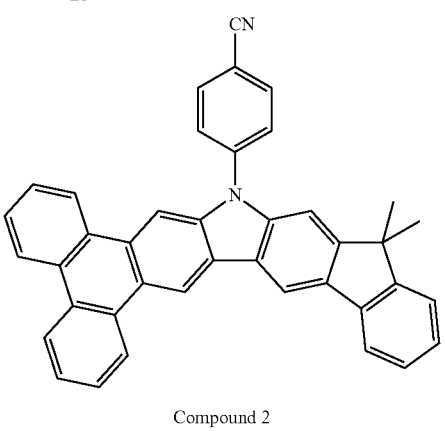
Compound 2

4.9 g of Compound 2 was prepared in the same manner as in the synthesis of Compound 1 except that Core B (5 g, 11.5 mmol) and para-bromobenzonitrile (2.09 g, 11.5 mmol) were used.

MS[M+H]+=535

Synthesis of Compound 3

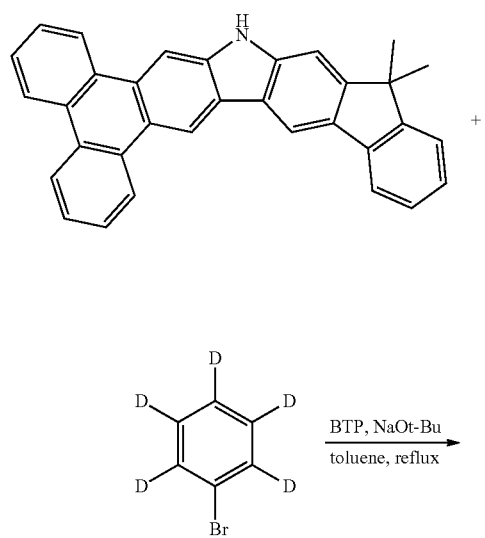

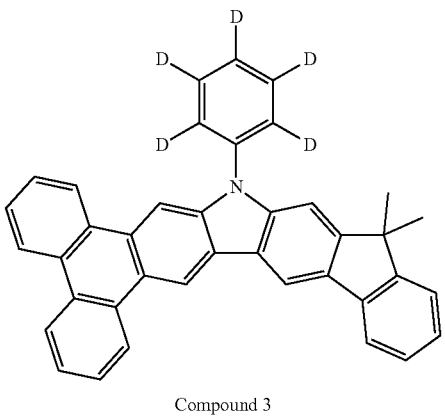
Compound 3

5.0 g of Compound 3 was prepared in the same manner as in the synthesis of Compound 1 except that Core B (5 g, 11.5 mmol) and bromobenzene-d5 (1.86 g, 11.5 mmol) were used.

MS[M+H]+=515

Synthesis of Compound 4

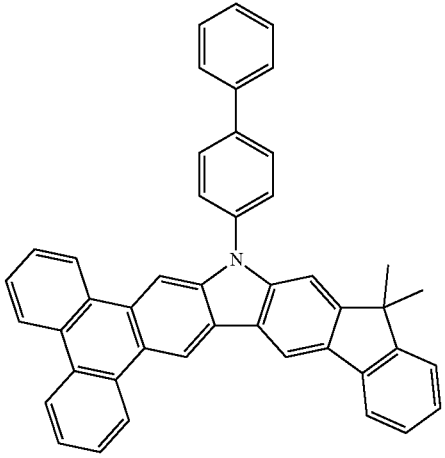
Compound 4

6.1 g of Compound 4 was prepared in the same manner as in the synthesis of Compound 1 except that Core B (5 g, 11.5 mmol) and 4-bromo-1,1-biphenyl (2.68 g, 11.5 mmol) were used.

MS[M+H]+=586

Synthesis of Compound 5

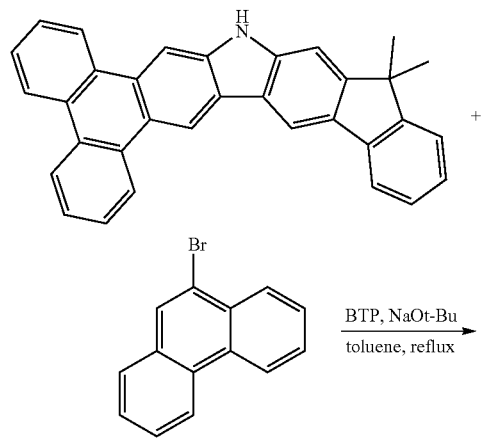

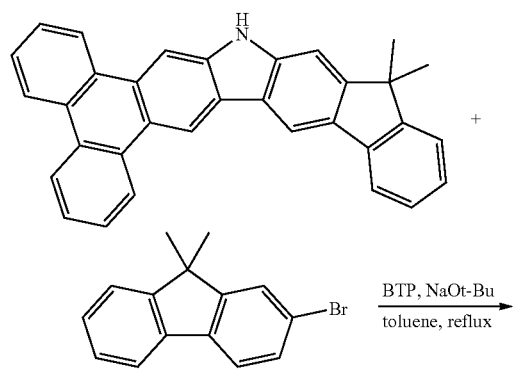

Compound 5

6.0 g of Compound 5 was prepared in the same manner as in the synthesis of Compound 1 except that Core B (5 g, 11.5 mmol) and 9-bromophenanthrene (2.94 g, 11.5 mmol) were used.

MS[M+H]+=610

Synthesis of Compound 6

-continued

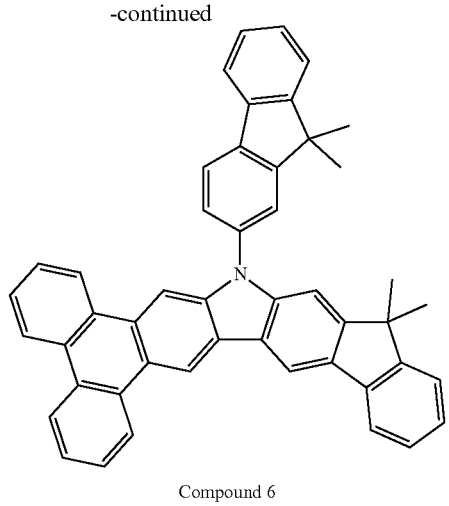

Compound 6

6.5 g of Compound 6 was prepared in the same manner as in the synthesis of Compound 1 except that Core B (5 g, 11.5 mmol) and 2-bromo-9,9-dimethyl-9H-fluorene (3.13 g, 11.5 mmol) were used.

MS[M+H]+=626

Synthesis of Compound 7

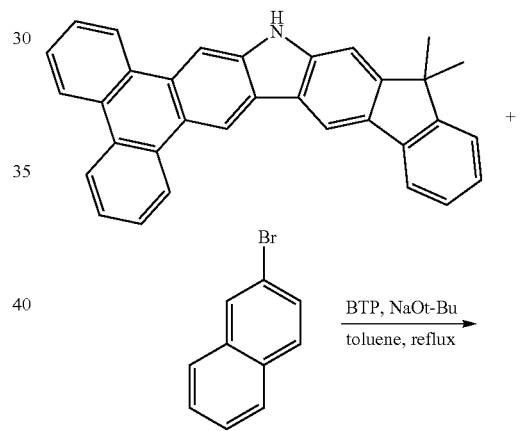

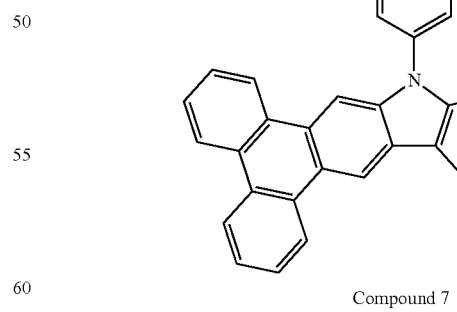

Compound 7

5.8 g of Compound 7 was prepared in the same manner as in the synthesis of Compound 1 except that Core B (5 g, 11.5 mmol) and 2-bromonaphthalene (2.37 g, 11.5 mmol) were used.

MS[M+H]+=560

Synthesis of Compound 8

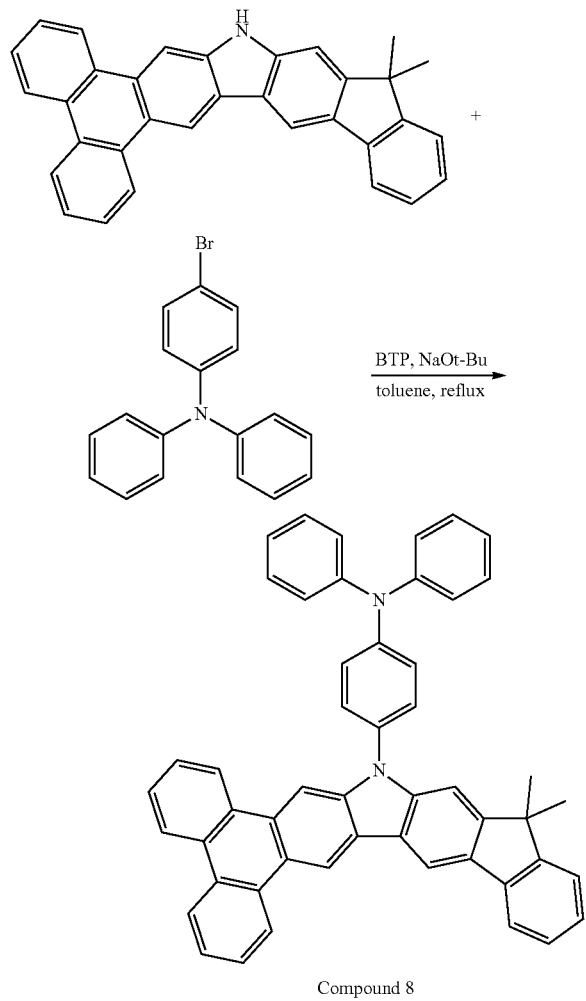

Compound 8

After adding Core B (5 g, 11.5 mmol), 4-bromo-N,N-diphenylaniline (3.71 g, 11.5 mmol) and NaOt-Bu (1.3 g, 13.8 mmol) in 40 ml of toluene, the temperature was raised while stirring the result. After the temperature was raised and the result started to reflux, bis(tri-tertbutylphosphine) palladium (0.11 g, 0.23 mmol) was slowly added dropwise thereto. The reaction was complete after 7 hours and the result was cooled to room temperature, concentrated under reduced pressure, and then column purified to prepare 6.7 g of Compound 8.

MS[M+H]+=677

Synthesis of Compound 9

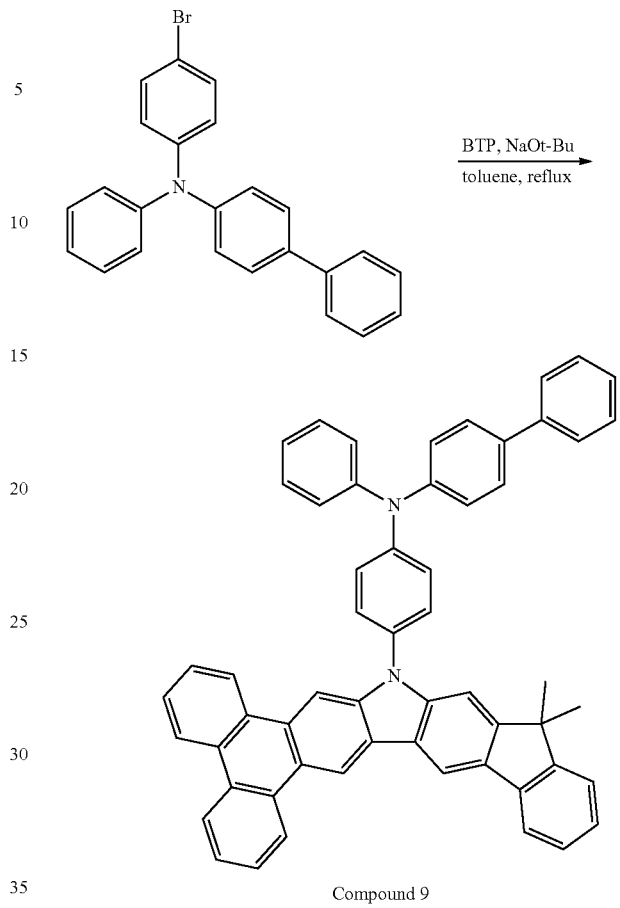

Compound 9

7.4 g of Compound 9 was prepared in the same manner as in the synthesis of Compound 8 except that Core B (5 g, 11.5 mmol) and N-(4-bromophenyl)-N-phenyl-[1,1-biphenyl]-4-amine (3.71 g, 11.5 mmol) were used.

MS[M+H]+=753

Synthesis of Compound 10

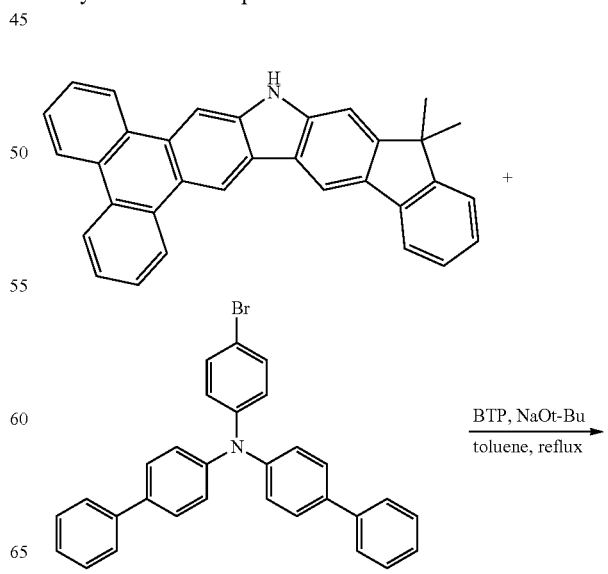

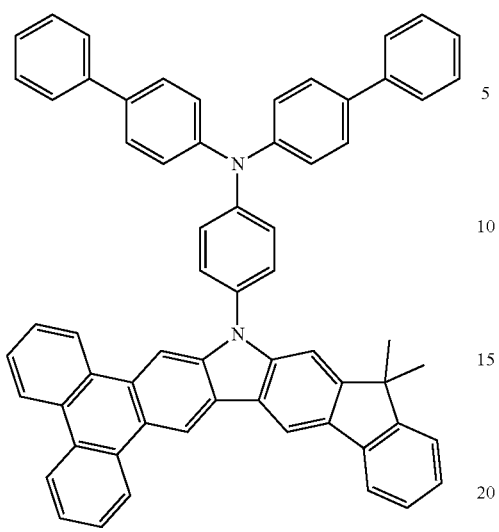

Compound 10

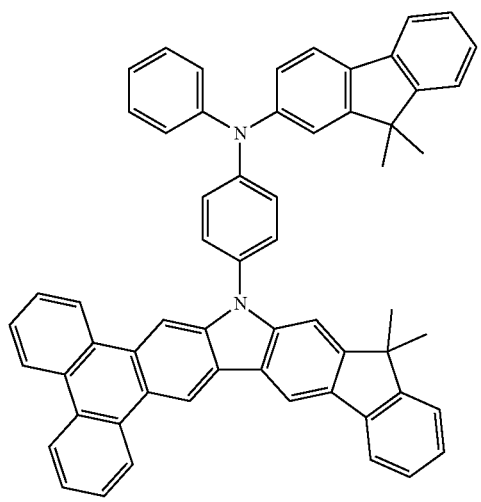

Compound 11

7.6 g of Compound 10 was prepared in the same manner as in the synthesis of Compound 8 except that Core B (5 g, 11.5 mmol) and N-([1,1-biphenyl]-4-yl)-N-(4-bromophenyl)-[1,1-biphenyl]-4-amine (5.46 g, 11.5 mmol) were used.

MS[M+H]+=829

Synthesis of Compound 11

7.8 g of Compound 11 was prepared in the same manner as in the synthesis of Compound 8 except that Core B (5 g, 11.5 mmol) and N-(4-bromophenyl)-9,9-dimethyl-N-phenyl-9H-fluoren-2-amine (5.05 g, 11.5 mmol) were used.

MS[M+H]+=793

Synthesis of Compound 12

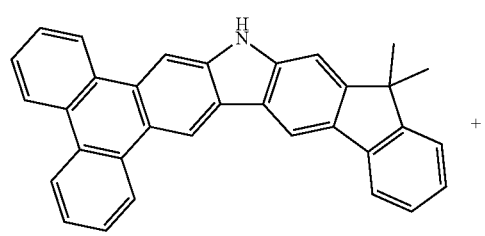

+

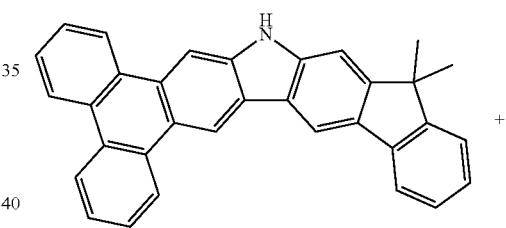

+

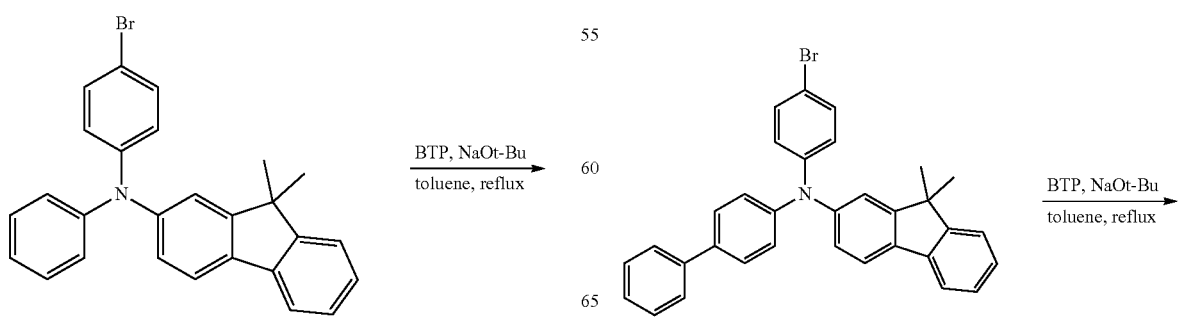

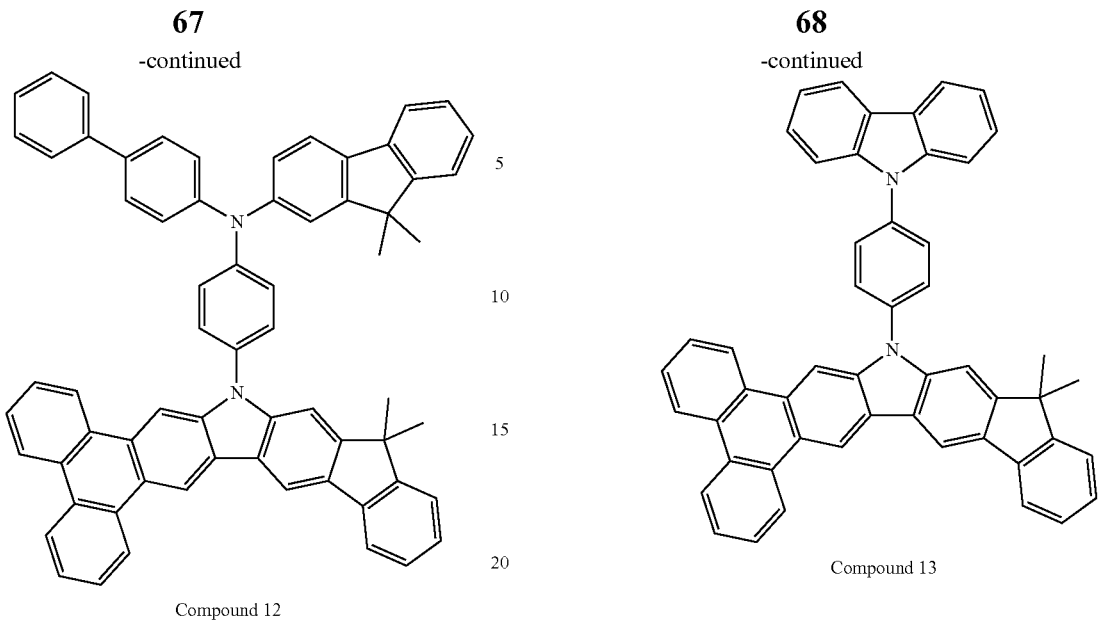

Compound 12

8.9 g of Compound 12 was prepared in the same manner as in the synthesis of Compound 8 except that Core B (5 g, 11.5 mmol) and N-([1,1-biphenyl]-4-yl)-N-(4-bromophenyl)-9,9-dimethyl-9H-fluoren-2-amine (5.92 g, 11.5 mmol) were used.

MS[M+H]+=869

Synthesis of Compound 13

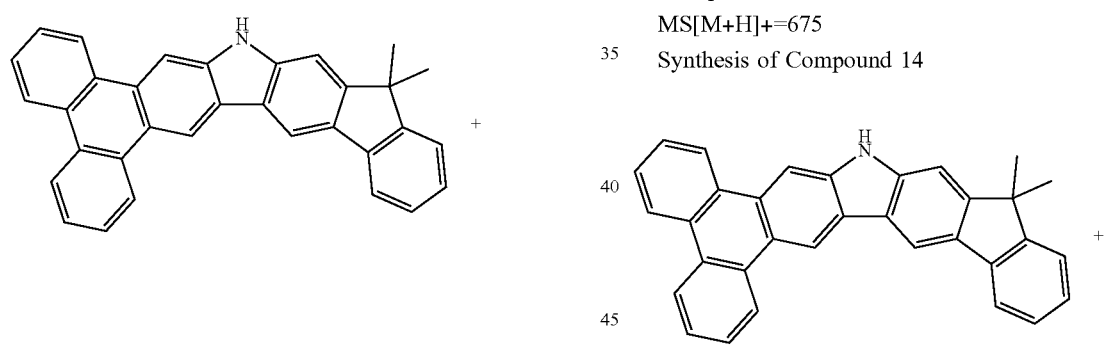

Compound 13

After adding Core B (5 g, 11.5 mmol), 9-(4-bromophenyl)-9H-carbazole (3.69 g, 11.5 mmol) and NaOt-Bu (1.3 g, 13.8 mmol) in 40 ml of toluene, the temperature was raised while stirring the result. After the temperature was raised and the result started to reflux, bis(tri-tertbutylphosphine) palladium (0.11 g, 0.23 mmol) was slowly added dropwise thereto. The reaction was complete after 5 hours and the result was cooled to room temperature, concentrated under reduced pressure, and then column purified to prepare 6.9 g of Compound 13.

MS[M+H]+=675

Synthesis of Compound 14

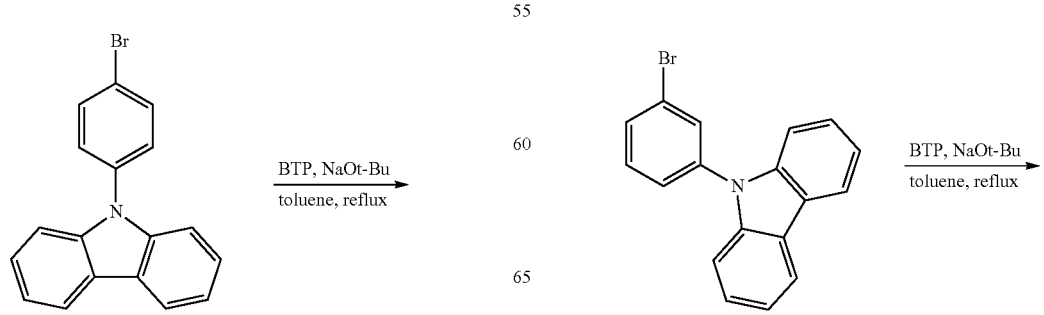

-continued

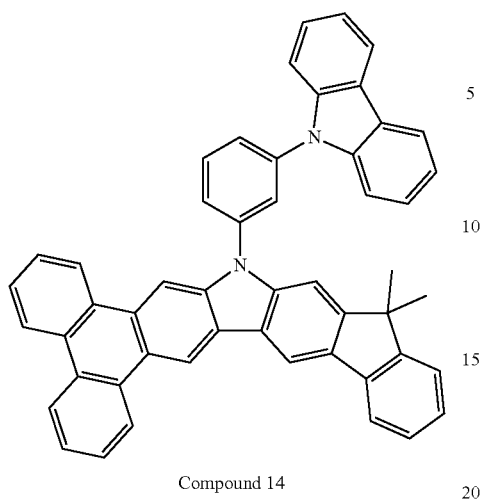

Compound 14

6.7 g of Compound 14 was prepared in the same manner as in the synthesis of Compound 13 except that Core B (5 g, 11.5 mmol) and 9-(3-bromophenyl)-9H-carbazole (3.69 g, 11.5 mmol) were used.

MS[M+H]+=675

Synthesis of Compound 15

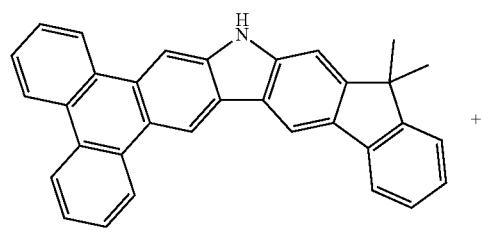

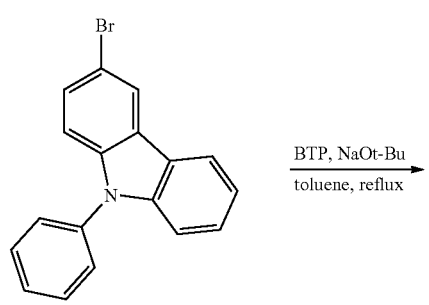

-continued

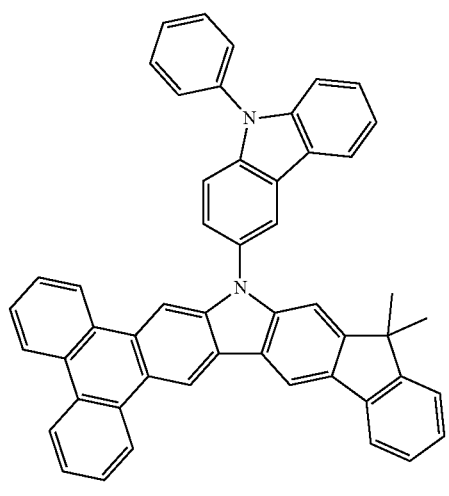

Compound 15

6.8 g of Compound 15 was prepared in the same manner as in the synthesis of Compound 13 except that Core B (5 g, 11.5 mmol) and 3-bromo-9-phenyl-9H-carbazole (3.69 g, 11.5 mmol) were used.

MS[M+H]+=675

Synthesis of Compound 16

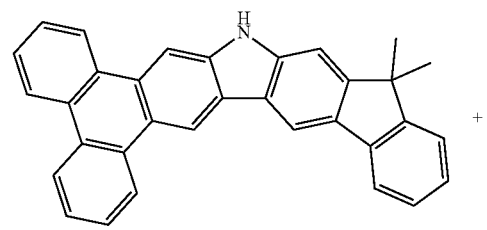

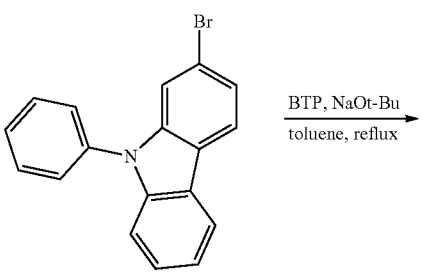

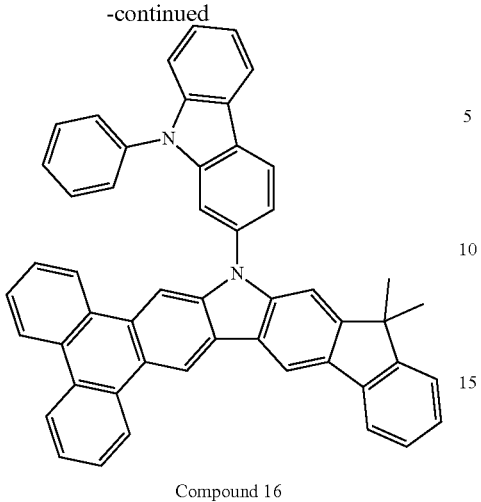

Compound 16

6.7 g of Compound 16 was prepared in the same manner as in the synthesis of Compound 13 except that Core B (5 g, 11.5 mmol) and 2-bromo-9-phenyl-9H-carbazole (3.69 g, 11.5 mmol) were used.

MS[M+H]+=675

Synthesis of Compound 17

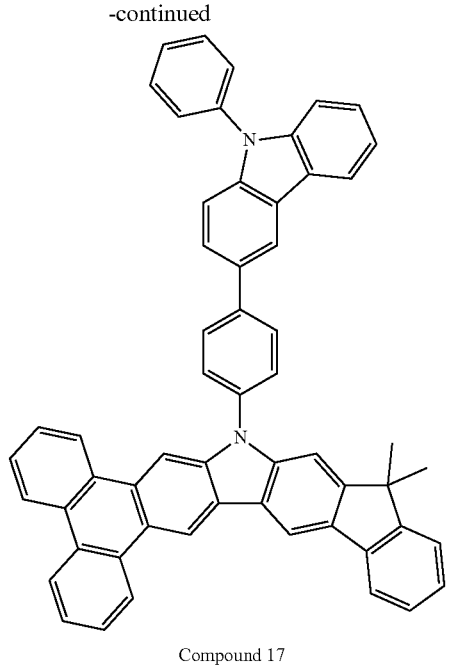

Compound 17

7.2 g of Compound 17 was prepared in the same manner as in the synthesis of Compound 13 except that Core B (5 g, 11.5 mmol) and 3-(4-bromophenyl)-9-phenyl-9H-carbazole (4.57 g, 11.5 mmol) were used.

MS[M+H]+=751

Synthesis of Compound 18

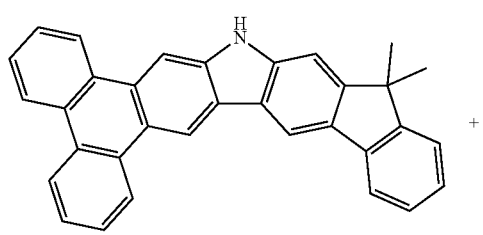
+
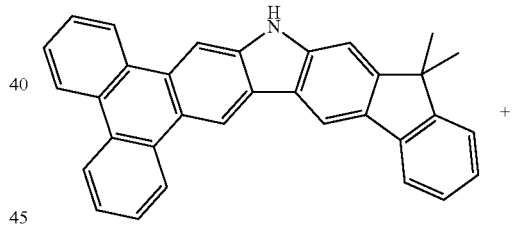

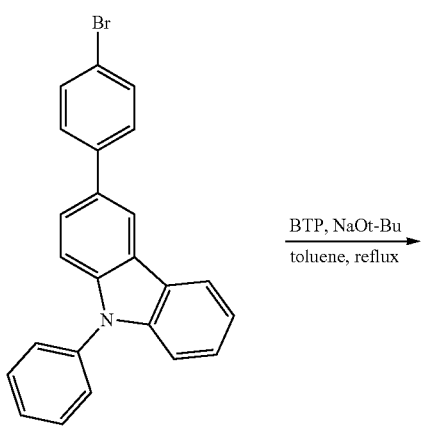

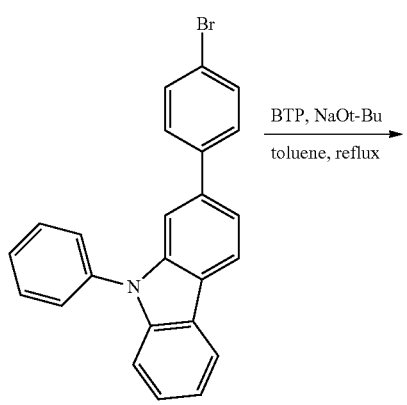

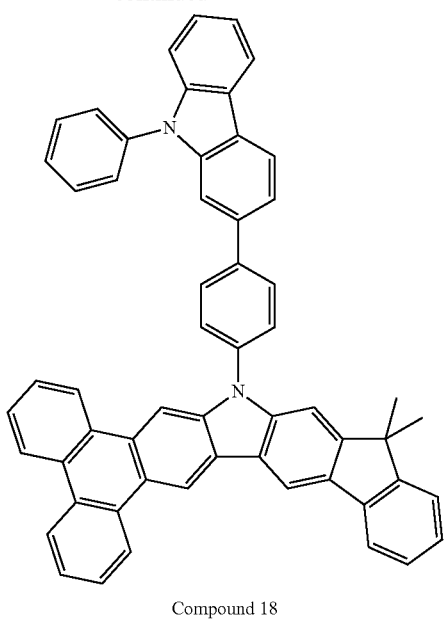

Compound 18

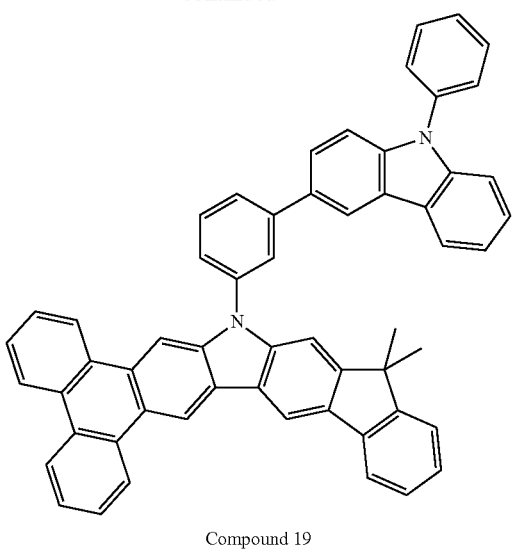

Compound 19

7.0 g of Compound 18 was prepared in the same manner as in the synthesis of Compound 13 except that Core B (5 g, 11.5 mmol) and 2-(4-bromophenyl)-9-phenyl-9H-carbazole (4.57 g, 11.5 mmol) were used.

MS[M+H]+=751

Synthesis of Compound 19

7.4 g of Compound 19 was prepared in the same manner as in the synthesis of Compound 13 except that Core B (5 g, 11.5 mmol) and 3-(3-bromophenyl)-9-phenyl-9H-carbazole (4.57 g, 11.5 mmol) were used.

MS[M+H]+=751

Synthesis of Compound 20

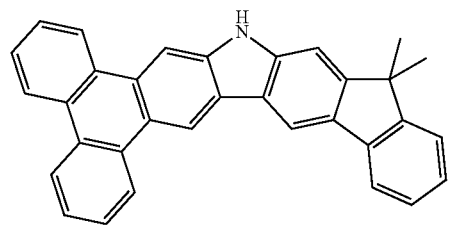

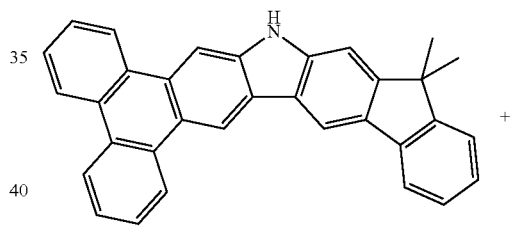

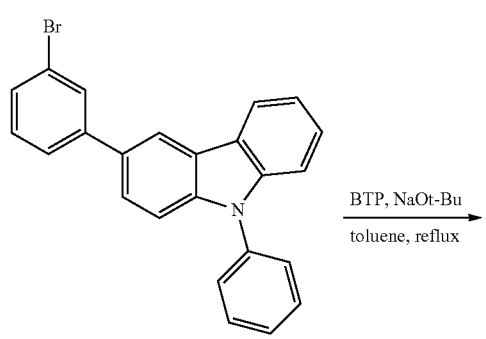

BTP, NaOt-Bu
toluene, reflux

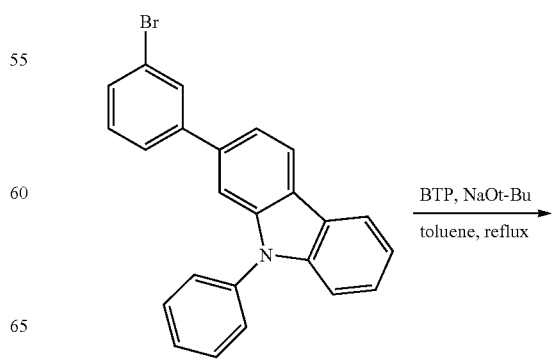

BTP, NaOt-Bu
toluene, reflux

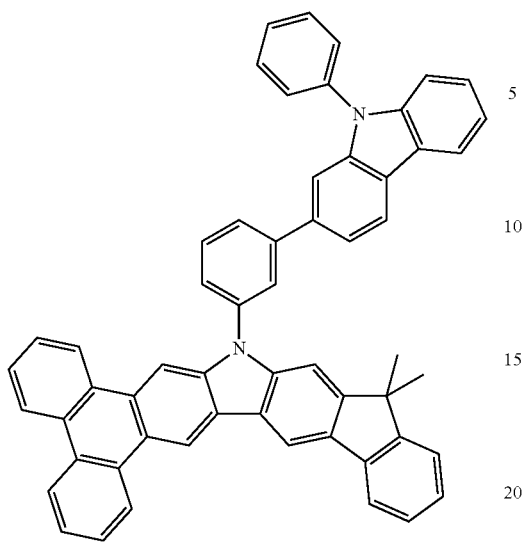

Compound 21

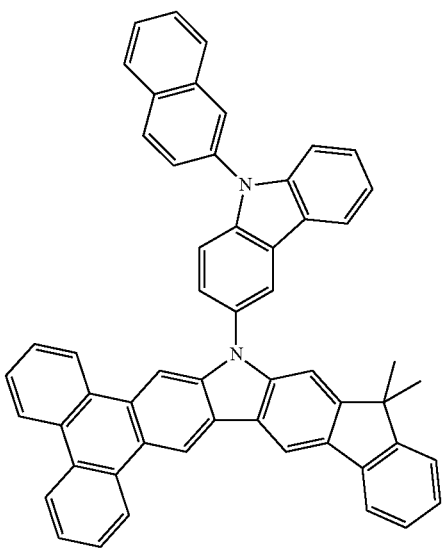

Compound 21

6.9 g of Compound 20 was prepared in the same manner as in the synthesis of Compound 13 except that Core B (5 g, 11.5 mmol) and 2-(3-bromophenyl)-9-phenyl-9H-carbazole (4.57 g, 11.5 mmol) were used.

MS[M+H]+=751

Synthesis of Compound 21

6.3 g of Compound 21 was prepared in the same manner as in the synthesis of Compound 13 except that Core B (5 g, 11.5 mmol) and 3-bromo-9-(naphthalen-2-yl)-9H-carbazole (4.27 g, 11.5 mmol) were used.

MS[M+H]+=725

Synthesis of Compound 22

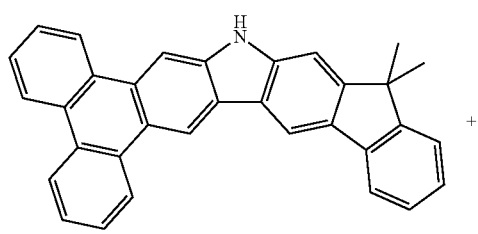

+

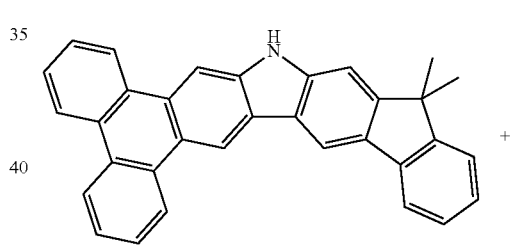

+

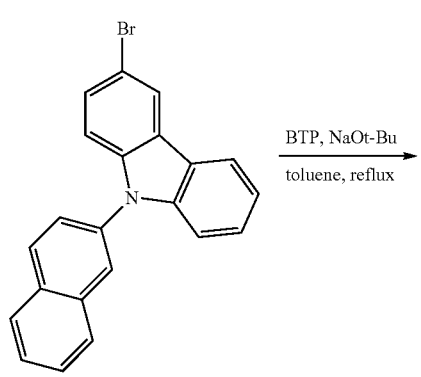

BTP, NaOt-Bu
toluene, reflux
⟶

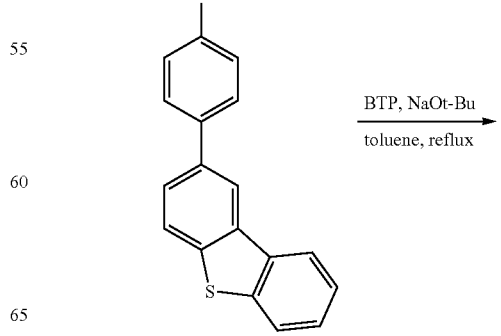

BTP, NaOt-Bu
toluene, reflux
⟶

-continued

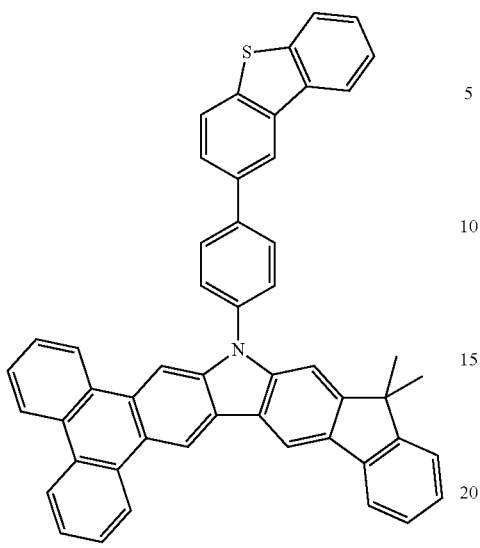

Compound 22

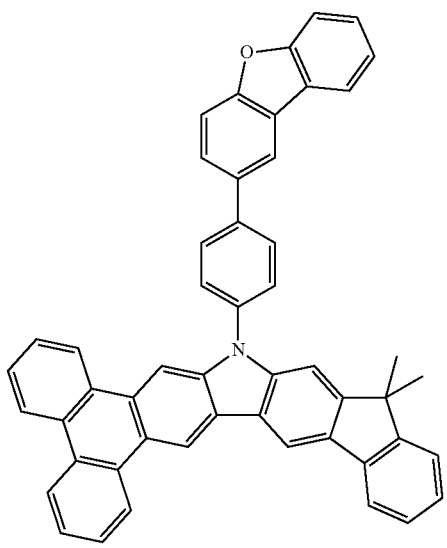

Compound 23

After adding Core B (5 g, 11.5 mmol), 2-(4-bromophenyl)dibenzo[b,d]thiophene (3.89 g, 11.5 mmol) and NaOt-Bu (1.3 g, 13.8 mmol) in 40 ml of toluene, the temperature was raised while stirring the result. After the temperature was raised and the result started to reflux, bis(tri-tertbutylphosphine) palladium (0.11 g, 0.23 mmol) was slowly added dropwise thereto. The reaction was complete after 9 hours and the result was cooled to room temperature, concentrated under reduced pressure, and then column purified to prepare 6.5 g of Compound 22.

MS[M+H]+=692

Synthesis of Compound 23

After adding Core B (5 g, 11.5 mmol), 2-(4-bromophenyl)dibenzo[b,d]furan (3.70 g, 11.5 mmol) and NaOt-Bu (1.3 g, 13.8 mmol) in 40 ml of toluene, the temperature was raised while stirring the result. After the temperature was raised and the result started to reflux, bis(tri-tertbutylphosphine) palladium (0.11 g, 0.23 mmol) was slowly added dropwise thereto. The reaction was complete after 6 hours and the result was cooled to room temperature, concentrated under reduced pressure, and then column purified to prepare 6.1 g of Compound 23.

MS[M+H]+=676

Synthesis of Compound 24

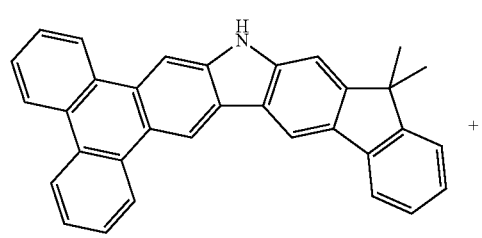 +

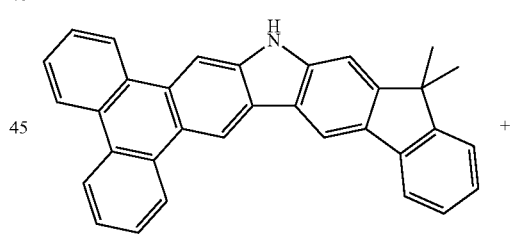 +

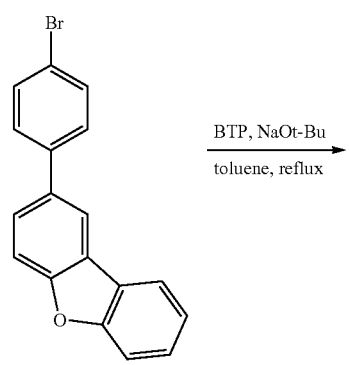

BTP, NaOt-Bu
toluene, reflux
→

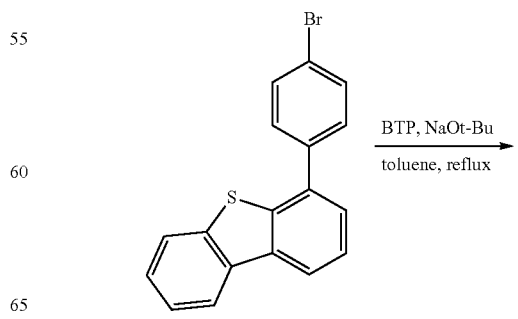

BTP, NaOt-Bu
toluene, reflux
→

-continued

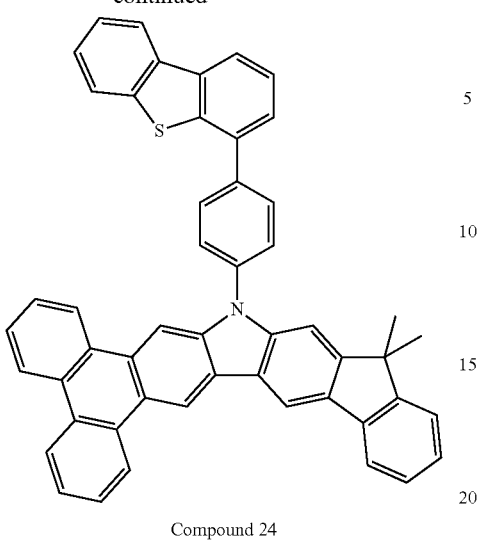
Compound 24

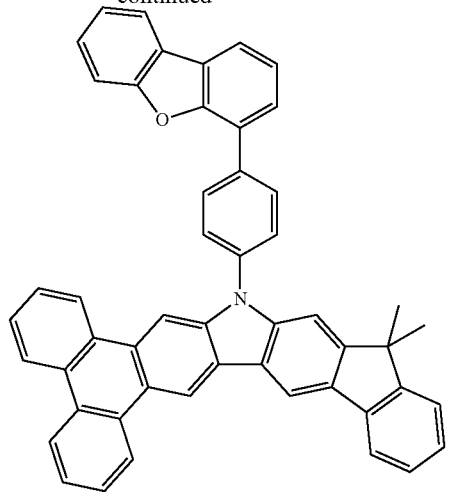
Compound 25

6.3 g of Compound 24 was prepared in the same manner as in the synthesis of Compound 22 except that Core B (5 g, 11.5 mmol) and 4-(4-bromophenyl)dibenzo[b,d]thiophene (3.89 g, 11.5 mmol) were used.

MS[M+H]+=692

Synthesis of Compound 25

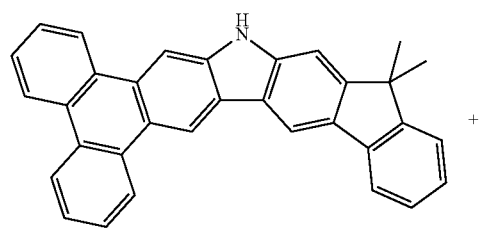

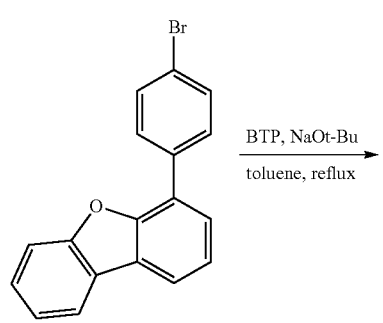

6.2 g of Compound 25 was prepared in the same manner as in the synthesis of Compound 23 except that Core B (5 g, 11.5 mmol) and 4-(4-bromophenyl)dibenzo[b,d]furan (3.70 g, 11.5 mmol) were used.

MS[M+H]+=676

Synthesis of Compound 26

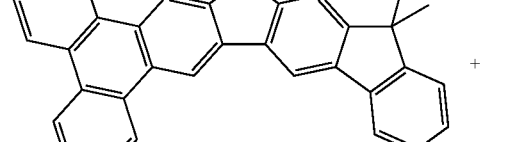

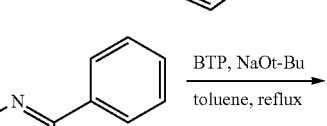

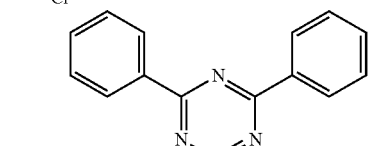

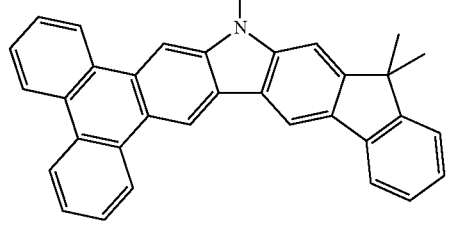
Compound 26

After adding Core B (5 g, 11.5 mmol), 2-chloro-4,6-diphenyl-1,3,5-triazine (3.39 g, 12.7 mmol) and K₃PO₄ (4.88 g, 23 mmol) in 21 ml of xylene and 7 ml of DMAC, the temperature was raised while stirring the result. After the temperature was raised and the result started to reflux, the reaction was complete after 7 hours and the result was cooled to room temperature, concentrated under reduced pressure, and then column purified to prepare 6.7 g of Compound 26.

MS[M+H]+=665

Synthesis of Compound 27

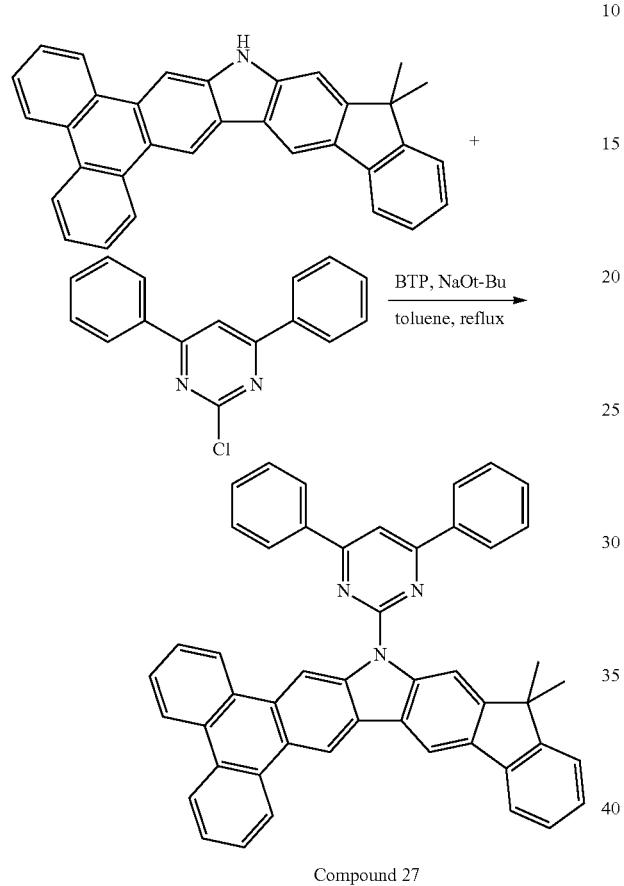

Compound 27

After adding Core B (5 g, 11.5 mmol), 2-chloro-4,6-diphenylpyrimidine (3.38 g, 12.7 mmol) and K$_3$PO$_4$ (4.88 g, 23 mmol) in 21 ml of xylene and 7 ml of DMAC, the temperature was raised while stirring the result. After the temperature was raised and the result started to reflux, the reaction was complete after 5 hours and the result was cooled to room temperature, concentrated under reduced pressure, and then column purified to prepare 6.9 g of Compound 27.

MS[M+H]+=664

Synthesis of Compound 28

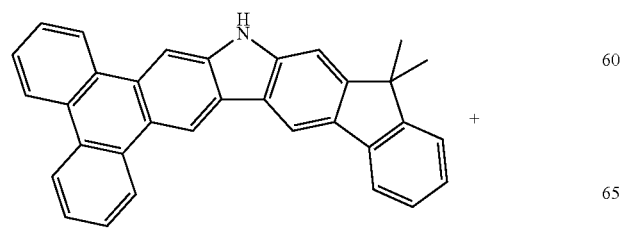

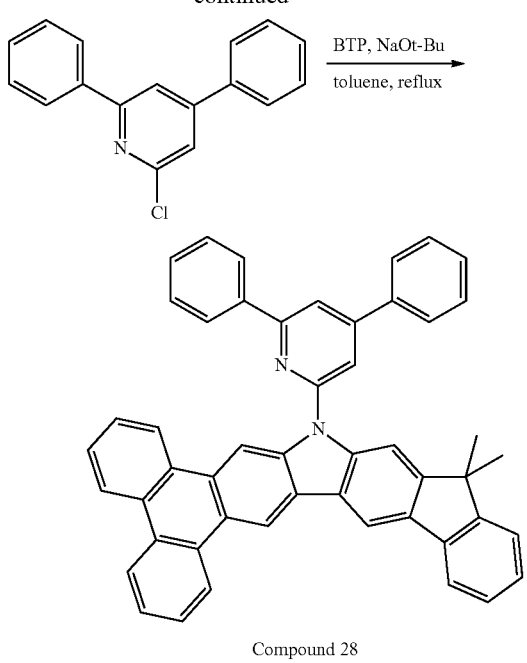

Compound 28

After adding Core B (5 g, 11.5 mmol), 2-chloro-4,6-diphenylpyridine (3.37 g, 12.7 mmol) and K$_3$PO$_4$ (4.88 g, 23 mmol) in 21 ml of xylene and 7 ml of DMAC, the temperature was raised while stirring the result. After the temperature was raised and the result started to reflux, the reaction was complete after 9 hours and the result was cooled to room temperature, concentrated under reduced pressure, and then column purified to prepare 6.4 g of Compound 28.

MS[M+H]+=663

Synthesis of Compound 29

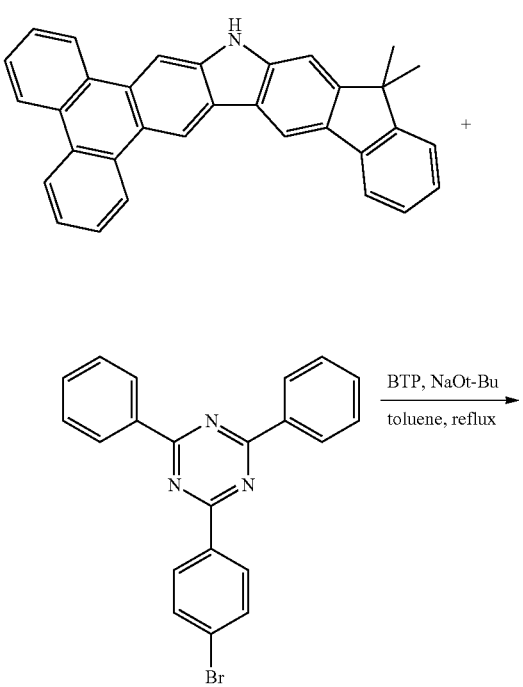

-continued

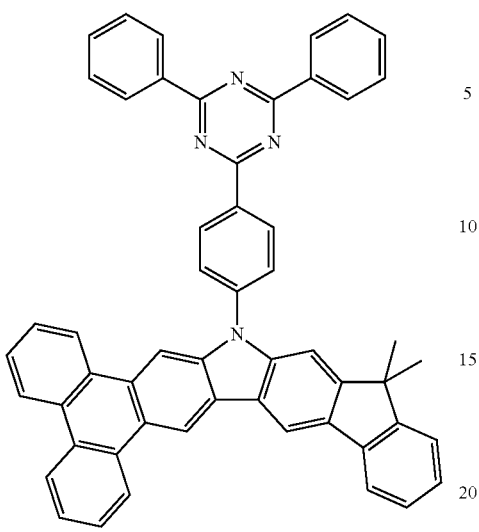

Compound 29

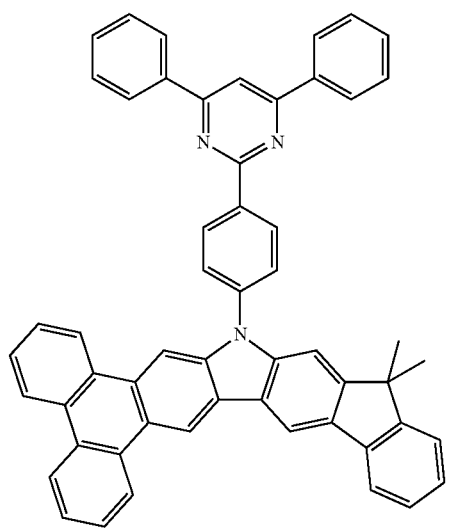

Compound 30

After adding Core B (5 g, 11.5 mmol), 2-(4-bromophenyl) 4,6-diphenyl-1,3,5-triazine (4.45 g, 11.5 mmol) and NaOt-Bu (1.3 g, 13.8 mmol) in 40 ml of toluene, the temperature was raised while stirring the result. After the temperature was raised and the result started to reflux, bis(tri-tertbutylphosphine) palladium (0.11 g, 0.23 mmol) was slowly added dropwise thereto. The reaction was complete after 6 hours and the result was cooled to room temperature, concentrated under reduced pressure, and then column purified to prepare 7.3 g of Compound 29.

MS[M+H]+=741

Synthesis of Compound 30

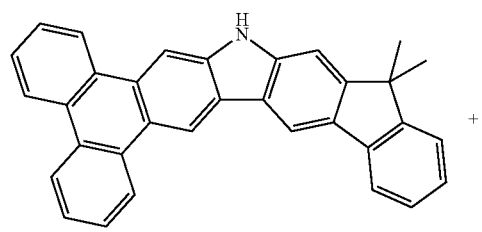

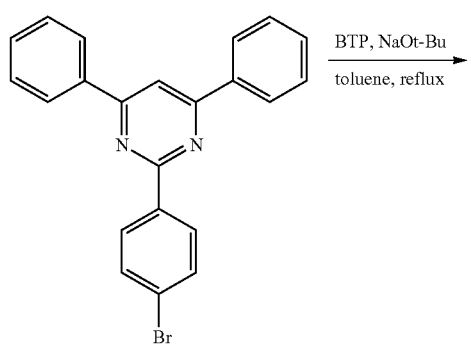

After adding Core B (5 g, 11.5 mmol), 2-(4-bromophenyl) 4,6-diphenylpyrimidine (4.44 g, 11.5 mmol) and NaOt-Bu (1.3 g, 13.8 mmol) in 40 ml of toluene, the temperature was raised while stirring the result. After the temperature was raised and the result started to reflux, bis(tri-tertbutylphosphine) palladium (0.11 g, 0.23 mmol) was slowly added dropwise thereto. The reaction was complete after 8 hours and the result was cooled to room temperature, concentrated under reduced pressure, and then column purified to prepare 7.0 g of Compound 30.

MS[M+H]+=740

Synthesis of Compound 31

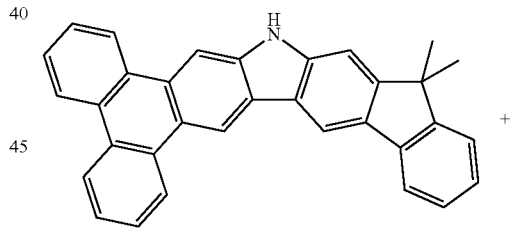

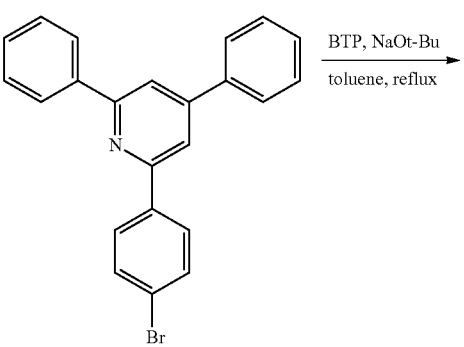

-continued

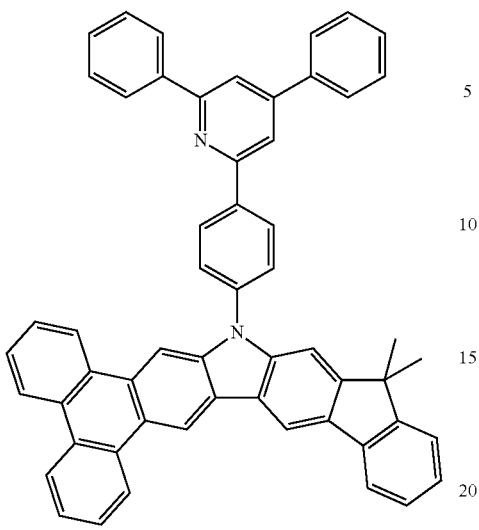

Compound 31

6.8 g of Compound 31 was prepared in the same manner as in the synthesis of Compound 30 except that Core B (5 g, 11.5 mmol) and 2-(4-bromophenyl)4,6-diphenylpyridine (4.43 g, 11.5 mmol) were used.

MS[M+H]+=739

Synthesis of Compound 32

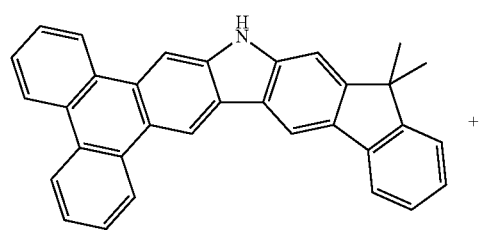

+

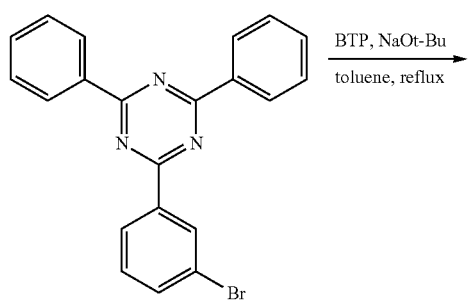

BTP, NaOt-Bu
toluene, reflux
→

-continued

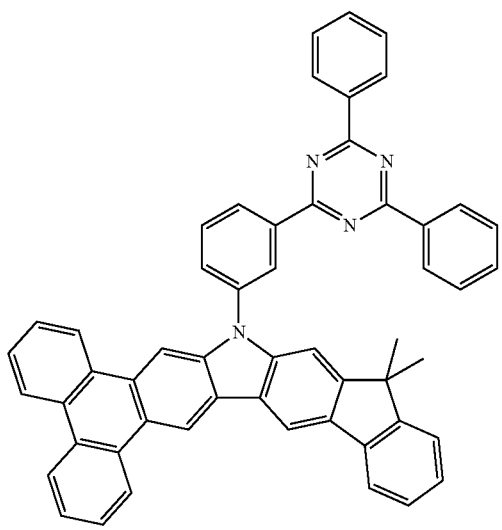

Compound 32

7.2 g of Compound 32 was prepared in the same manner as in the synthesis of Compound 31 except that Core B (5 g, 11.5 mmol) and 2-(3-bromophenyl)4,6-diphenyl-1,3,5-triazine (4.45 g, 11.5 mmol) were used.

MS[M+H]+=741

Synthesis of Compound 33

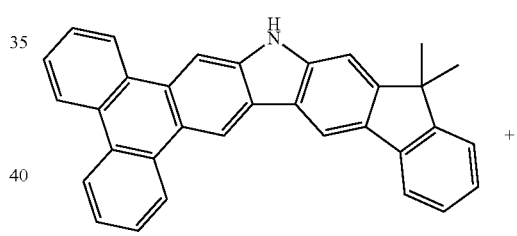

+

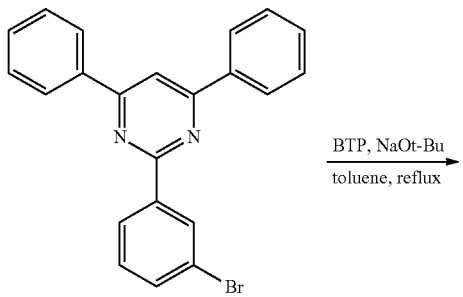

BTP, NaOt-Bu
toluene, reflux
→

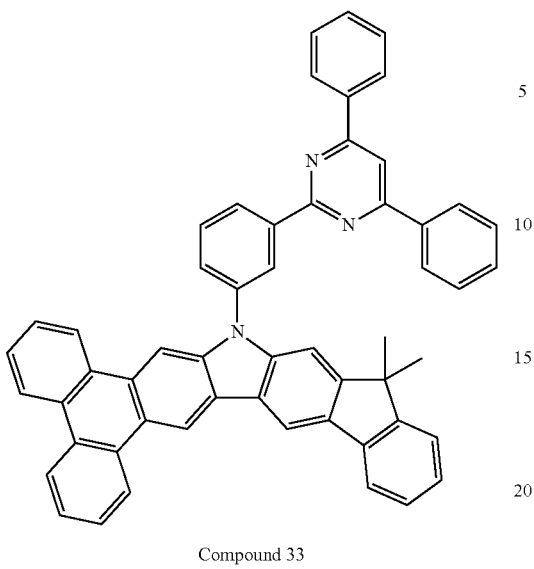

Compound 33

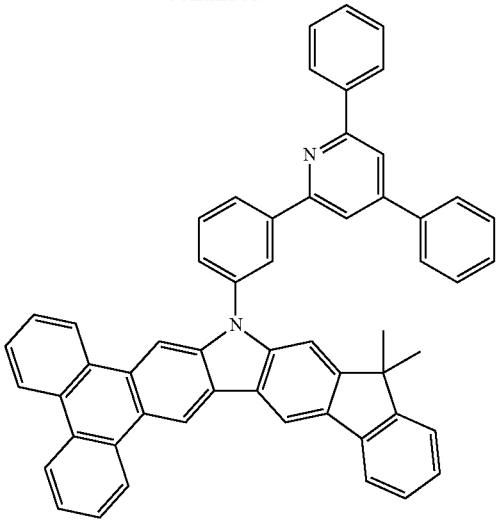

Compound 34

7.0 g of Compound 33 was prepared in the same manner as in the synthesis of Compound 32 except that Core B (5 g, 11.5 mmol) and 2-(3-bromophenyl)4,6-diphenylpyrimidine (4.44 g, 11.5 mmol) were used.

MS[M+H]+=740

Synthesis of Compound 34

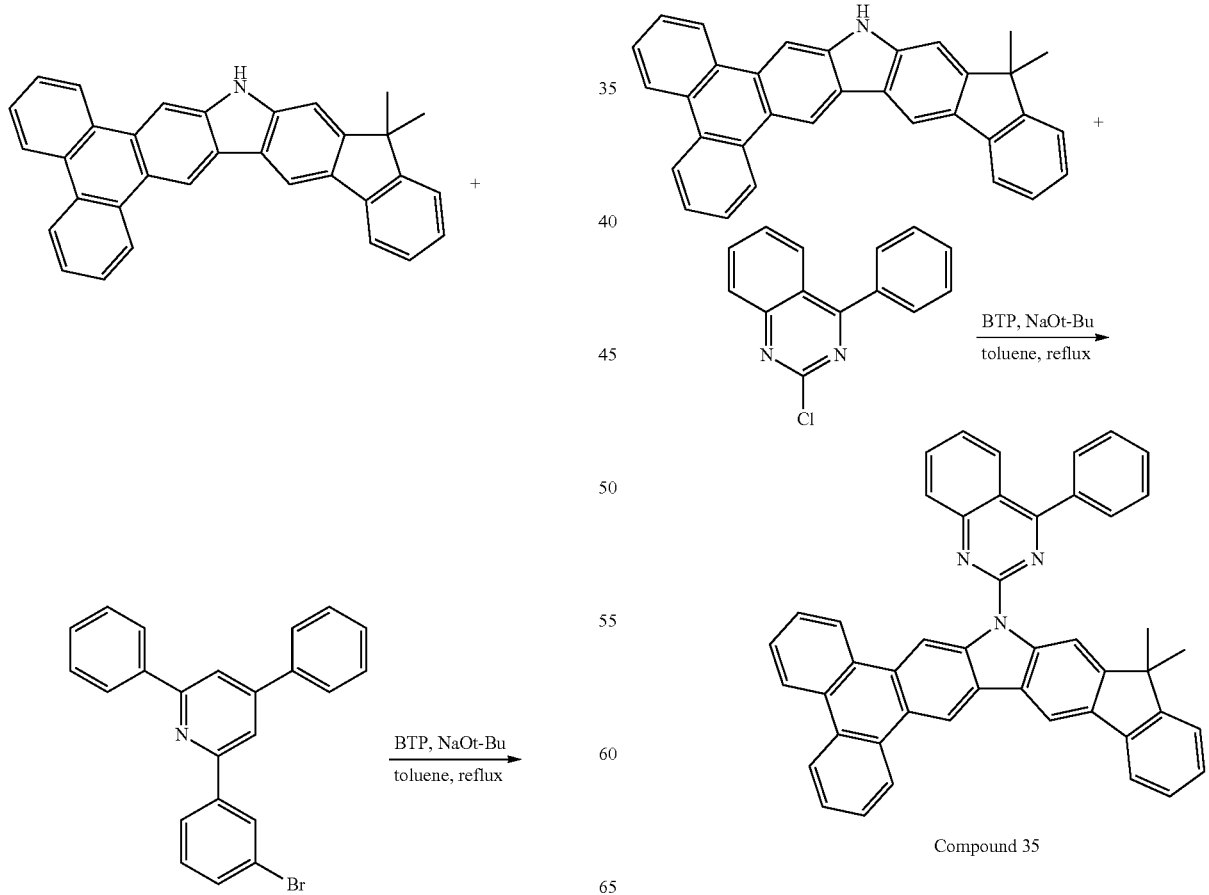

6.8 g of Compound 34 was prepared in the same manner as in the synthesis of Compound 33 except that Core B (5 g, 11.5 mmol) and 2-(3-bromophenyl)4,6-diphenylpyridine (4.43 g, 11.5 mmol) were used.

MS[M+H]+=739

Synthesis of Compound 35

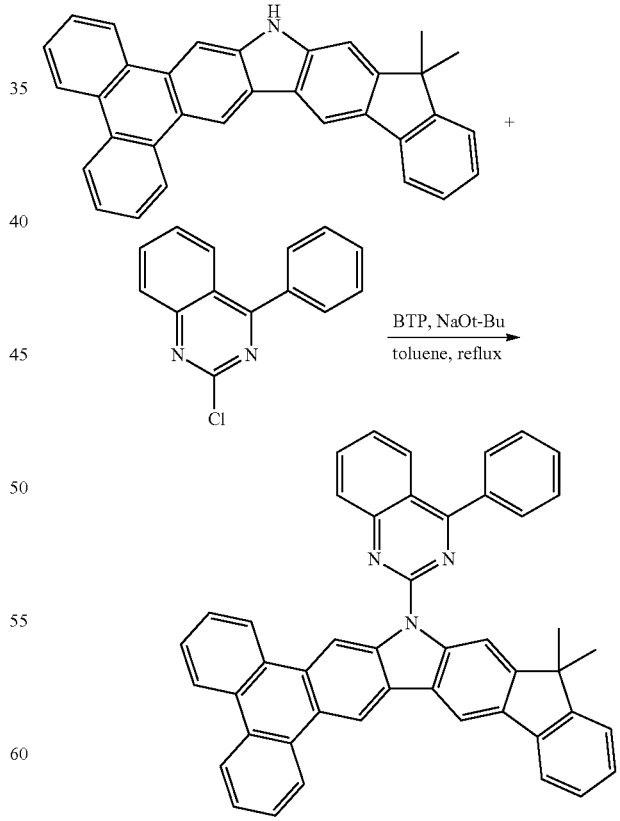

Compound 35

After adding Core B (5 g, 11.5 mmol), 2-chloro-4-phenylquinazoline (3.05 g, 12.7 mmol) and K$_3$PO$_4$ (4.88 g, 23 mmol) in 21 ml of xylene and 7 ml of DMAC, the temperature was raised while stirring the result. After the temperature was raised and the result started to reflux, the reaction was complete after 5 hours and the result was cooled to room temperature, concentrated under reduced pressure, and then column purified to prepare 6.0 g of Compound 35.

MS[M+H]+=638

Synthesis of Compound 36

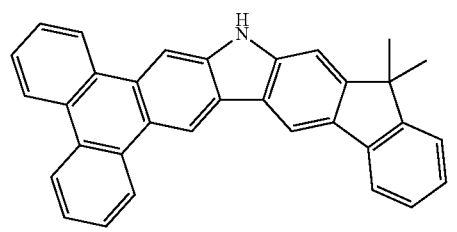

+

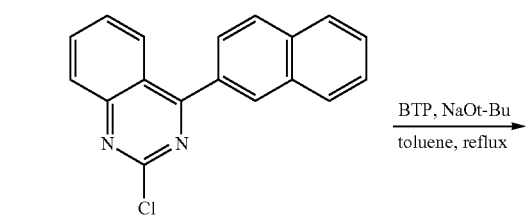

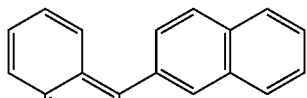

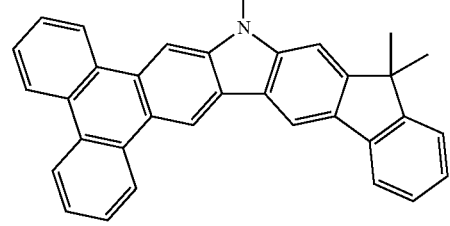

Compound 36

6.7 g of Compound 36 was prepared in the same manner as in the synthesis of Compound 35 except that Core B (5 g, 11.5 mmol) and 2-chloro-4-(naphthalen-2-yl)quinazoline (3.68 g, 12.7 mmol) were used.

MS[M+H]+=688

Synthesis of Compound 37

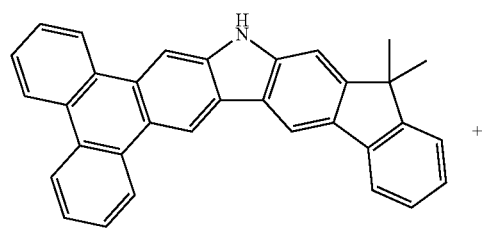

+

-continued

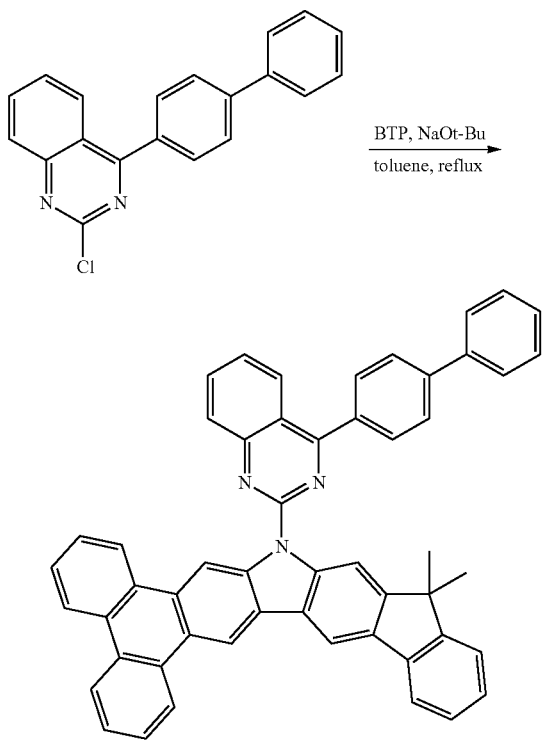

Compound 37

6.8 g of Compound 37 was prepared in the same manner as in the synthesis of Compound 35 except that Core B (5 g, 11.5 mmol) and 4-([1,1-biphenyl]-4-yl)2-chloroquinazoline (4.01 g, 12.7 mmol) were used.

MS[M+H]+=714

Synthesis of Compound 38

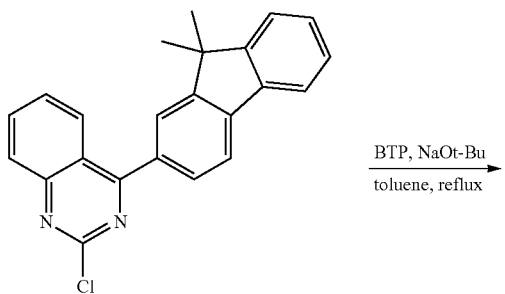

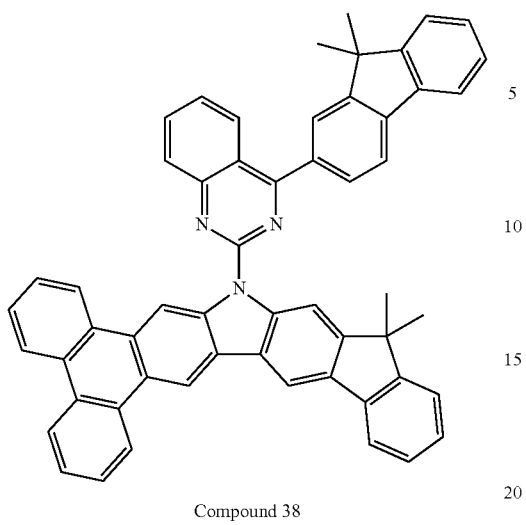

Compound 38

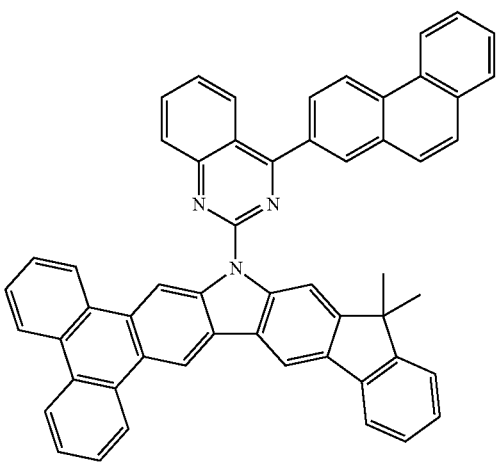

Compound 39

7.6 g of Compound 38 was prepared in the same manner as in the synthesis of Compound 35 except that Core B (5 g, 11.5 mmol) and 2-chloro-4-(9,9-dimethyl-9H-fluoren-2-yl)quinazoline (4.52 g, 12.7 mmol) were used.

MS[M+H]+=754

Synthesis of Compound 39

7.2 g of Compound 39 was prepared in the same manner as in the synthesis of Compound 35 except that Core B (5 g, 11.5 mmol) and 2-chloro-4-(phenanthren-2-yl)quinazoline (4.32 g, 12.7 mmol) were used.

MS[M+H]+=738

Synthesis of Compound 40

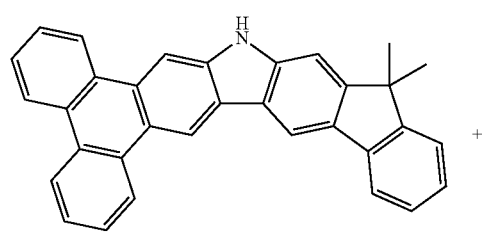

+

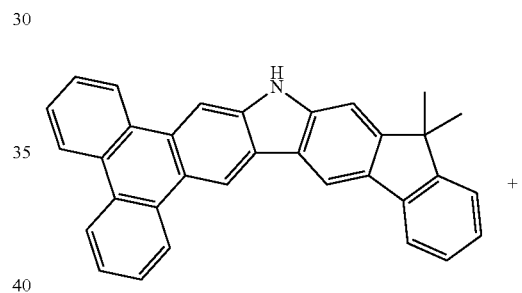

+

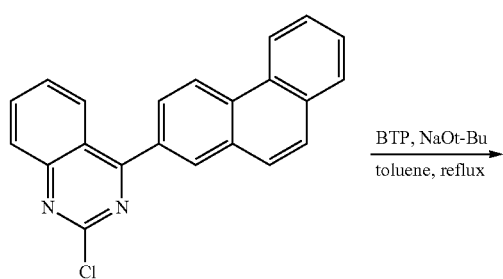

BTP, NaOt-Bu
toluene, reflux
→

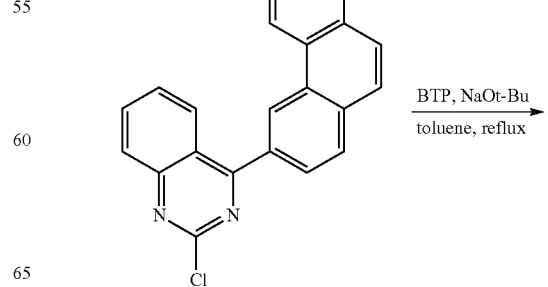

BTP, NaOt-Bu
toluene, reflux
→

-continued

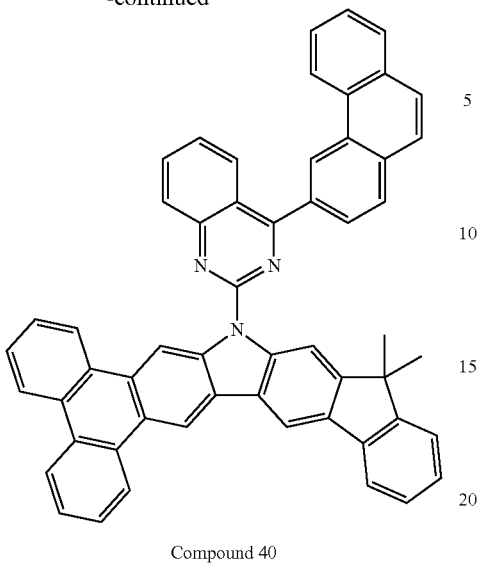

Compound 40

7.0 g of Compound 40 was prepared in the same manner as in the synthesis of Compound 35 except that Core B (5 g, 11.5 mmol) and 2-chloro-4-(phenanthren-3-yl)quinazoline (4.32 g, 12.7 mmol) were used.
MS[M+H]+=738

Example 1

Example 1-1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing hexanitrile hexaazatriphenylene (HAT) of the following chemical formula to a thickness of 500 Å.

[HAT]

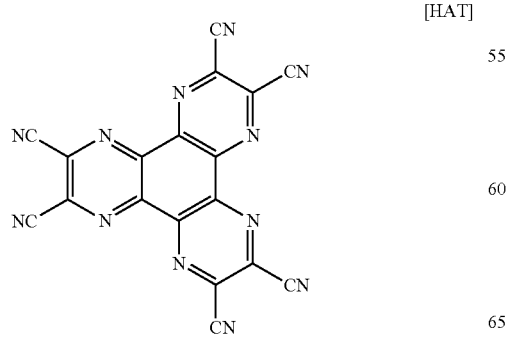

A hole transfer layer was formed on the hole injection layer by vacuum depositing the following compound 4-4'-bis[N-(1-naphthyl)-N-phenylamino]biphenyl (NPB) (300 Å), a material transferring holes.

[NPB]

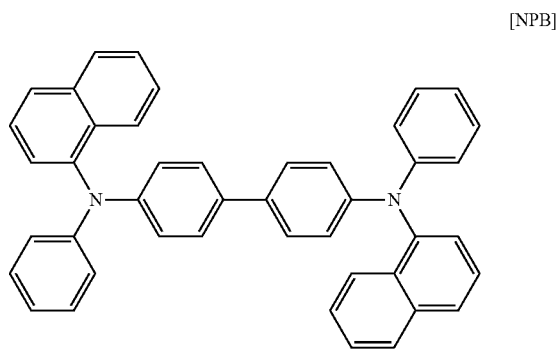 [SMILES: c1ccc(N(c2ccc(-c3ccc(N(c4ccccc4)c4cccc5ccccc45)cc3)cc2)c2cccc3ccccc23)cc1]

Subsequently, an electron blocking layer was formed on the hole transfer layer to a film thickness of 100 Å by vacuum depositing the following Compound 1.

[Compound 1]

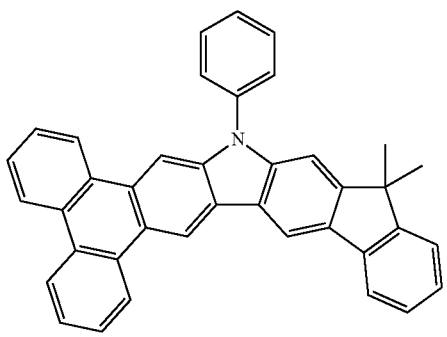

Next, a light emitting layer was formed on the electron blocking layer to a film thickness of 300 Å by vacuum depositing BH and BD shown below in a weight ratio of 25:1.

[BH]
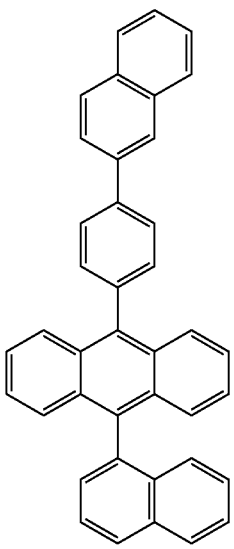

[BD]
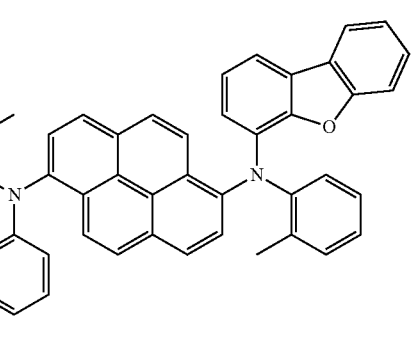

[ET1]
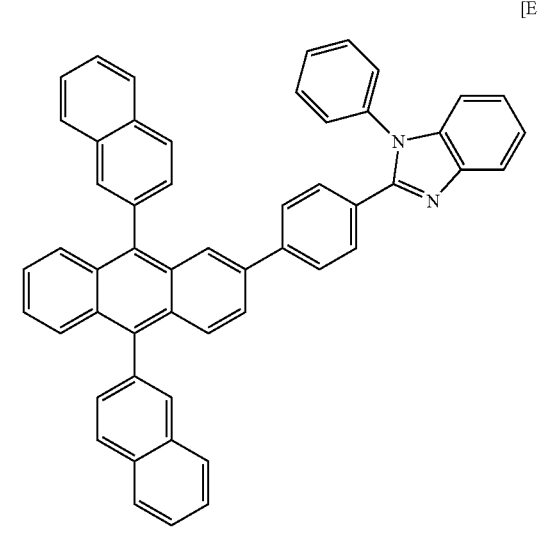

[LiQ]
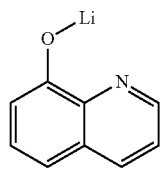

An electron injection and transfer layer was formed on the light emitting layer to a thickness of 300 Å by vacuum depositing the compound ET1 and the compound lithium quinolate (LiQ) in a weight ratio of 1:1. A cathode was formed on the electron injection and transfer layer by depositing lithium fluoride (LiF) to a thickness of 12 Å and aluminum to a thickness of 2,000 Å in consecutive order.

In the above-mentioned process, the deposition rates of the organic materials were maintained at 0.4 to 0.7 Å/sec, the deposition rates of the lithium fluoride and the aluminum of the cathode were maintained at 0.3 Å/sec and 2 Å/sec, respectively, and the degree of vacuum during the deposition was maintained at $2 \times 10^{-7}$ to $5 \times 10^{-6}$ torr.

Example 1-2

An organic light emitting device was manufactured in the same manner as in Example 1-1 except that Compound 2 was used instead of Compound 1.

Example 1-3

An organic light emitting device was manufactured in the same manner as in Example 1-1 except that Compound 3 was used instead of Compound 1.

Example 1-4

An organic light emitting device was manufactured in the same manner as in Example 1-1 except that Compound 4 was used instead of Compound 1.

Example 1-5

An organic light emitting device was manufactured in the same manner as in Example 1-1 except that Compound 5 was used instead of Compound 1.

Example 1-6

An organic light emitting device was manufactured in the same manner as in Example 1-1 except that Compound 6 was used instead of Compound 1.

Example 1-7

An organic light emitting device was manufactured in the same manner as in Example 1-1 except that Compound 7 was used instead of Compound 1.

Example 1-8

An organic light emitting device was manufactured in the same manner as in Example 1-1 except that Compound 8 was used instead of Compound 1.

Example 1-9

An organic light emitting device was manufactured in the same manner as in Example 1-1 except that Compound 9 was used instead of Compound 1.

Example 1-10

An organic light emitting device was manufactured in the same manner as in Example 1-1 except that Compound 10 was used instead of Compound 1.

Example 1-11

An organic light emitting device was manufactured in the same manner as in Example 1-1 except that Compound 11 was used instead of Compound 1.

Example 1-12

An organic light emitting device was manufactured in the same manner as in Example 1-1 except that Compound 12 was used instead of Compound 1.

Example 1-13

An organic light emitting device was manufactured in the same manner as in Example 1-1 except that Compound 13 was used instead of Compound 1.

Example 1-14

An organic light emitting device was manufactured in the same manner as in Example 1-1 except that Compound 14 was used instead of Compound 1.

Example 1-15

An organic light emitting device was manufactured in the same manner as in Example 1-1 except that Compound 15 was used instead of Compound 1.

Example 1-16

An organic light emitting device was manufactured in the same manner as in Example 1-1 except that Compound 16 was used instead of Compound 1.

Example 1-17

An organic light emitting device was manufactured in the same manner as in Example 1-1 except that Compound 17 was used instead of Compound 1.

Example 1-18

An organic light emitting device was manufactured in the same manner as in Example 1-1 except that Compound 18 was used instead of Compound 1.

Example 1-19

An organic light emitting device was manufactured in the same manner as in Example 1-1 except that Compound 19 was used instead of Compound 1.

Example 1-20

An organic light emitting device was manufactured in the same manner as in Example 1-1 except that Compound 20 was used instead of Compound 1.

Example 1-21

An organic light emitting device was manufactured in the same manner as in Example 1-1 except that Compound 21 was used instead of Compound 1.

Example 1-22

An organic light emitting device was manufactured in the same manner as in Example 1-1 except that Compound 22 was used instead of Compound 1.

Example 1-23

An organic light emitting device was manufactured in the same manner as in Example 1-1 except that Compound 23 was used instead of Compound 1.

Example 1-24

An organic light emitting device was manufactured in the same manner as in Example 1-1 except that Compound 24 was used instead of Compound 1.

Example 1-25

An organic light emitting device was manufactured in the same manner as in Example 1-1 except that Compound 25 was used instead of Compound 1.

Comparative Example 1-1

An organic light emitting device was manufactured in the same manner as in Example 1-1 except that EB 1 (TCTA) was used instead of Compound 1.

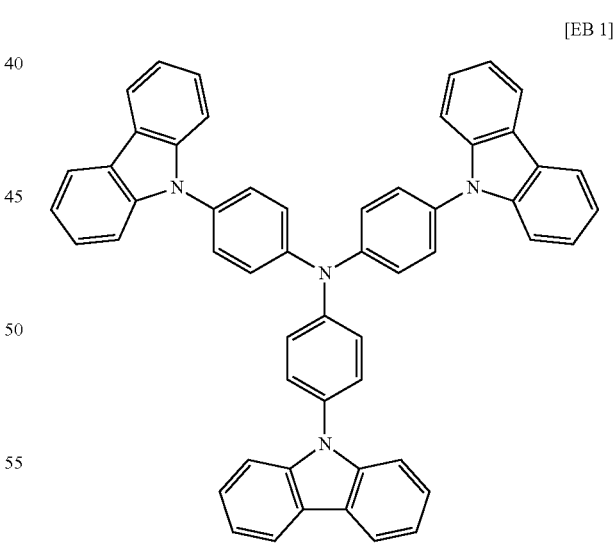

[EB 1]

Comparative Example 1-2

An organic light emitting device was manufactured in the same manner as in Example 1-1 except that EB 2 was used instead of Compound 1.

[EB 2]

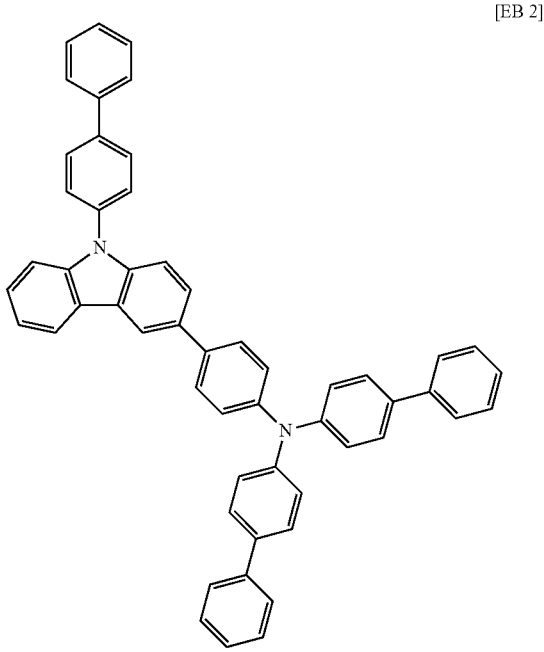 [SMILES: c1ccc(-c2ccc(N(c3ccc(-c4ccccc4)cc3)c3ccc(-c4ccc5c(c4)c4ccccc4n5-c4ccc(-c5ccccc5)cc4)cc3)cc2)cc1]

When a current was applied to the organic light emitting devices manufactured in Examples 1-1 to 1-25, and Comparative Examples 1-1 and 1-2, the results of Table 1 were obtained.

TABLE 1

| | Compound (Electron Blocking Layer) | Voltage (V@10 mA/cm$^2$) | Efficiency (cd/A@10 mA/cm$^2$) | Color Coordinates (x, y) |
|---|---|---|---|---|
| Example 1-1 | Compound 1 | 3.85 | 5.45 | (0.139, 0.122) |
| Example 1-2 | Compound 2 | 3.82 | 5.48 | (0.138, 0.126) |
| Example 1-3 | Compound 3 | 3.87 | 5.41 | (0.138, 0.127) |
| Example 1-4 | Compound 4 | 3.88 | 5.42 | (0.137, 0.125) |
| Example 1-5 | Compound 5 | 3.89 | 5.43 | (0.136, 0.125) |
| Example 1-6 | Compound 6 | 3.74 | 5.47 | (0.136, 0.127) |
| Example 1-7 | Compound 7 | 3.83 | 5.48 | (0.136, 0.125) |
| Example 1-8 | Compound 8 | 3.84 | 5.41 | (0.137, 0.125) |
| Example 1-9 | Compound 9 | 3.83 | 5.48 | (0.138, 0.125) |
| Example 1-10 | Compound 10 | 3.84 | 5.42 | (0.136, 0.125) |
| Example 1-11 | Compound 11 | 3.78 | 5.47 | (0.137, 0.125) |
| Example 1-12 | Compound 12 | 3.79 | 5.55 | (0.136, 0.125) |
| Example 1-13 | Compound 13 | 3.72 | 5.58 | (0.138, 0.126) |
| Example 1-14 | Compound 14 | 3.77 | 5.51 | (0.137, 0.125) |
| Example 1-15 | Compound 15 | 3.78 | 5.52 | (0.136, 0.127) |
| Example 1-16 | Compound 16 | 3.79 | 5.53 | (0.135, 0.127) |
| Example 1-17 | Compound 17 | 3.74 | 5.57 | (0.138, 0.127) |
| Example 1-18 | Compound 18 | 3.73 | 5.58 | (0.137, 0.125) |
| Example 1-19 | Compound 19 | 3.74 | 5.51 | (0.137, 0.125) |
| Example 1-20 | Compound 20 | 3.73 | 5.58 | (0.136, 0.127) |
| Example 1-21 | Compound 21 | 3.74 | 5.52 | (0.135, 0.127) |
| Example 1-22 | Compound 22 | 3.93 | 5.57 | (0.138, 0.127) |
| Example 1-23 | Compound 23 | 3.99 | 5.35 | (0.137, 0.125) |
| Example 1-24 | Compound 24 | 3.98 | 5.38 | (0.137, 0.125) |
| Example 1-25 | Compound 25 | 3.97 | 5.31 | (0.136, 0.125) |
| Comparative Example 1-1 | EB1 | 4.48 | 5.09 | (0.138, 0.127) |
| Comparative Example 1-2 | EB2 | 4.39 | 5.10 | (0.139, 0.122) |

As seen in Table 1, it was seen that Examples 1-1 to 1-25 using Compounds 1 to 25 all exhibited low voltage and high efficiency properties compared to Comparative Examples 1-1 and 1-2. Particularly in Examples 1-13 to 1-21 using Compounds 13 to 21 having substituted carbazole, low voltage and high efficiency properties were most well identified.

It was identified that compound derivatives of the chemical Formulae according to the present invention had an excellent electron blocking ability thereby exhibited low voltage and high efficiency properties, and were capable of being used in an organic light emitting device.

Example 2

<Example 2-1> to <Example 2-25>

Organic light emitting devices were manufactured in the same manner as in Example 1 except that EB 1 was used as the electron blocking layer, and Compounds 1 to 25 were each used instead of NPB as the hole transfer layer.

Comparative Example 2-1

An organic light emitting device was manufactured in the same manner as in Example 1 except that EB 1 was used as the electron blocking layer, and HT1 (NPB) was used as the hole transfer layer.

[HT 1]

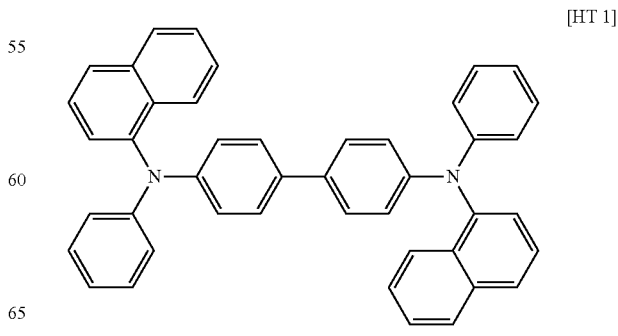

Comparative Example 2-2

An organic light emitting device was manufactured in the same manner as in Example 1 except that EB 1 was used as the electron blocking layer, and HT 2 was used as the hole transfer layer.

[HT 2]

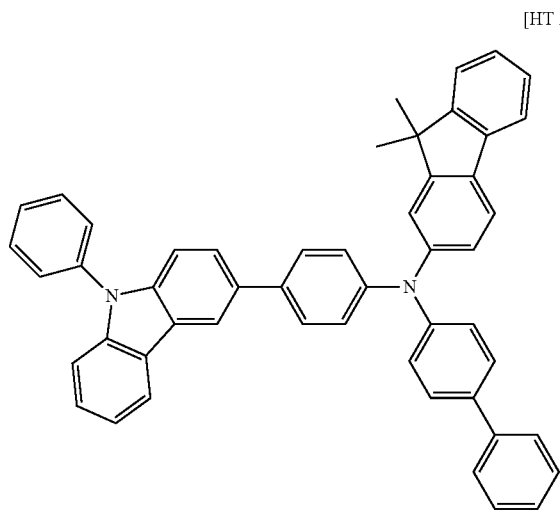

When a current was applied to the organic light emitting devices manufactured in Examples 2-1 to 2-25, and Comparative Examples 2-1 and 2-2, the results of Table 2 were obtained.

TABLE 2

| | Compound (Electron Transfer Layer) | Voltage (V@10 mA/cm$^2$) | Efficiency (cd/A@10 mA/cm$^2$) | Color Coordinates (x, y) |
|---|---|---|---|---|
| Example 2-1 | Compound 1 | 4.55 | 5.75 | (0.139, 0.122) |
| Example 2-2 | Compound 2 | 4.52 | 5.78 | (0.138, 0.126) |
| Example 2-3 | Compound 3 | 4.57 | 5.71 | (0.138, 0.127) |
| Example 2-4 | Compound 4 | 4.58 | 5.72 | (0.137, 0.125) |
| Example 2-5 | Compound 5 | 4.59 | 5.73 | (0.136, 0.125) |
| Example 2-6 | Compound 6 | 4.54 | 5.77 | (0.136, 0.127) |
| Example 2-7 | Compound 7 | 4.50 | 5.78 | (0.136, 0.125) |
| Example 2-8 | Compound 8 | 4.44 | 5.71 | (0.137, 0.125) |
| Example 2-9 | Compound 9 | 4.43 | 5.78 | (0.138, 0.125) |
| Example 2-10 | Compound 10 | 4.44 | 5.72 | (0.136, 0.125) |
| Example 2-11 | Compound 11 | 4.43 | 5.77 | (0.137, 0.125) |
| Example 2-12 | Compound 12 | 4.45 | 5.75 | (0.136, 0.125) |
| Example 2-13 | Compound 13 | 4.32 | 5.88 | (0.138, 0.126) |
| Example 2-14 | Compound 14 | 4.37 | 5.81 | (0.137, 0.125) |
| Example 2-15 | Compound 15 | 4.38 | 5.82 | (0.136, 0.127) |
| Example 2-16 | Compound 16 | 4.39 | 5.83 | (0.135, 0.127) |
| Example 2-17 | Compound 17 | 4.34 | 5.87 | (0.138, 0.127) |
| Example 2-18 | Compound 18 | 4.33 | 5.88 | (0.137, 0.125) |
| Example 2-19 | Compound 19 | 4.34 | 5.81 | (0.137, 0.125) |
| Example 2-20 | Compound 20 | 4.33 | 5.88 | (0.136, 0.127) |
| Example 2-21 | Compound 21 | 4.34 | 5.82 | (0.135, 0.127) |
| Example 2-22 | Compound 22 | 4.63 | 5.67 | (0.138, 0.127) |
| Example 2-23 | Compound 23 | 4.64 | 5.65 | (0.137, 0.125) |
| Example 2-24 | Compound 24 | 4.61 | 5.68 | (0.137, 0.125) |
| Example 2-25 | Compound 25 | 4.60 | 5.64 | (0.136, 0.125) |
| Comparative Example 2-1 | HT1 | 4.96 | 5.33 | (0.136, 0.127) |
| Comparative Example 2-2 | HT2 | 4.98 | 5.34 | (0.136, 0.127) |

As seen in Table 2, it was seen that Examples 2-1 to 2-25 exhibited low voltage and high efficiency properties compared to Comparative Examples 2-1 and 2-2. Particularly, Compounds 13 to 21 substituted with a carbazole group exhibited the lowest voltage and the highest efficiency among the above-mentioned compounds, and following Compounds 13 to 21, low voltage and high efficiency properties were exhibited in the order of Compounds 8 to 12 substituted with an amine group, Compounds 1 to 7 substituted with an aryl group, and Compounds 22 to 25 substituted with an heteroaryl group.

It was identified that the compound derivatives of the chemical formulae according to the present invention had an excellent hole transferring ability thereby exhibited low voltage and high efficiency properties, and were capable of being used in an organic light emitting device.

Example 3

Example 3-1

The compounds synthesized in the synthesis example were high-purity sublimation purified using commonly known methods, and then a green organic light emitting device was manufactured using a method as below.

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

An organic EL device was manufactured by forming a light emitting device in the order of m-MTDATA (60 nm)/TCTA (80 nm)/CBP+10% Ir(ppy)$_3$ (300 nm)/BCP (10 nm)/

Alq₃ (30 nm)/LiF (1 nm)/Al (200 nm) on the transparent ITO electrode prepared as above using Compound 26 as a host.

Structures of the m-MTDATA, the TCTA, the Ir(ppy)₃ and the BCP are as follows.

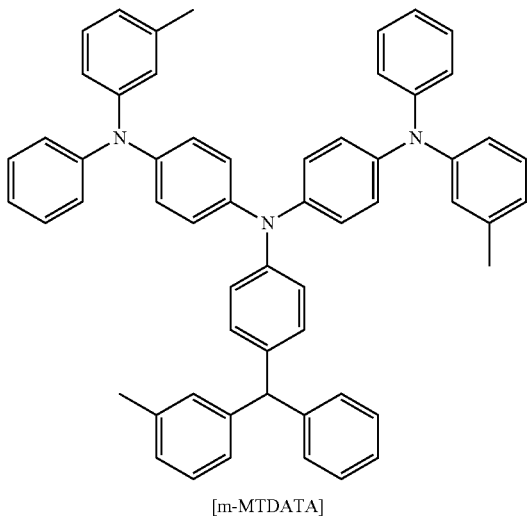

[m-MTDATA]

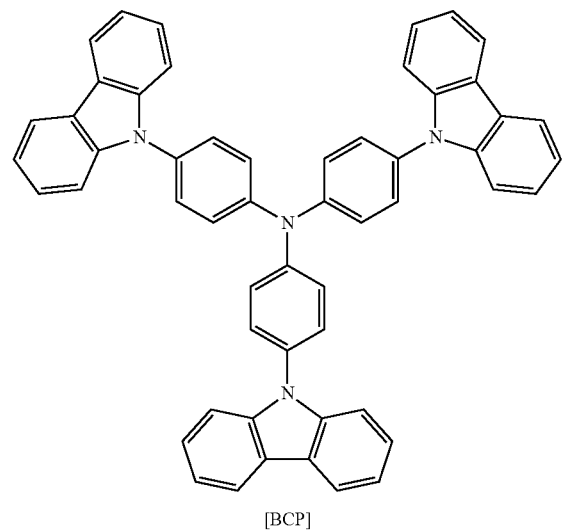

[BCP]

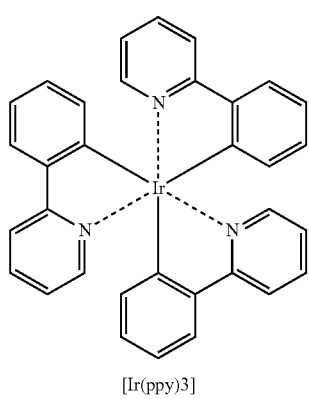

[Ir(ppy)3]

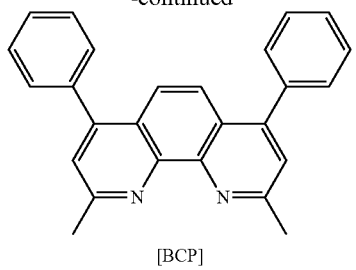

[BCP]

Example 3-2

An organic light emitting device was manufactured in the same manner as in Example 3-1 except that Compound 27 was used instead of Compound 26.

Example 3-3

An organic light emitting device was manufactured in the same manner as in Example 3-1 except that Compound 28 was used instead of Compound 26.

Example 3-4

An organic light emitting device was manufactured in the same manner as in Example 3-1 except that Compound 29 was used instead of Compound 26.

Example 3-5

An organic light emitting device was manufactured in the same manner as in Example 3-1 except that Compound 30 was used instead of Compound 26.

Example 3-6

An organic light emitting device was manufactured in the same manner as in Example 3-1 except that Compound 31 was used instead of Compound 26.

Example 3-7

An organic light emitting device was manufactured in the same manner as in Example 3-1 except that Compound 32 was used instead of Compound 26.

Example 3-8

An organic light emitting device was manufactured in the same manner as in Example 3-1 except that Compound 33 was used instead of Compound 26.

Example 3-9

An organic light emitting device was manufactured in the same manner as in Example 3-1 except that Compound 34 was used instead of Compound 26.

Comparative Example 3-1

An organic light emitting device was manufactured in the same manner as in Example 3-1 except that GH 1 (CBP) was used instead of Compound 26.

[GH 1]

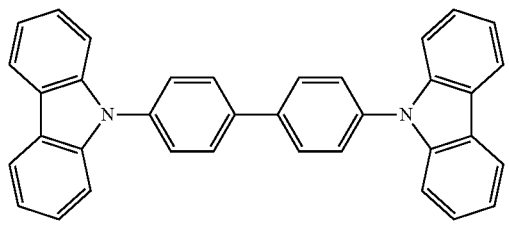

Comparative Example 3-2

An organic light emitting device was manufactured in the same manner as in Example 3-1 except that GH 2 was used instead of Compound 26.

[GH 2]

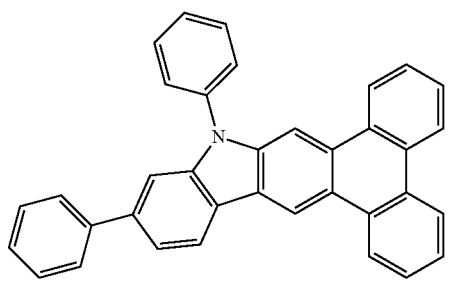

When a current was applied to the organic light emitting devices manufactured in Examples 3-1 to 3-9, and Comparative Examples 3-1 and 3-2, the results of Table 3 were obtained.

TABLE 3

| Compound (Host) | Voltage (V@10 mA/cm$^2$) | Efficiency (cd/A@10 mA/cm$^2$) | EL Peak (nm) |
|---|---|---|---|
| Example 3-1 Compound 26 | 6.90 | 42.93 | 517 |
| Example 3-2 Compound 27 | 6.92 | 42.64 | 516 |
| Example 3-3 Compound 28 | 6.95 | 42.62 | 518 |
| Example 3-4 Compound 29 | 6.85 | 42.75 | 517 |
| Example 3-5 Compound 30 | 6.88 | 42.51 | 515 |
| Example 3-6 Compound 31 | 6.89 | 42.53 | 516 |
| Example 3-7 Compound 32 | 6.75 | 42.52 | 516 |
| Example 3-8 Compound 33 | 6.77 | 42.54 | 517 |
| Example 3-9 Compound 34 | 6.78 | 42.58 | 518 |
| Comparative Example 3-1 GH1 | 7.21 | 40.42 | 517 |
| Comparative Example 3-2 CH2 | 7.28 | 39.97 | 518 |

Based on the test results, the green organic EL devices of Examples 3-1 to 3-9 using the compounds represented by Compounds 26 to 34 according to the present invention as a host material of the light emitting layer exhibited superior performance in terms of current efficiency and a driving voltage compared to existing green organic EL devices of Comparative Example 3-1 using CBP (GH 1) and Comparative Example 3-2 using GH2. As seen in Table 3, high efficiency and low voltage properties were exhibited in the order of a case substituted at the meta position of the phenyl (L) as in Compounds 32 to 34, a case substituted at the para position as in Compounds 29 to 31, and a case of direct bonding as in Compounds 26 to 28.

Example 4

Example 4-1

The compounds synthesized in the synthesis example were high-purity sublimation purified using commonly known methods, and then a red organic light emitting device was manufactured using a method as below.

An ITO glass was patterned so that a light emitting area became a 2 mm×2 mm size, and then washed. After installing the substrate in a vacuum chamber, the base pressure was set at 1×10$^{-6}$ torr, and as organic materials on the ITO, DNTPD (700 Å), α-NPB (300 Å), Compound 26 as a host (90 wt %), and the following (piq)$_2$Ir(acac) (10 wt %) as a dopant (300 Å) were vacuum deposited, then Alq$_3$ (350 Å), LiF (5 Å) and Al (1,000 Å) were layered in this order, and measurements were carried out at 0.4 mA.

The structures of the DNTPD, the α-NPB, the (piq)$_2$Ir (acac) and the Alq$_3$ are as follows.

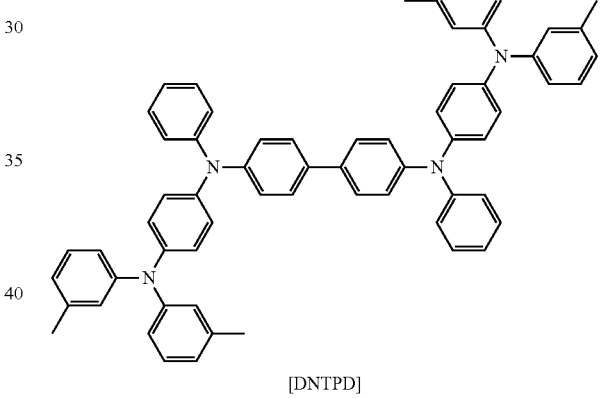

[DNTPD]

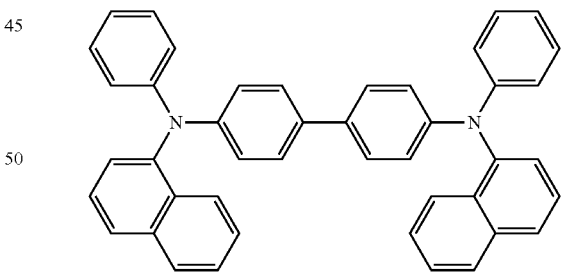

[α-NPB]

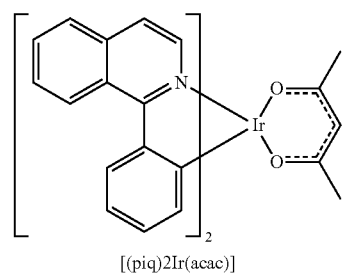

[(piq)2Ir(acac)]

-continued

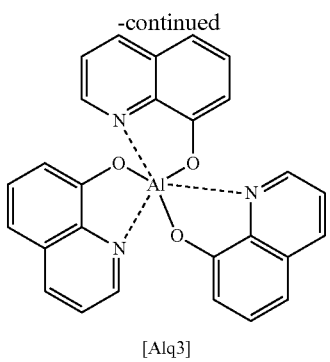

[Alq3]

Example 4-2

An organic light emitting device was manufactured in the same manner as in Example 4-1 except that Compound 27 was used instead of Compound 26.

Example 4-3

An organic light emitting device was manufactured in the same manner as in Example 4-1 except that Compound 28 was used instead of Compound 26.

Example 4-4

An organic light emitting device was manufactured in the same manner as in Example 4-1 except that Compound 35 was used instead of Compound 26.

Example 4-5

An organic light emitting device was manufactured in the same manner as in Example 4-1 except that Compound 36 was used instead of Compound 26.

Example 4-6

An organic light emitting device was manufactured in the same manner as in Example 4-1 except that Compound 37 was used instead of Compound 26.

Example 4-7

An organic light emitting device was manufactured in the same manner as in Example 4-1 except that Compound 38 was used instead of Compound 26.

Example 4-8

An organic light emitting device was manufactured in the same manner as in Example 4-1 except that Compound 39 was used instead of Compound 26.

Example 4-9

An organic light emitting device was manufactured in the same manner as in Example 4-1 except that Compound 40 was used instead of Compound 26.

Comparative Example 4-1

An organic light emitting device was manufactured in the same manner as in Example 4-1 except that RH 1 (CBP) was used instead of Compound 26.

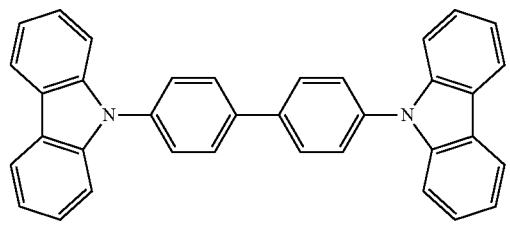

[RH 1]

For the organic light emitting devices manufactured according to Examples 4-1 to 4-9 and Comparative Example 4-1, a voltage, luminance, color coordinates and a lifespan were measured, and the results are shown in the following [Table 4]. T95 means time taken for the luminance decreasing to 95% of its initial luminance (5000 nit).

TABLE 4

|  | Host | Dopant | Voltage (V) | Luminance (cd/m$^2$) | Color Coordinates (x, y) | T95 |
|---|---|---|---|---|---|---|
| Example 4-1 | Compound 26 | (piq)$_2$Ir(acac) | 4.3 | 1920 | (0.670, 0.329) | 465 |
| Example 4-2 | Compound 27 | (piq)$_2$Ir(acac) | 4.2 | 1890 | (0.674, 0.325) | 455 |
| Example 4-3 | Compound 28 | (piq)$_2$Ir(acac) | 4.1 | 1900 | (0.672, 0.327) | 440 |
| Example 4-4 | Compound 35 | (piq)$_2$Ir(acac) | 4.3 | 1880 | (0.673, 0.335) | 435 |
| Example 4-5 | Compound 36 | (piq)$_2$Ir(acac) | 3.9 | 1890 | (0.675, 0.333) | 465 |
| Example 4-6 | Compound 37 | (piq)$_2$Ir(acac) | 4.2 | 1880 | (0.670, 0.339) | 450 |
| Example 4-7 | Compound 38 | (piq)$_2$Ir(acac) | 4.3 | 1870 | (0.671, 0.338) | 445 |
| Example 4-8 | Compound 39 | (piq)$_2$Ir(acac) | 4.3 | 1960 | (0.668, 0.329) | 465 |
| Example 4-9 | Compound 40 | (piq)$_2$Ir(acac) | 4.2 | 1910 | (0.673, 0.325) | 435 |
| Comparative Example 4-1 | RH1 | (piq)$_2$Ir(acac) | 4.7 | 1740 | (0.670, 0.327) | 415 |

Based on the test results, it was identified that the red organic EL devices of Example 4-1 to Example 4-9 using Compounds 26 to 28, 35 to 40 according to the present invention as a host material of the light emitting layer exhibited superior performance in terms of driving voltage and lifespan properties compared to an existing red organic EL device of Comparative Example 4-1 using CBP. Particularly, the compound in which quinazoline is substituted with a naphthyl group as in Compound 36 exhibited a low voltage property, and the compound substituted with a dimethylfluorene group as in Compound 38 exhibited an excellent property in terms of efficiency.

Hereinbefore, preferred embodiments of the present invention (electron blocking layer, hole transfer layer, green light emitting layer, red light emitting layer) have been described, however, the present invention is not limited thereto, and various modifications may be made within the scope of the claims and the detailed descriptions, and the modifications are also included in the scope of the present invention.

REFERENCE NUMERAL

1: Substrate
2: Anode
3: Light Emitting Layer
4: Cathode
5: Hole Injection Layer
6: Hole Transfer Layer
7: Light Emitting Layer
8: Electron Transfer Layer

The invention claimed is:
1. A compound selected from among the following compounds:

1-37

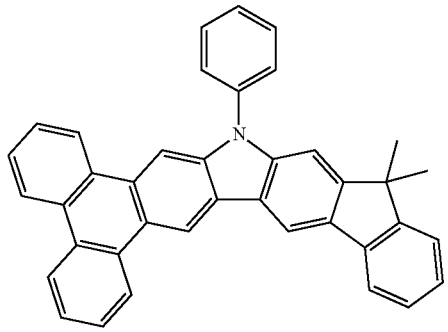

1-38

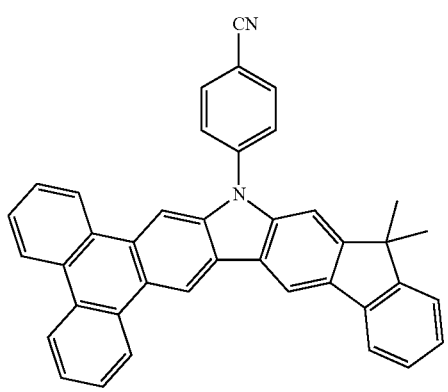

1-39

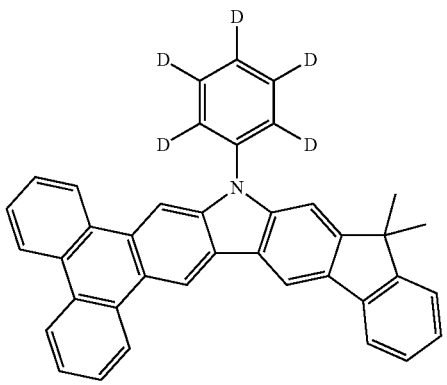

1-40

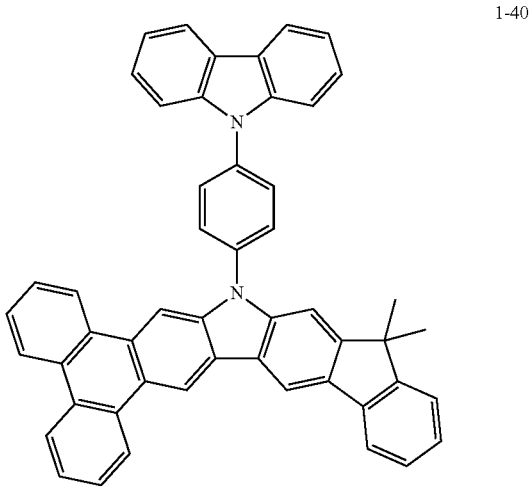

1-41

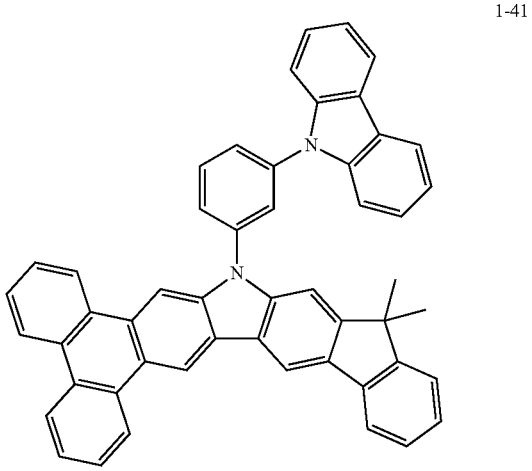

-continued
1-43
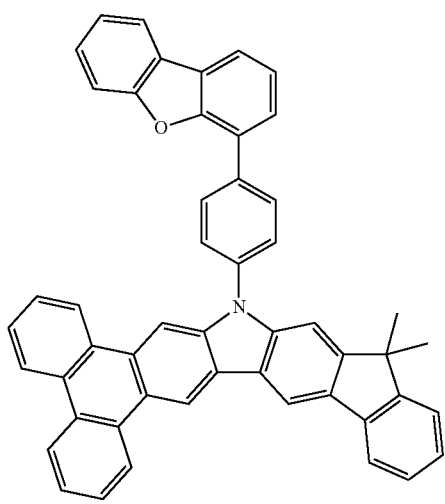
1-46
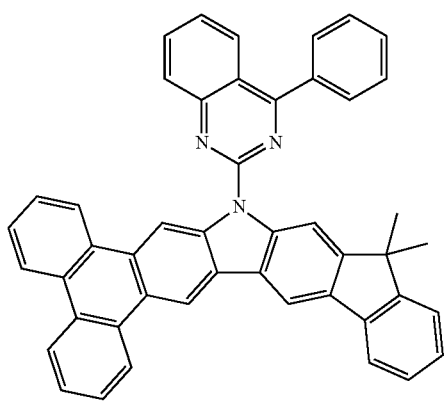
1-47
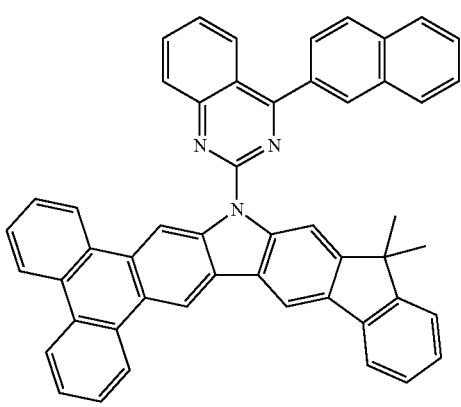
-continued
1-48
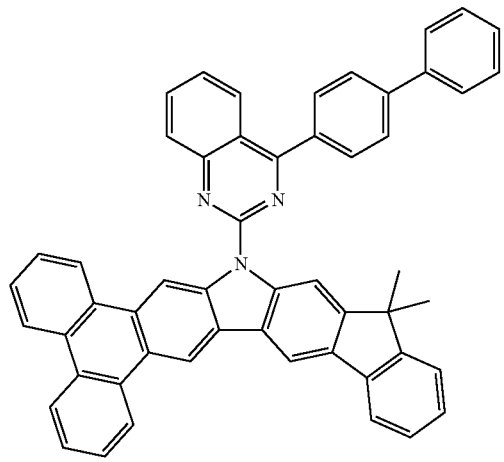
1-49
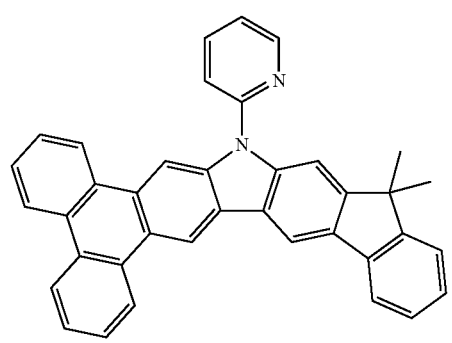
1-50
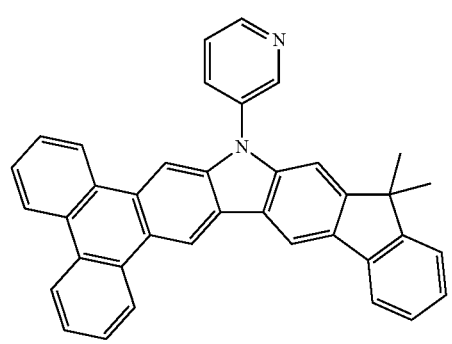
1-51
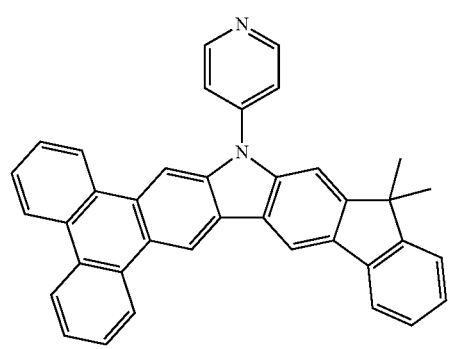

1-52
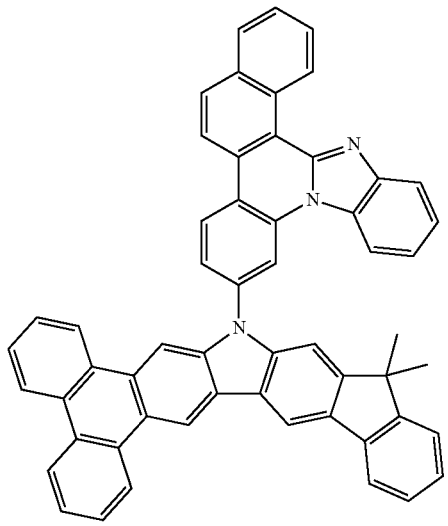
1-53
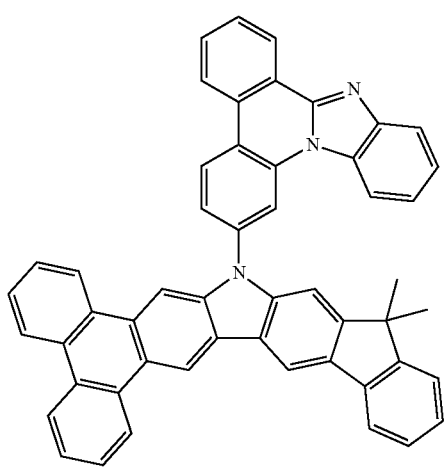
1-54
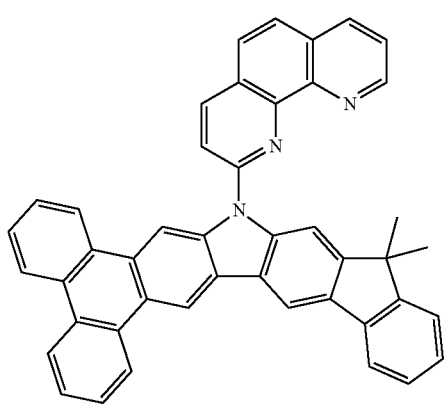
1-56
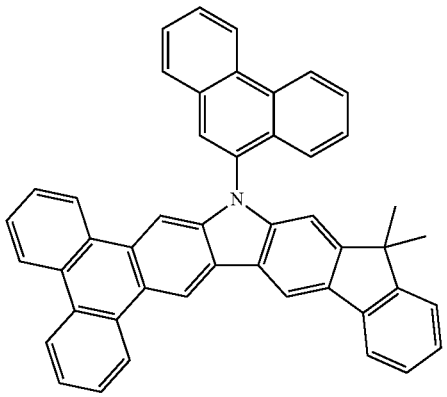
1-57
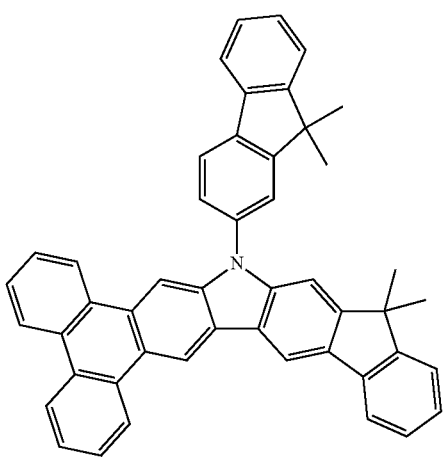
1-59
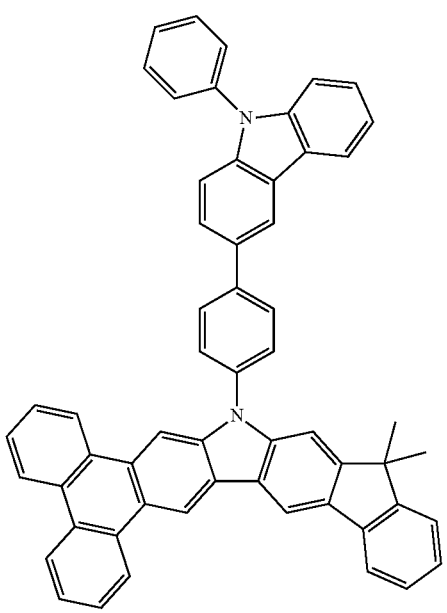

1-60

1-61

1-62

1-63

1-64

1-65

1-66
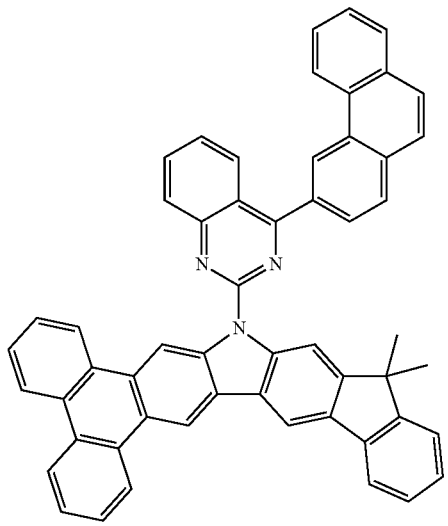
1-67
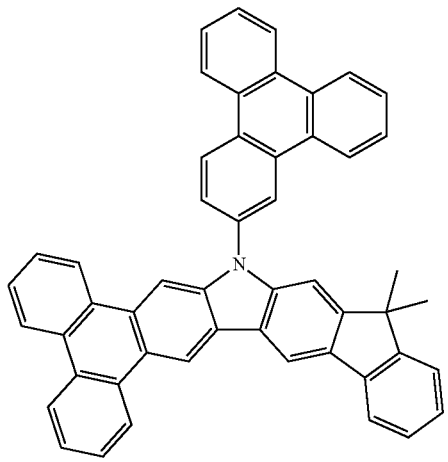
1-68
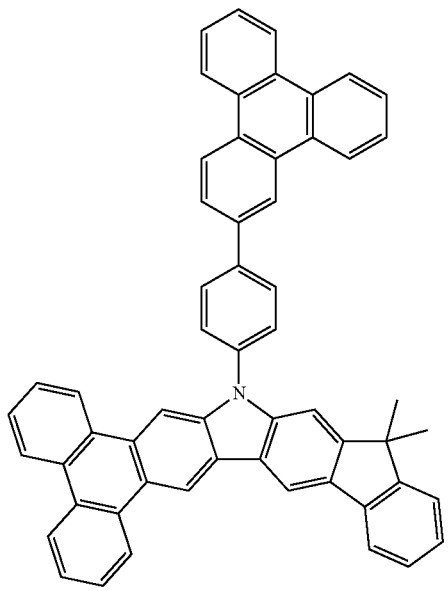
1-69
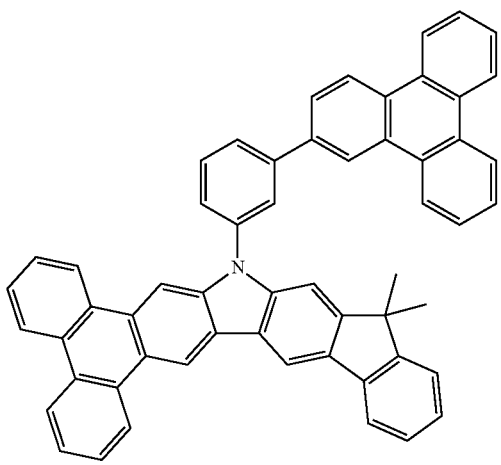
1-70
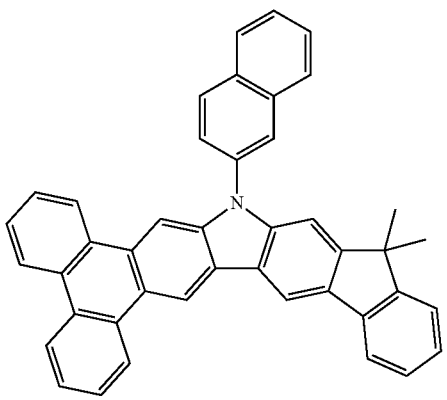
1-71
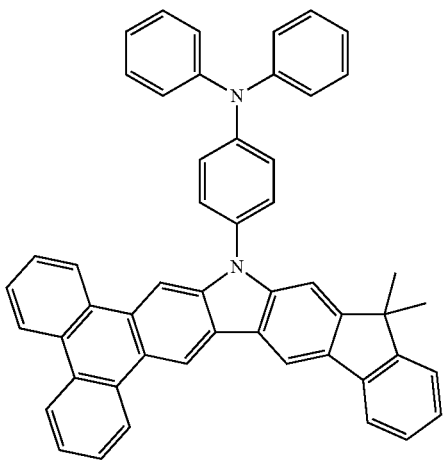

119
-continued
1-72
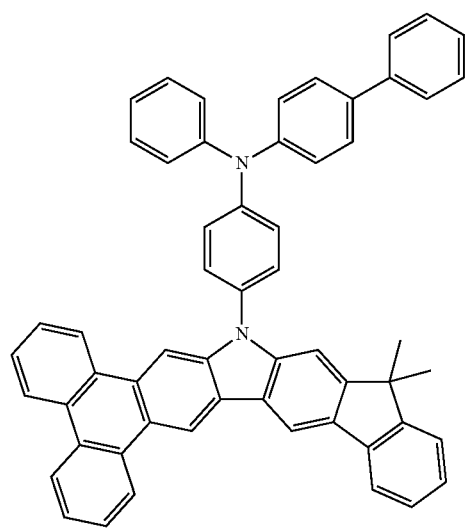
1-73
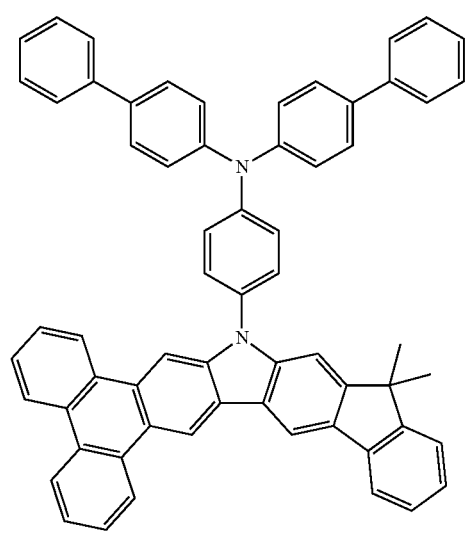
1-74
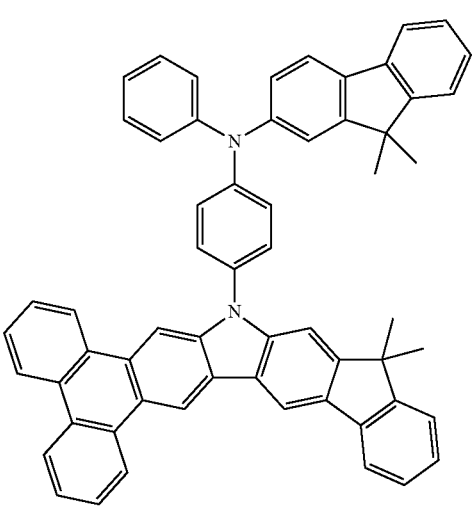
120
-continued
1-75
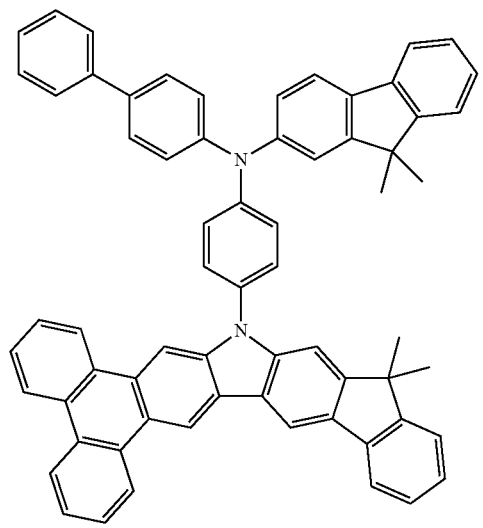
1-76
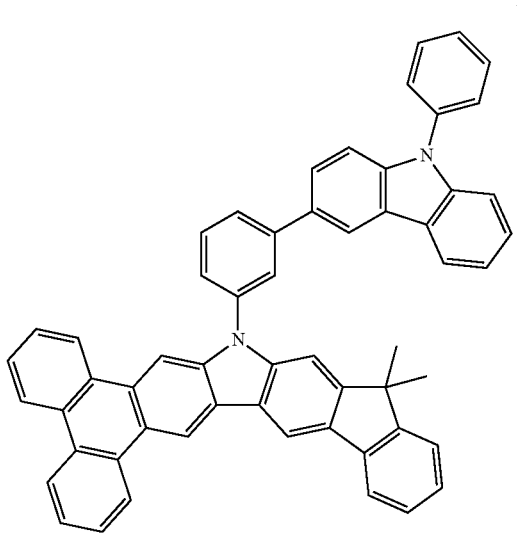
1-77
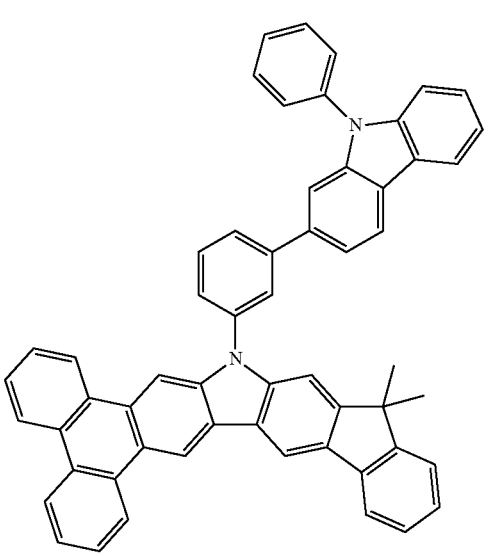

121
-continued
122
-continued
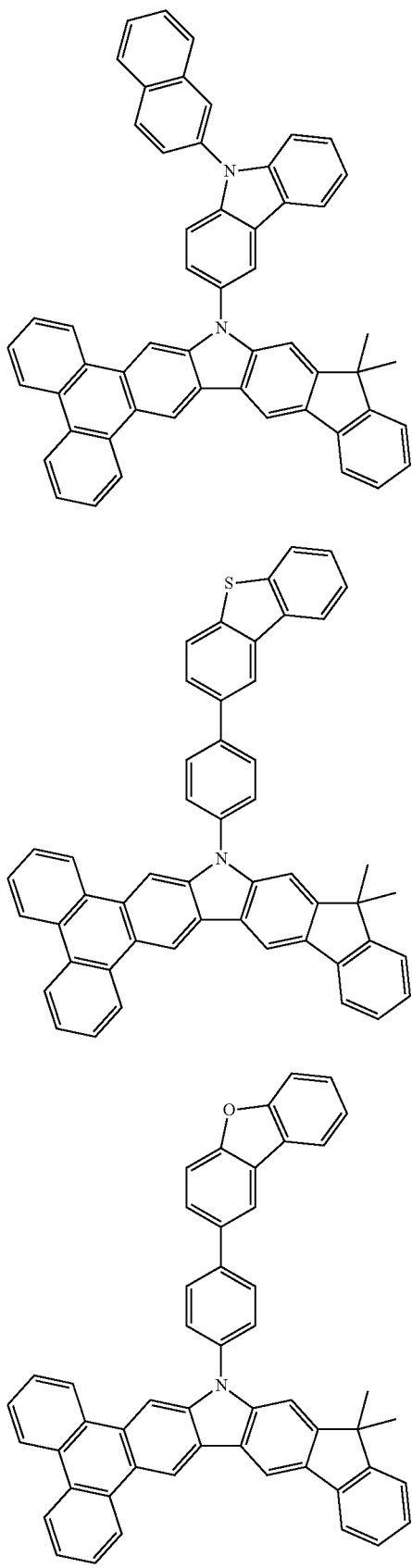
1-78
1-79
1-80
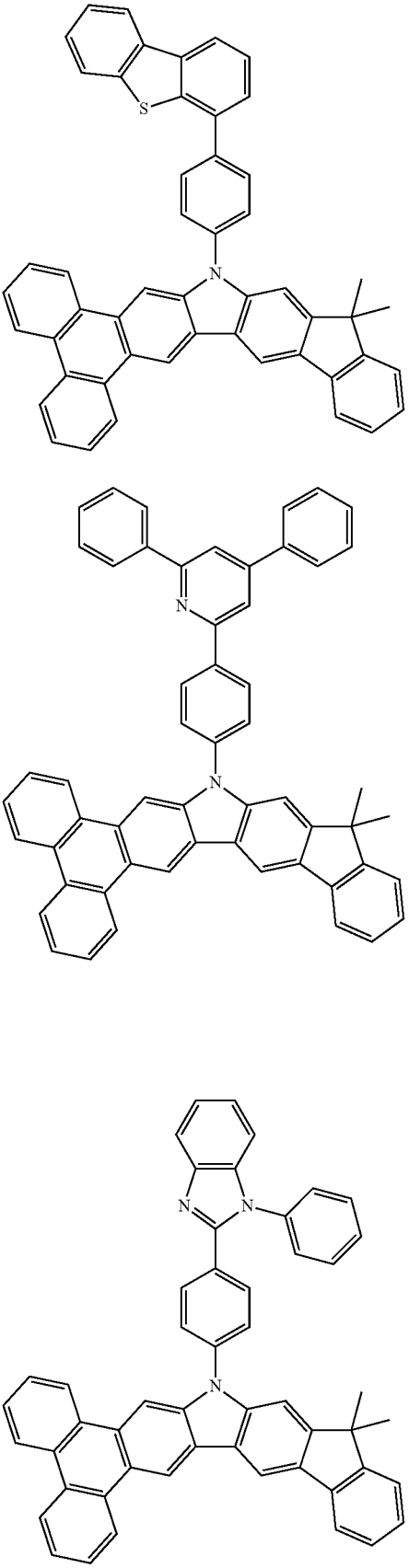
1-81
1-82
1-85

-continued
1-86
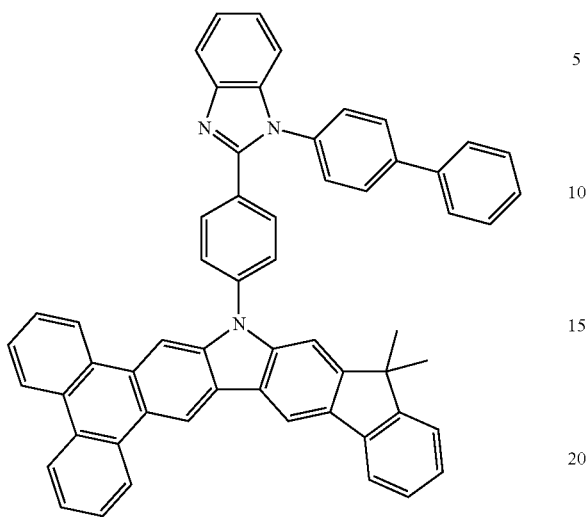
1-87
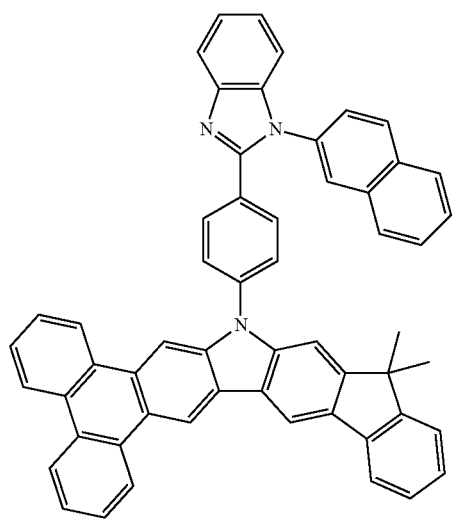
1-88
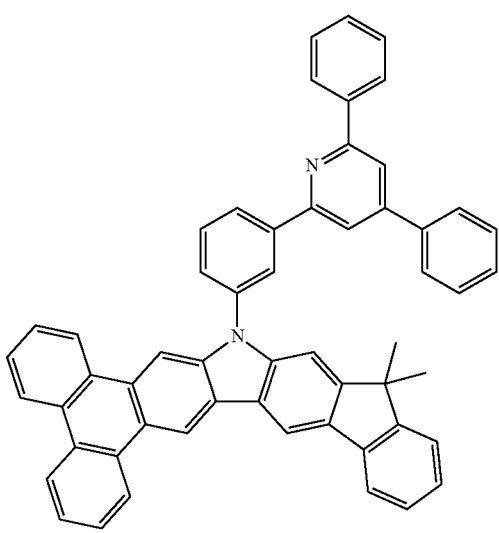
1-89
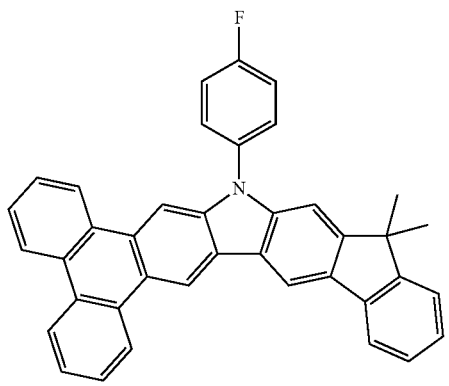
1-90
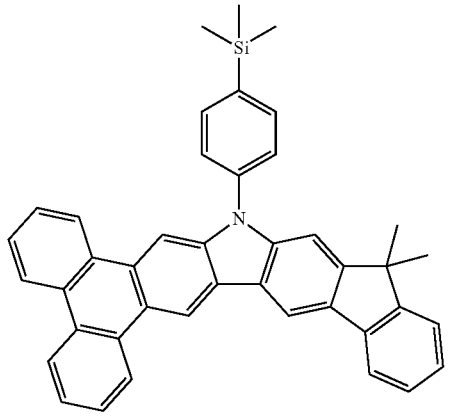
1-91
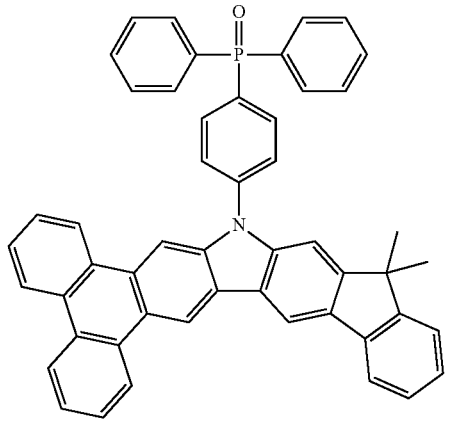

-continued
1-92
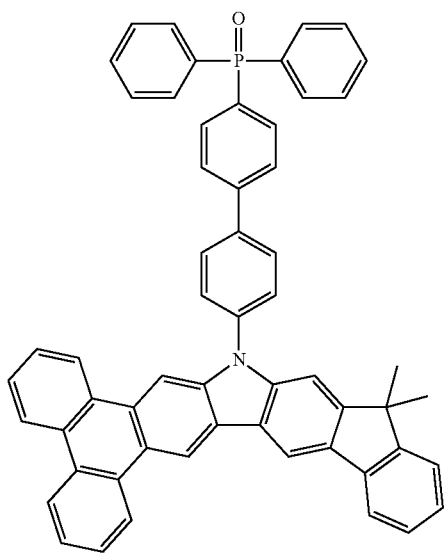
1-93
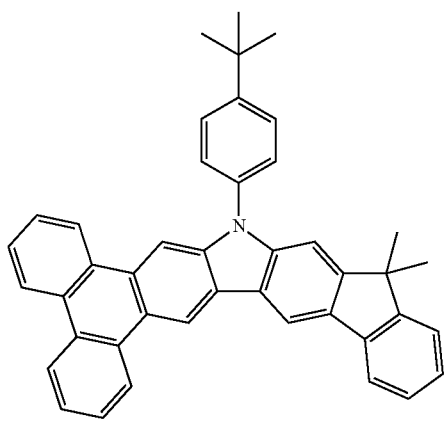
1-94
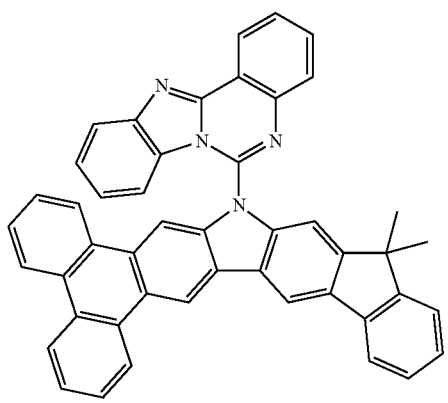
-continued
1-95
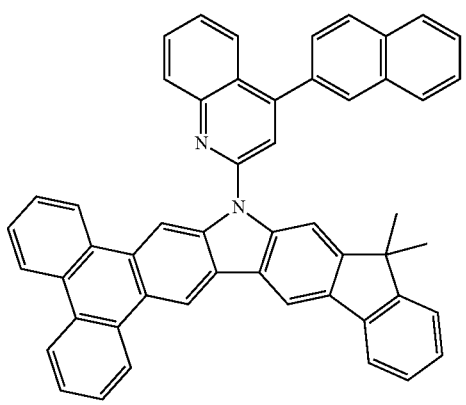
1-96
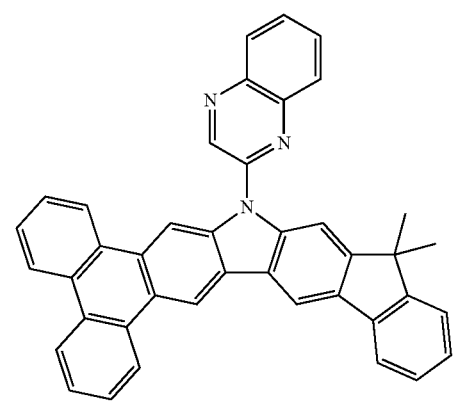
1-97
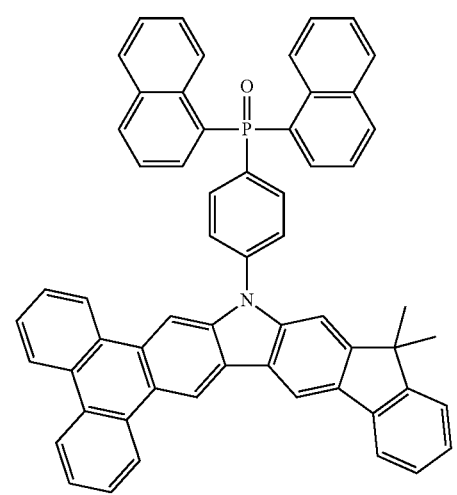

-continued 1-98

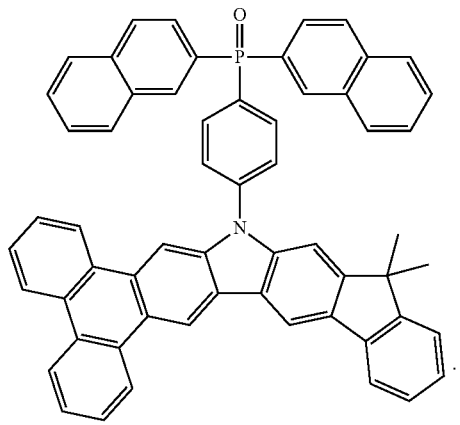

2. An organic light emitting device comprising:
a first electrode;
a second electrode provided opposite to the first electrode; and
one or more organic material layers provided between the first electrode and the second electrode,
wherein one or more layers of the organic material layers include the compound of claim 1.

3. The organic light emitting device of claim 2, wherein the organic material layer including the compound is an electron injection layer; an electron transfer layer; or a layer carrying out electron injection and electron transfer at the same time.

4. The organic light emitting device of claim 2, wherein the organic material layer including the compound is a light emitting layer.

5. An organic light emitting device comprising:
a first electrode;
a second electrode provided opposite to the first electrode; and
one or more organic material layers provided between the first electrode and the second electrode,
wherein one or more layers of the organic material layers include the compound of Chemical Formula 1:

[Chemical Formula 1]

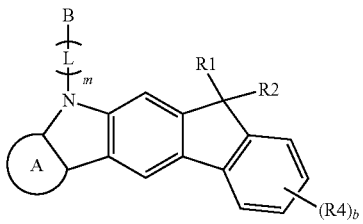

wherein, in Chemical Formula 1,
B is hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group;
L is a direct bond; or a substituted or unsubstituted arylene;
R1, R2 and R4 are the same as or different from each other, and each independently hydrogen; deuterium; a halogen group; a nitrile group; a nitro group; a hydroxyl group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted heterocyclic group, or bond to adjacent groups to form a substituted or unsubstituted ring;
A is triphenylene;
b is an integer of 0 to 4;
m is an integer of 0 to 10; and
when b and m are each two or greater, structures in the parentheses are the same as or different from each other,
wherein the organic material layer including the compound is a hole injection layer; a hole transfer layer; an electron blocking layer; or a layer carrying out hole injection and hole transfer at the same time.

* * * * *